US012697473B2

(12) United States Patent (10) Patent No.: US 12,697,473 B2
Ross (45) Date of Patent: Aug. 4, 2026

(54) DEVICE FOR DELIVERY OF RHEUMATOID ARTHRITIS MEDICATION

(71) Applicant: SOFUSA HOLDING LLC, New York, NY (US)

(72) Inventor: Russell Frederick Ross, Jacksonville Beach, FL (US)

(73) Assignee: SOFUSA HOLDINGS LLC, New York, NY (US)

( * ) Notice: Subject to any disclaimer, the term of this patent is extended or adjusted under 35 U.S.C. 154(b) by 679 days.

(21) Appl. No.: 18/148,025

(22) Filed: Dec. 29, 2022

(65) Prior Publication Data

US 2023/0137871 A1 May 4, 2023

Related U.S. Application Data

(60) Division of application No. 16/896,941, filed on Jun. 9, 2020, now Pat. No. 11,565,098, which is a
(Continued)

(51) Int. Cl.
*A61M 37/00* (2006.01)
*A61L 31/00* (2006.01)
*A61M 5/158* (2006.01)

(52) U.S. Cl.
CPC ......... *A61M 37/0015* (2013.01); *A61L 31/00* (2013.01); *A61M 5/158* (2013.01);
(Continued)

(58) Field of Classification Search
CPC .............. A61M 37/0015; A61M 5/158; A61M 2037/0023; A61M 2037/003;
(Continued)

(56) References Cited

U.S. PATENT DOCUMENTS 3,797,494 A 3/1974 Zaffaroni
3,964,482 A 6/1976 Gerstel et al.
(Continued)

FOREIGN PATENT DOCUMENTS

EP 2100850 A1 9/2009
WO 9945860 A1 9/1999
(Continued)

OTHER PUBLICATIONS

Abstract of Japanese Patent—JP2001238964, Sep. 4, 2001, 1 page.
(Continued)

*Primary Examiner* — Kami A Bosworth
*Assistant Examiner* — Avery Smale
(74) *Attorney, Agent, or Firm* — PROCOPIO, CORY, HARGREAVES & SAVITCH LLP

(57) ABSTRACT

Disclosed are devices for delivering a rheumatoid arthritis drug across a dermal barrier. The devices include microneedles for penetrating the stratum corneum and also include structures fabricated on a surface of the microneedles to form a nanotopography. A random or non-random pattern of structures may be fabricated such as a complex pattern including structures of differing sizes and/ or shapes. The pattern of structures on the surface of the microneedles may include nano-sized structures.

11 Claims, 29 Drawing Sheets

Related U.S. Application Data continuation of application No. 16/040,714, filed on Jul. 20, 2018, now Pat. No. 10,709,884, which is a continuation of application No. 15/378,097, filed on Dec. 14, 2016, now Pat. No. 10,029,082, which is a continuation of application No. 13/641,501, filed as application No. PCT/IB2011/051861 on Apr. 27, 2011, now Pat. No. 9,522,263.

(60) Provisional application No. 61/435,973, filed on Jan. 25, 2011, provisional application No. 61/411,101, filed on Nov. 8, 2010, provisional application No. 61/328,723, filed on Apr. 28, 2010.

(52) U.S. Cl.
CPC ............... *A61M 2037/0023* (2013.01); *A61M 2037/003* (2013.01); *A61M 2037/0061* (2013.01); *Y10T 29/49* (2015.01)

(58) Field of Classification Search
CPC .......... A61M 2037/0061; A61M 37/00; A61M 2037/0053; A61L 31/00; A61P 29/00; A61P 19/02; Y10T 29/49
See application file for complete search history.

(56) References Cited

U.S. PATENT DOCUMENTS

| | | | |
|---|---|---|---|
| 4,031,894 A | 6/1977 | Urquhart et al. | |
| 4,051,840 A | 10/1977 | Kantrowitz et al. | |
| 4,201,211 A | 5/1980 | Chandrasekaran et al. | |
| 4,379,454 A | 4/1983 | Campbell et al. | |
| 4,436,741 A | 3/1984 | Urquhart et al. | |
| 4,588,580 A | 5/1986 | Gale et al. | |
| 4,615,699 A | 10/1986 | Gale et al. | |
| 4,661,105 A | 4/1987 | Gale | |
| 4,681,584 A | 7/1987 | Gale et al. | |
| 4,698,062 A | 10/1987 | Gale et al. | |
| 4,725,272 A | 2/1988 | Gale | |
| 4,832,953 A | 5/1989 | Campbell et al. | |
| 4,880,633 A | 11/1989 | Loper et al. | |
| 4,908,027 A | 3/1990 | Enscore et al. | |
| 5,004,610 A | 4/1991 | Osborne et al. | |
| 5,310,559 A | 5/1994 | Shah et al. | |
| 5,328,470 A | 7/1994 | Nabel et al. | |
| 5,342,623 A | 8/1994 | Enscore et al. | |
| 5,344,565 A | 9/1994 | Enscore et al. | |
| 5,364,630 A | 11/1994 | Osborne et al. | |
| 6,132,755 A | 10/2000 | Eicher et al. | |
| 6,312,612 B1 | 11/2001 | Sherman et al. | |
| 6,313,612 B1 | 11/2001 | Hona et al. | |
| 6,334,856 B1 | 1/2002 | Allen et al. | |
| 6,375,978 B1 | 4/2002 | Kleiner et al. | |
| 6,471,993 B1 | 10/2002 | Shastri et al. | |
| 6,569,143 B2 | 5/2003 | Alchas et al. | |
| 6,591,124 B2 | 7/2003 | Sherman et al. | |
| 6,656,147 B1 | 12/2003 | Gertsek et al. | |
| 6,663,820 B2 | 12/2003 | Arias et al. | |
| 6,767,341 B2 | 7/2004 | Cho | |
| 6,881,203 B2 | 4/2005 | Delmore et al. | |
| 6,908,453 B2 | 6/2005 | Fleming et al. | |
| 6,926,953 B2 | 8/2005 | Nealey et al. | |
| 6,979,347 B1 | 12/2005 | Wu et al. | |
| 6,995,336 B2 | 2/2006 | Hunt et al. | |
| 7,048,723 B1 | 5/2006 | Frazier et al. | |
| 7,066,922 B2 | 6/2006 | Angel et al. | |
| 7,108,681 B2 | 9/2006 | Garstein et al. | |
| 7,115,108 B2 | 10/2006 | Wilkinson et al. | |
| 7,129,554 B2 | 10/2006 | Lieber et al. | |
| 7,131,987 B2 | 11/2006 | Sherman et al. | |
| 7,185,663 B2 | 3/2007 | Koch et al. | |
| 7,189,435 B2 | 3/2007 | Tuominen et al. | |
| 7,226,439 B2 | 6/2007 | Prausnitz et al. | |
| 7,250,037 B2 | 7/2007 | Shermer et al. | |
| 7,285,113 B2 | 10/2007 | Yeshurun | |
| 7,315,758 B2 | 1/2008 | Kwiatkowski et al. | |
| 7,332,339 B2 | 2/2008 | Canham | |
| 7,364,568 B2 | 4/2008 | Angel et al. | |
| 7,374,864 B2 * | 5/2008 | Guo ...................... B82Y 40/00 | |
| | | | 264/494 |
| 7,374,884 B2 | 5/2008 | Guo et al. | |
| 7,416,541 B2 | 8/2008 | Yuzhakov et al. | |
| 7,429,258 B2 | 9/2008 | Angel et al. | |
| 7,449,200 B2 | 11/2008 | Sung et al. | |
| 7,473,244 B2 | 1/2009 | Frazier et al. | |
| 7,531,120 B2 | 5/2009 | Van Rijn et al. | |
| 7,537,590 B2 | 5/2009 | Santini, Jr. et al. | |
| 7,544,770 B2 | 6/2009 | Haynie | |
| 7,556,615 B2 | 7/2009 | Pettis et al. | |
| 7,563,451 B2 | 7/2009 | Lin et al. | |
| 7,572,405 B2 | 8/2009 | Sherman et al. | |
| 7,578,954 B2 | 8/2009 | Gartstein | |
| 7,582,069 B2 | 9/2009 | Laurent et al. | |
| 7,588,552 B2 | 9/2009 | Yeshurun | |
| 7,611,481 B2 | 11/2009 | Cleary et al. | |
| 7,627,938 B2 | 12/2009 | Kim et al. | |
| 7,651,475 B2 | 1/2010 | Angel et al. | |
| 7,658,728 B2 | 2/2010 | Yuzhakov | |
| 7,803,574 B2 | 9/2010 | Desai et al. | |
| 7,828,827 B2 | 11/2010 | Garstein et al. | |
| 7,846,488 B2 | 12/2010 | Johnson et al. | |
| 7,901,387 B2 | 3/2011 | Stemme et al. | |
| 7,914,480 B2 | 3/2011 | Cleary et al. | |
| 7,914,813 B2 | 3/2011 | Adachi et al. | |
| 7,918,814 B2 | 4/2011 | Prausnitz et al. | |
| 7,981,346 B2 | 7/2011 | Griss et al. | |
| 7,997,274 B2 | 8/2011 | Baska | |
| 8,052,633 B2 | 11/2011 | Kendall | |
| 8,088,321 B2 | 1/2012 | Ferguson et al. | |
| 8,097,456 B2 | 1/2012 | Borenstein et al. | |
| 8,118,753 B2 | 2/2012 | Cho et al. | |
| 8,137,697 B1 | 3/2012 | Sung et al. | |
| 8,137,736 B2 | 3/2012 | Zhu et al. | |
| 8,238,995 B2 | 8/2012 | Chandrasekaran et al. | |
| 8,366,677 B2 | 2/2013 | Kaspar et al. | |
| 8,389,205 B2 | 3/2013 | Duerig et al. | |
| 8,419,708 B2 | 4/2013 | Tokumoto et al. | |
| 8,506,530 B2 | 8/2013 | Laermer et al. | |
| 8,574,615 B2 | 11/2013 | Tenney et al. | |
| 8,690,838 B2 | 4/2014 | Ozawa et al. | |
| 8,696,637 B2 | 4/2014 | Ross | |
| 8,915,957 B2 | 12/2014 | Arney et al. | |
| 8,944,804 B2 | 2/2015 | Robeson et al. | |
| 9,028,409 B2 | 5/2015 | Yodfat et al. | |
| 9,522,263 B2 | 12/2016 | Ross | |
| 9,526,883 B2 | 12/2016 | Ross | |
| 10,029,082 B2 | 7/2018 | Ross | |
| 10,029,084 B2 | 7/2018 | Ross | |
| 10,806,914 B2 | 10/2020 | Ross | |
| 11,129,975 B2 | 9/2021 | Ross | |
| 2002/0082543 A1 | 6/2002 | Park et al. | |
| 2002/0133129 A1 | 9/2002 | Arias et al. | |
| 2002/0138049 A1 | 9/2002 | Allen et al. | |
| 2002/0183688 A1 | 12/2002 | Lastovich et al. | |
| 2003/0220656 A1 * | 11/2003 | Gartstein ............. A61B 17/205 | |
| | | | 606/131 |
| 2004/0028875 A1 | 2/2004 | Van Rijn et al. | |
| 2004/0063100 A1 | 4/2004 | Wang | |
| 2004/0087992 A1 | 5/2004 | Gartstein et al. | |
| 2004/0106904 A1 | 6/2004 | Gonnelli et al. | |
| 2004/0176732 A1 * | 9/2004 | Frazier ............. A61M 37/0015 | |
| | | | 977/932 |
| 2005/0049625 A1 | 3/2005 | Shaya et al. | |
| 2005/0112135 A1 | 5/2005 | Cormier et al. | |
| 2005/0118388 A1 | 6/2005 | Kingsford | |
| 2005/0119723 A1 | 6/2005 | Peacock | |
| 2005/0124967 A1 | 6/2005 | Kaestner et al. | |
| 2005/0137531 A1 | 6/2005 | Prausnitz et al. | |
| 2005/0143713 A1 | 6/2005 | Delmore et al. | |
| 2005/0178760 A1 | 8/2005 | Chang et al. | |
| 2006/0024358 A1 | 2/2006 | Santini, Jr. et al. | |
| 2006/0025848 A1 | 2/2006 | Weber et al. | |
| 2006/0051404 A1 | 3/2006 | Yeshurun et al. | |

(56) References Cited

U.S. PATENT DOCUMENTS

| | | |
|---|---|---|
| 2006/0204738 A1 | 9/2006 | Dubrow et al. |
| 2006/0264893 A1 | 11/2006 | Sage et al. |
| 2007/0066934 A1 | 3/2007 | Etheredge, III et al. |
| 2007/0078376 A1 | 4/2007 | Smith |
| 2007/0081977 A1 | 4/2007 | Horstmann |
| 2007/0088248 A1 | 4/2007 | Glenn et al. |
| 2007/0110810 A1 | 5/2007 | Smith et al. |
| 2007/0112309 A1 | 5/2007 | Zucker |
| 2007/0112548 A1 | 5/2007 | Dickerson et al. |
| 2007/0191761 A1 | 8/2007 | Boone et al. |
| 2007/0249552 A1 | 10/2007 | Khalili et al. |
| 2007/0250018 A1 | 10/2007 | Adachi et al. |
| 2007/0260201 A1 | 11/2007 | Prausnitz et al. |
| 2007/0276318 A1 | 11/2007 | Henley |
| 2008/0051699 A1 | 2/2008 | Choi et al. |
| 2008/0091226 A1 | 4/2008 | Yeshurun et al. |
| 2008/0097352 A1 | 4/2008 | Beck et al. |
| 2008/0108958 A1 | 5/2008 | Carter et al. |
| 2008/0195035 A1 | 8/2008 | Frederickson et al. |
| 2008/0200883 A1 | 8/2008 | Tomono |
| 2008/0217180 A1 | 9/2008 | Doye et al. |
| 2008/0221408 A1 | 9/2008 | Hoarau et al. |
| 2008/0262416 A1 | 10/2008 | Duan et al. |
| 2008/0269666 A1 | 10/2008 | Wang et al. |
| 2008/0269685 A1 | 10/2008 | Singh et al. |
| 2008/0305989 A1 | 12/2008 | Wen et al. |
| 2008/0311172 A1 | 12/2008 | Schapira et al. |
| 2008/0312610 A1* | 12/2008 | Binks ...................... A61P 31/10 |
| | | 264/45.6 |
| 2009/0012494 A1 | 1/2009 | Yeshurun et al. |
| 2009/0043279 A1 | 2/2009 | Kaspar et al. |
| 2009/0069788 A1 | 3/2009 | Yeshurun et al. |
| 2009/0093776 A1 | 4/2009 | Yue et al. |
| 2009/0093871 A1 | 4/2009 | Rea et al. |
| 2009/0093879 A1 | 4/2009 | Wawro et al. |
| 2009/0099427 A1 | 4/2009 | Jina et al. |
| 2009/0099502 A1 | 4/2009 | Tokumoto et al. |
| 2009/0099537 A1 | 4/2009 | Devoe et al. |
| 2009/0118662 A1 | 5/2009 | Schnall |
| 2009/0118672 A1 | 5/2009 | Gonnelli et al. |
| 2009/0137926 A1 | 5/2009 | Srinivasan et al. |
| 2009/0177273 A1 | 7/2009 | Piveteau et al. |
| 2009/0187167 A1 | 7/2009 | Sexton et al. |
| 2009/0198189 A1 | 8/2009 | Simons et al. |
| 2009/0232870 A1 | 9/2009 | Srivastava et al. |
| 2010/0004733 A1 | 1/2010 | Atansoska et al. |
| 2010/0021464 A1 | 1/2010 | Archambeau et al. |
| 2010/0028604 A1 | 2/2010 | Bhushan et al. |
| 2010/0076035 A1 | 3/2010 | Carter et al. |
| 2010/0121307 A1 | 5/2010 | Lockard et al. |
| 2010/0168506 A1 | 7/2010 | Moon et al. |
| 2010/0215580 A1 | 8/2010 | Hanes et al. |
| 2010/0256568 A1 | 10/2010 | Frederickson et al. |
| 2010/0274203 A1 | 10/2010 | Lee et al. |
| 2010/0316960 A1 | 12/2010 | Duerig et al. |
| 2011/0021996 A1 | 1/2011 | Lee et al. |
| 2011/0046557 A1 | 2/2011 | Lee et al. |
| 2011/0059150 A1 | 3/2011 | Kendall et al. |
| 2011/0144591 A1 | 6/2011 | Ross et al. |
| 2011/0160069 A1 | 6/2011 | Corrie et al. |
| 2011/0270221 A1 | 11/2011 | Ross |
| 2011/0276003 A1 | 11/2011 | Luttge et al. |
| 2012/0089117 A1 | 4/2012 | Junginger et al. |
| 2012/0109065 A1 | 5/2012 | Backes |
| 2012/0114734 A1 | 5/2012 | Desai et al. |
| 2012/0128932 A1 | 5/2012 | Veith et al. |
| 2013/0144217 A1 | 6/2013 | Ross |
| 2013/0150822 A1 | 6/2013 | Ross |
| 2013/0158505 A1 | 6/2013 | Ross |
| 2013/0165861 A1 | 6/2013 | Ross |
| 2013/0211310 A1 | 8/2013 | Bommarito et al. |
| 2013/0331792 A1 | 12/2013 | Karp et al. |
| 2014/0112921 A1 | 4/2014 | Ross |
| 2015/0329362 A1 | 11/2015 | Aria et al. |

FOREIGN PATENT DOCUMENTS

| | | |
|---|---|---|
| WO | 2000074764 A1 | 12/2000 |
| WO | 0175164 A2 | 10/2001 |
| WO | 0230506 A2 | 4/2002 |
| WO | 0232480 A2 | 4/2002 |
| WO | 03020359 A2 | 3/2003 |
| WO | 03024508 A2 | 3/2003 |
| WO | 03092785 A1 | 11/2003 |
| WO | 2005049128 A1 | 6/2005 |
| WO | 2006062974 A2 | 6/2006 |
| WO | 2007012114 A1 | 2/2007 |
| WO | 2007112309 A2 | 10/2007 |
| WO | 2008003564 A1 | 1/2008 |
| WO | 2008024141 A2 | 2/2008 |
| WO | 2009079589 A2 | 6/2009 |
| WO | 2009113856 A1 | 9/2009 |
| WO | 2010070628 A1 | 6/2010 |
| WO | 2010087971 A2 | 8/2010 |
| WO | 2010126640 A2 | 11/2010 |
| WO | 2011116388 A1 | 9/2011 |
| WO | 2011135531 A2 | 11/2011 |
| WO | 2012/006677 A2 | 1/2012 |
| WO | 2012046149 A1 | 4/2012 |
| WO | 2013061208 A1 | 5/2013 |
| WO | 2013061209 A1 | 5/2013 |

OTHER PUBLICATIONS

Abstract of Japanese Patent—JP2008511382, Apr. 17, 2008, 2 pages.

Abstract of Japanese Patent—JP2008237673, Oct. 9, 2008, 1 page.

Abstract of Japanese Patent—JP2009207733, Sep. 17, 2009, 1 page.

Abstract of Japanese Patent—JPH08337521, Dec. 24, 1996, 2 pages.

Abstract of WIPO Patent—WO 2006/075689, Jul. 20, 2006, 1 page.

Ahmed et al; "Bis(diacetylene)s I: Langmuir-Blodgett films", Thin Solid Films 187: 141-153; 1990.

Ainslie et al., "Microfabricated implants for applications in therapeutic delivery, tissue engineering, and biosensing." Royal Society of Chemistry. 8. (2008): 1854-1878.

Ainslie et al., "Microfabricated Devices for Enhanced Bioadhesive Drug Delivery: Attachment to and Small-Molecule Release Through a Cell Monolayer Under Flow." Small. (2009).

Al-Qallaf et al., "Optimizing Microneedle Arrays to Increase Skin Permeability for Transdermal Drug Delivery," Interdisciplinary Transport Phenomena V: Ann. N.Y. Acad. Sci., 2009, pp. 1-12.

Bekarde, IiI Gercek. "Biomimetic Apatite-coated PCL Scaffolds: Effect of Surface Nanotopography on Cellular Functions." Journal of Bioactive and Compatible Polymers . 24.6 (2009): 507-524.

Berliner et al., "Impact of Transdermal Fentanyl on Quality of Life in Rheumatoid Arthritis", Clinical Journal of Pain, 2007, 23(6): 530-534.

Berry et al., "The interaction of human bone marrow cells with nanotopographical features in three dimensional constructs." Journal of Biomedical Materials Research Part A. 79A.2 (2006): 431-439.

Biehl et al., "Proliferation of Mouse Embryonic Stem Cell Progeny and the Spontaneous Contractile Activity of Cardiomyocytes Are Affected by Microtopography." Developmental Dynamics . 238. (2009): 1964-1973.

Biggs et al., "Interactions with Nanoscale Topography: Adhesion quantification and signal transduction in cells of osteogenic and multipotent lineage," Journal of Biomedical Materials Research Part A, 2008, pp. 195-208.

Brunauer et al., "Adsorption of Gases in Multimolecular Layers." Journal of the American Chemical Society. 60. (1938): 309-319.

Chandler, David L.. "PhysOrg.com." Harnessing nanopatterns: Tiny textures can produce big differences. N.p., Sep. 24, 2009. Web. Dec. 1, 2009. <http://www.physorg.com/news172004362.html>.

Choi et al. "Cell interaction with three-dimensional sharp-tip nanotopography." Biomaterials. 28.9 (2007): 1672-1679.

Chun et al., "The role of polymer nanosurcace roughness and the submicron pores in improving bladder urothelial cell density and inhibiting calcium oxalate stone formation." Nanotechnology. 20.8 (2009): 85104.

(56)                    References Cited

OTHER PUBLICATIONS

Citi, S., "Protein Kinase Inhibitors Prevent Junction Dissociation Induced by Low Extracellular Calcium in MDCK Epithelial Cells", J Cell Biology, 1992, 117(1) 169-178.

Cohn, Abby. "Drug Delivery, Nanoscale." Innovations. 3.4 (2009).

Curtis et al., "Cell signaling arising from nanotopography: implicatinos for nanomedicaldevices." Nanomedicine. 1.1 (2006): 67-72.

Dalby, Matthew J. "Nanostructured surfaces: cell engineering and cell biology." Nanomedicine. 4.3 (2009): 247-248.

Dalby et al., "Attempted endocytosis of nano-environment produced by colloidal lithography by human fibroblasts." Experimental Cell Research. 295. (2004): 387-394.

Dalby et al., "Nano-Topography Induces Mechanotransduction in Human Fibroblasts." European Cells and Materials . 6.2 (2003): 31.

Dalby et al., "Increasing Fibroblast Response to Materials Using Nanotopography: Morphological and Genetic measurements of Cell Response to 13-nm-High Polymer Demixed Islands." Experimental Cell Research. 276.1 (2002): 1-9.

Fischer et al., "Biomimetic Nanowire Coatings for Next Generation Adhesive Drug Delivery Systems." Nano Letters. 9.2 (2009): 716-720.

Geiger & Ayalon, "Cadherins", Annu Rev Cell Biol, 1992, 8:307-32.

Gumbiner & Simons, "A Functional Assay for Proteins Involved in Establishing an Epithelial Occluding Barrier: Identification of an Uvomorulin-like Polypeptide", J. Cell Biology, 1986, 102: 457-468.

Hart et al., "Filapodial Sensing of Nanotopography in Osteoprogenitor Cells." European Cells and Materials . 10.2 (2005): 65.

He et al., "The anatase phase of nanotopography titania plays an important role on osteoblast cell morphology and proliferation", Journal of Mater. Sci: Mater Med (2008), 19:3465-3472.

Hirano et al., "Calcium-dependent Cell-Cell Adhesion Molecules (Cadherins): Subclass Specificities and Possible Involvement of Actin Bundles", J. Cell Biology, 105(6): 2501-2510.

Hu et al., "Surface Energy Induced Patterning of Polymer Nanostructures for Cancer Diagnosis and Therapy." IEEE Nano 2007 Conference Paper. (2007).

Kaushal et al, Influence of Piperline on Transcutaneous Permeation of Repaglinide in Rats and on Tight Junction Proteins in HaCaT Cells: Unveiling the Mechanisms for Enhanced Permeation; Sci. Pharm. 2009; 77; 877-897.

Kitner, C., "Regulation of embryonic cell adhesion by the calherin cytoplasmic domain", Cell, 1992, 69(2):225-36.

Korhonen et al., "Nitric oxide production and signaling in inflammation", Curr Drug Targets Inflamm Allergy 4(4): 471-9, 2005.

Kumar et al. "Transdermal Drug Delivery System: An Overview." International Journal of Pharmaceutical Sciences Review and Research. 3.2 (2010): 49-54.

Langeler et al., "Norepinephrine and iloprost improve barrier function of human endothelial cellmonolayers: role of cAMP", Am J Physio Cell Physiol, 1991, vol. 260(5), C1052-C1059.

Lim et al., "Human foetal osteoblastic cell response to polymer-demixed nanotopographic interfaces." Journal of the Royal Society Interface. 2.2 (2005): 97-108.

Madara JL, "Regulation of the movement of solutes across light junctions", Annu Rev Physiol, 1998, 60:143-59.

Mahdavi et al., "A biodegradable and biocompatible gecko-inspired tissue adhesive." PNAS. 105.7 (2008): 2307-2312.

Martinez-Palomo et al., "Experimental Modulation of Occluding Junctions in a Cultured Transporting Epithelium", J. Cell Biology, 1980, 87: 736-745.

Meirelles et al., "The effect of chemical and nanotopographical modifications on the early stages of osseointegration." International Journal of Oral and Maxillofacial Implants. 23.4 (2008): 641-647.

Mendelsohn et al., "Inorganic Nanoporous Membranes for Immunoisolated Cell-Based Drug Delivery." Therapeutic Applications of Cell Microencapsulation.

Nagafuchi et al., "Cell binding function of E-cadherin is regulated by the cytoplasmic domain", EMBO Journal, 1988, 7(12): 3679-3684.

Ng et al., "Study of substrate topographical effects on epithelial cell behavior using ethed alpha-particle tracks on PADC films." Nuclear Instruments and Methods in Physics Research Section B: Beam Interactions with Materials and Atoms. 266.14 (2008): 3247-3256.

Ojakian, GK, "Tumor promotor-induced changes in the permeability of epithelial cell tight junctions", Cell, 1981, 23 (1): 95-103.

Orr et al., "Submicrometer and Nanoscale Inorganic Particles Exploit the Actin Machinery to Be Propelled along Microvilli-like structures into Alveolar Cells." American Chemical Society Nano. 1.5 (2007): 463-475.

Ozawa et al., "The cytoplasmic domain of the cell adhesion molecule uvomorulin associates with three independent proteins structurally related in different species", EMBO Journal, 1989, 8(6): 1711-1717.

Ozawa et al., "Uvomorulin-catenin complex formation is regulated by a specific domain in the cytoplasmic region of the cell adhesion molecule", Dev Biology, 1990, 87: 4246-4250.

Ozawa et al., "Uvomorulin-catenin complex formation is regulated by a specific domain in the cytoplastic region of the cell adhesion molecule", Dev Biology, 1990, 87: 4246-4250.

Park et al., "Towards the silicon nanowire-based sensor for intracellular biochemical detection," Biosensors and Sioelectronics, vol. 22, No. 9-10, Apr. 1, 2007, 6 pages.

Peng et al., "Long-Term Small Molecule and Protein Elution from Ti02 Nanotubes." Nano Letters. 9.5 (2009): 1932-1936.

Peng et al., "The effect of Ti02 nanotubes on endothelial function and smooth muscle proliferation." Journal of Biomaterials. 30. (2009): 1268-1272.

Rubin et al., "A Cell Culture Model of the Blood-Brain Barrier", J. Cell Biology, 1991, 115:1725-1735.

Rubin, LL, "Endothelial cells: adhesion and tight junctions". Curr Opin Cell Biol, 1992, 4(5):830-3.

Rutten et al., "Electrical resistance and macromolecular permeability of brain endothelial monolayer cultures", Brain Res, 1987, 425(2):301-10.

Sapra et al., "Transdermal Delivery of Carvedilol Containing Glycyrrhizin and Chitosan as Permeation Enhancers: Biochemical, Biophysical, Microscopic and Pharmacodynamic Evaluation." Drug Delivery, 15.7 (2008): 443-454.

Sapra et al., "Transdermal delivery of carvedilol in rats: probing the percutaneous permeation enhancement mechanism of soybean extract-chitosan mixture." Drug Delivery. 35.10 (2009): 1230-1241.

Sapra et al., "Effect of Asparagus racemous Extract on Transdermal Delivery of Carvedilol: A Mechanistic Study," American Association of Pharmaceutical Scientists PharmSciTech. 10.1 (2009):199.

Schubert et al, "Sliding-induced adhesion of stiff polymer microfibre arrays. IL Microscale behavior", J Royal Society; Jan. 2008, 5, 845-853.

Stappert et al., A short core region of E-cadherin is essential for certain binding and is highly phosphorylated , 1993, Cell Adhes Commun, 2(4):319-27.

Stelzner et at, "Role of cyclic adenosine monophosphate in the induction of endothelial barrier properties", J. Cell Physiol, 1989, 139(1):157-66.

IfEo et al. "The effect of micro and nanotopography on endocytosis in drug and gene delivery systems", Biomaterials, 32 (2011), 9866-9875.

IfHakar et al., "Contractility-Dependent Modulation of Cell Proliferation and Adhesion by Microscale Topographical Cues." Small. 4.9 (2008): 1416-1424.

Valenta et al., "The use of polymers for dermal and transdermal delivery." European Journal of Pharmaceutics and Biopharmaceutics . 58.2 (2004): 279-289.

Verma et al., "Development of Transdermal Drug Dosage Formulation for the Anti-Rheumatic Ayurvedic Medicianal Plants". Ancient Sci. Life, 2007; 11 :66-9.

Wang et al., "Nano patterned PDMS for periodontal ligament fibroblast culture." Surface and Coatings; Technology, 204.4 (2009): 525-530.

Wei et al., "Protein adsorption on materials surfaces with nanotopography." Chinese Science Bulletin. 52.23 (2007): 3169-3173.

(56)         References Cited

OTHER PUBLICATIONS

Wood, M.A. Colloidal lithography and current fabrication techniques producing in-plane nanotopography for biological applications. Journal of the Royal Society Interface. 4.12 (2007): 1-17.

Yao et al., "Nano-Surface Modification on Titanium Implants for Drug Delivery." Materials Research Society. (2007).

Yim et al., "Nanopattern-induced changes in morphology and motility of smooth muscle cells." Journal of Biomaterials. 58.1 (2005).

Supplementary European Search Report dated Sep. 25, 2013, 10 pages.

Communication Pursuant to Article 94(3) EPC dated Mar. 11, 2024, for EP Application 11 830 267-8-1113, 4 pages.

* cited by examiner

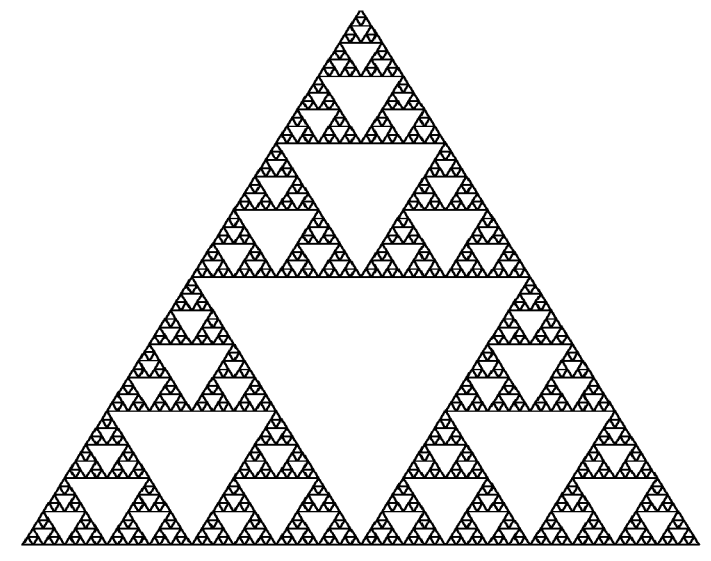
FIG. 6
FIG.7A    FIG.7B
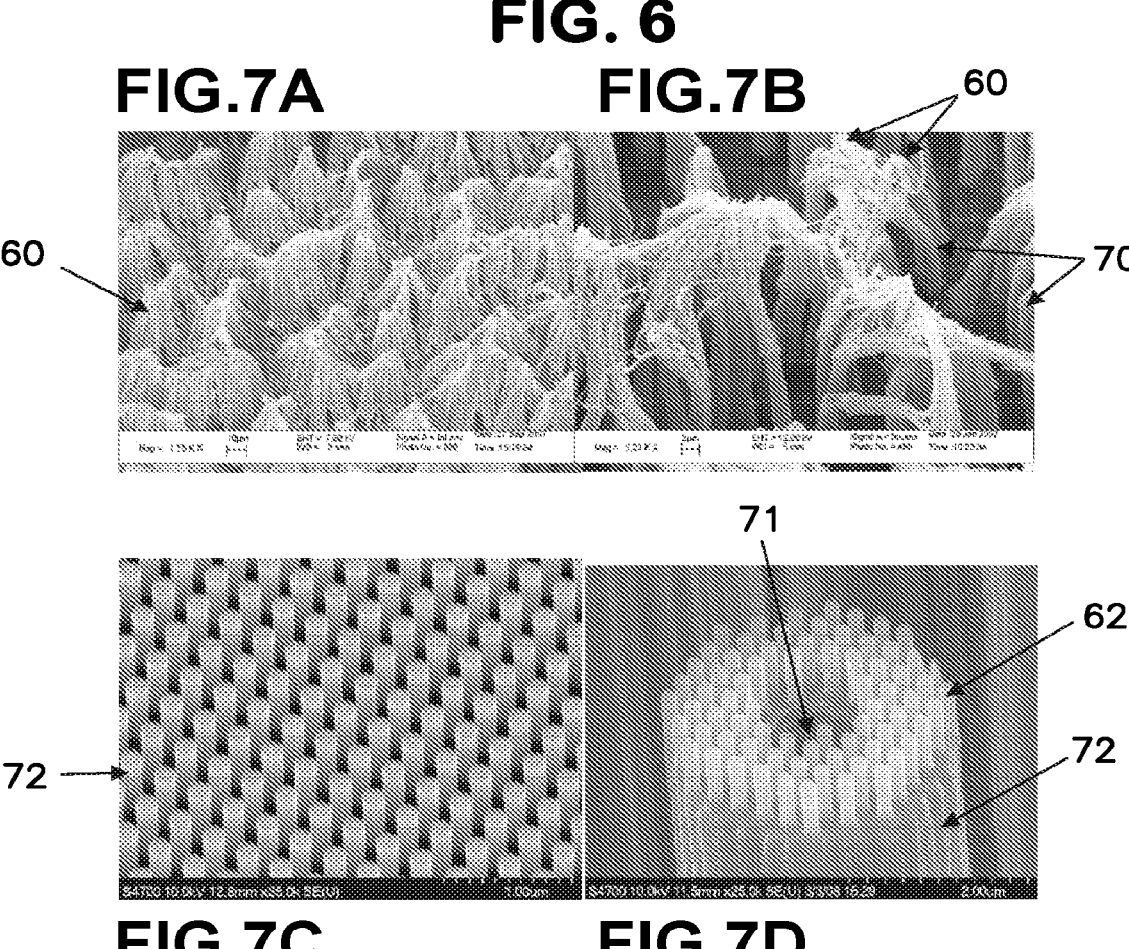
FIG.7C    FIG.7D

*square packing*

*hexagonal packing*

FIG. 24A
DN1
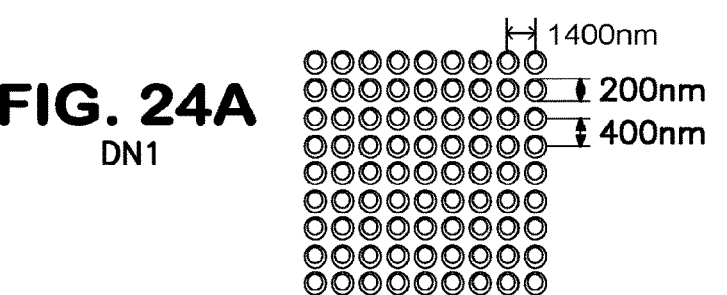 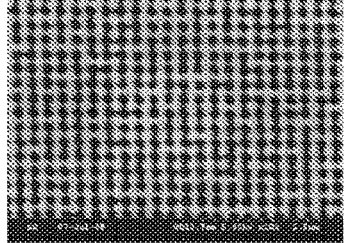
Hole depth=500nm
FIG. 24B
DN2
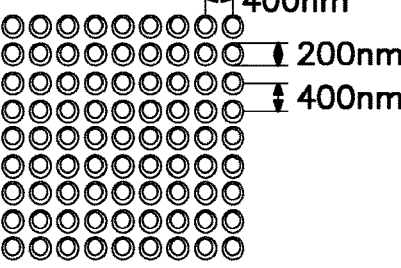 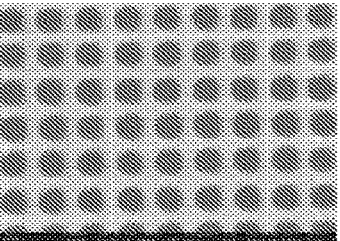
Hole depth=500nm
FIG. 24C
DN3
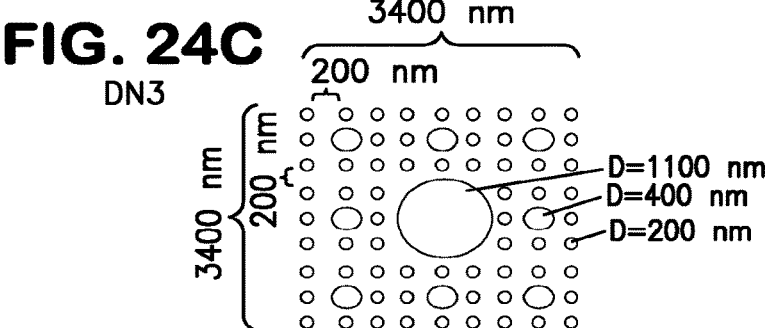 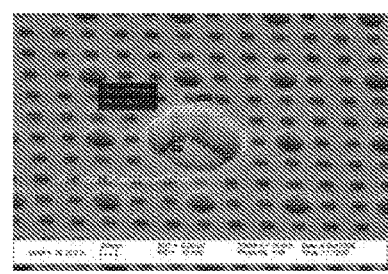
Hole depth=500nm
FIG. 24D
DN4
Hole depth=400−500nm
(Random Variation)

FIG. 24E
NTTAT2
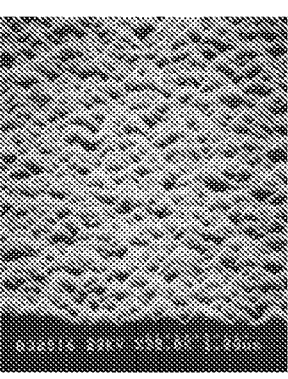
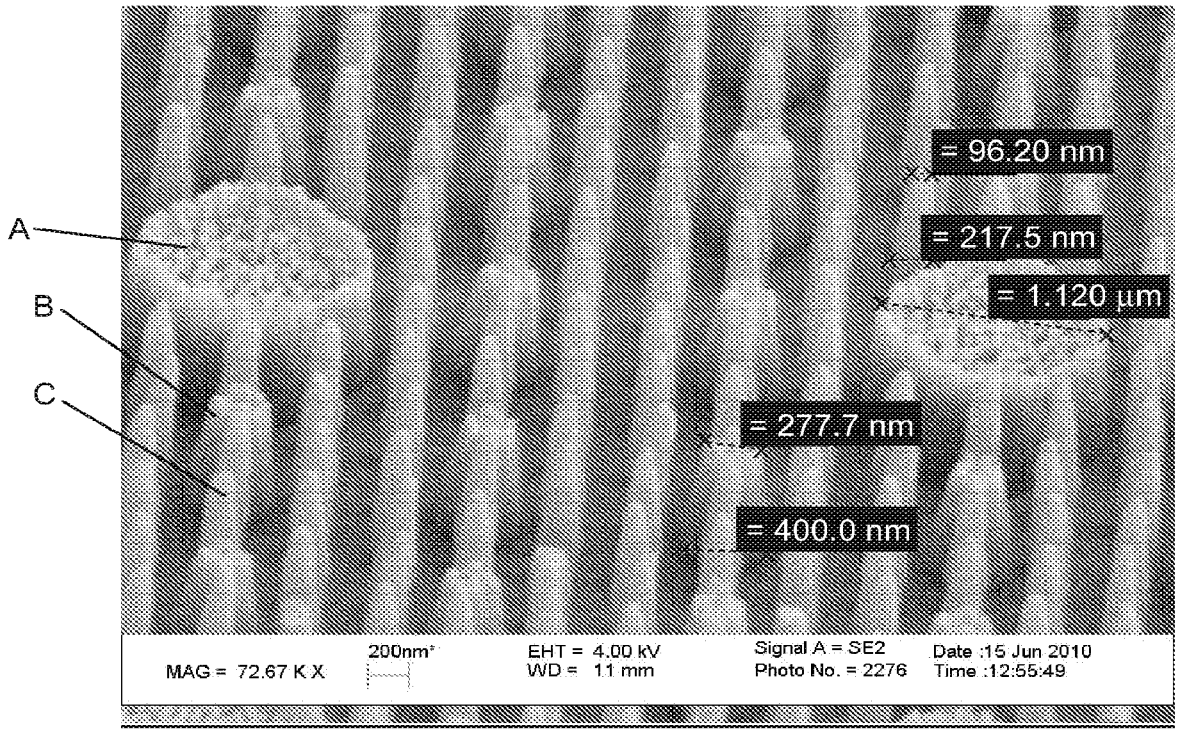
FIG. 25

FIG. 36A
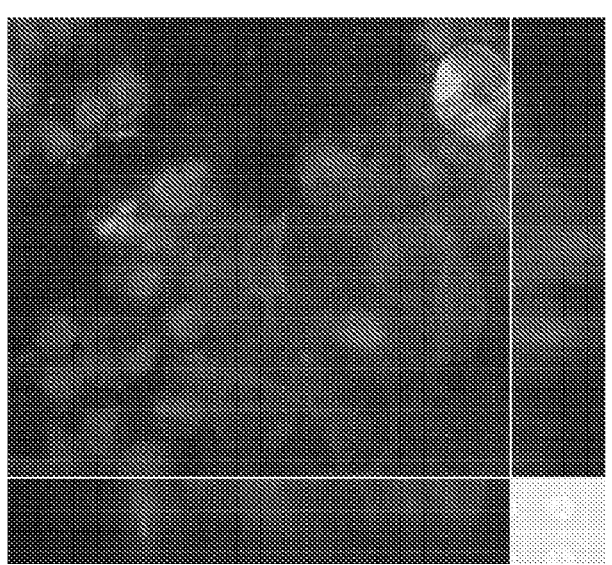
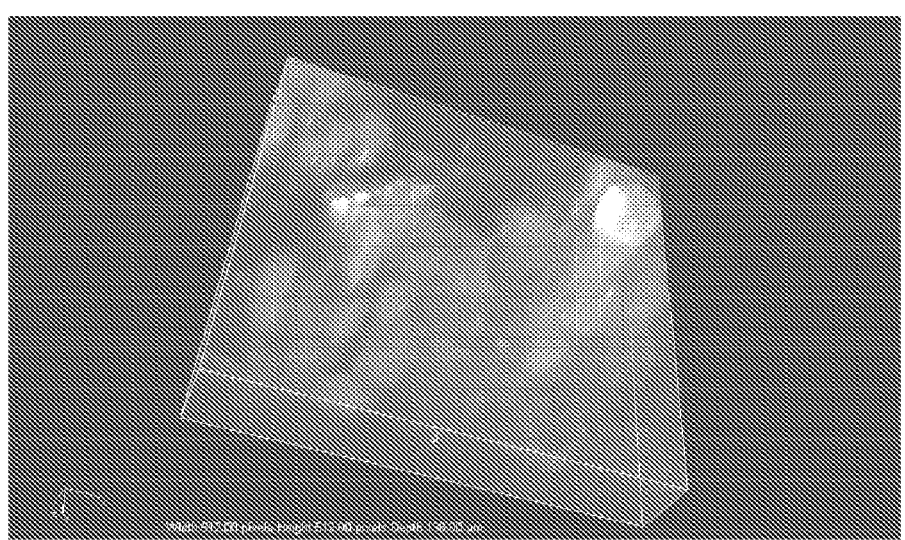
FIG. 36B

FIG. 39A
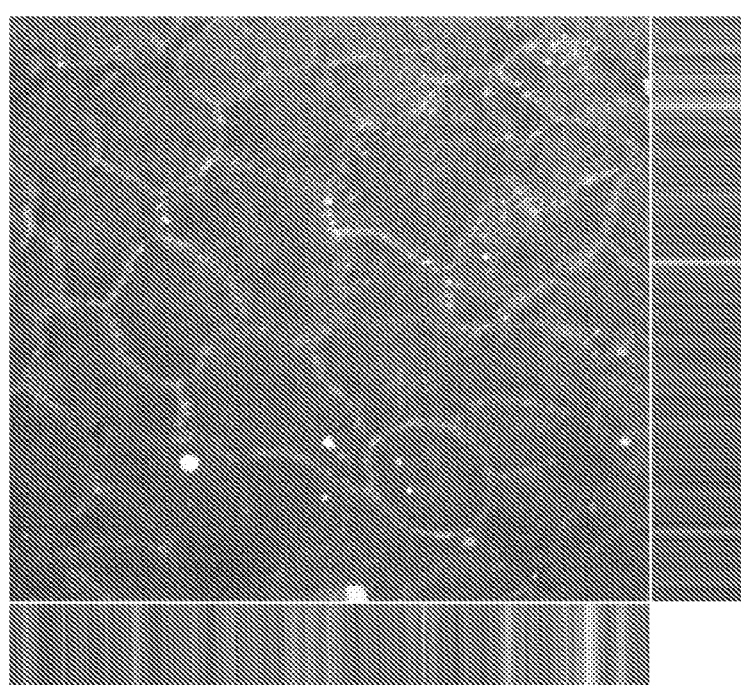
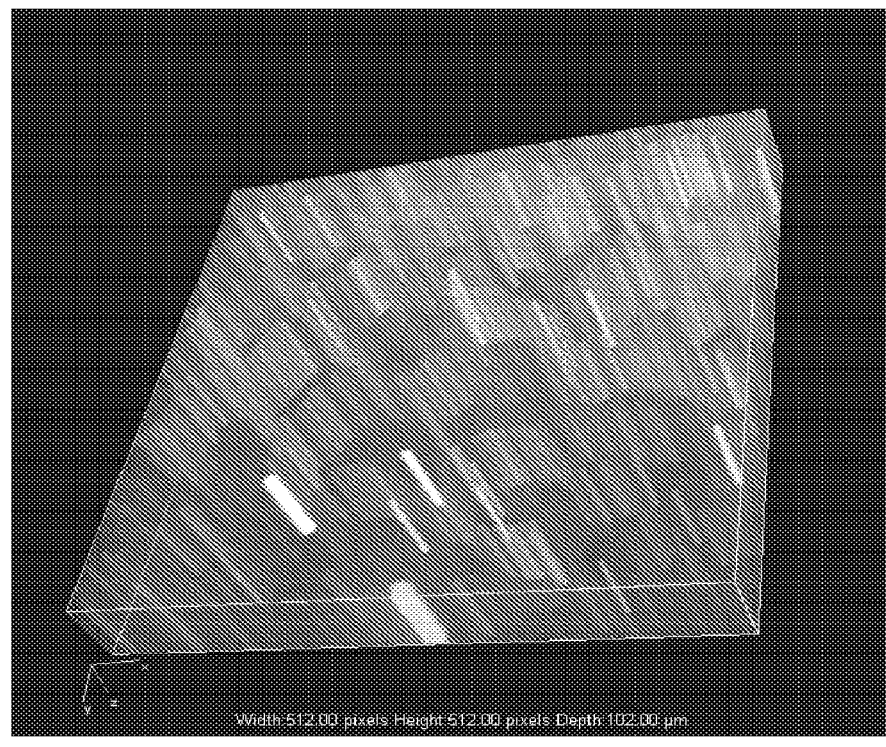
FIG. 39B

FIG. 40A   FIG. 40C   FIG. 40E
Scanning Electron Microscopy
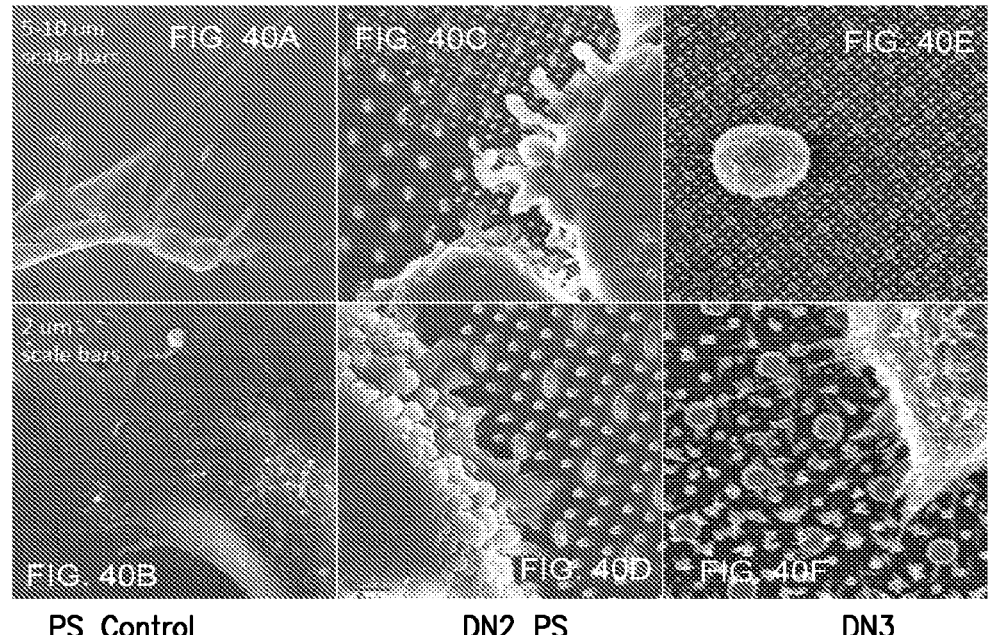
PS Control          DN2 PS          DN3
FIG. 40B   FIG. 40D   FIG. 40F
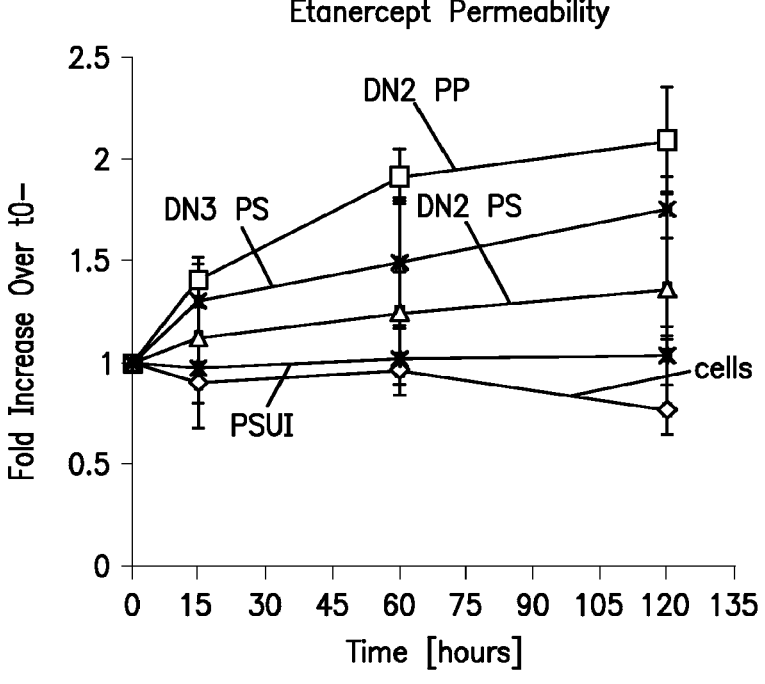
Etanercept Permeability
FIG. 41

Concentration vs. Time Profile in Individual Rabbit

DEVICE FOR DELIVERY OF RHEUMATOID ARTHRITIS MEDICATION

CROSS REFERENCE TO RELATED APPLICATIONS

This nonprovisional application is a divisional of U.S. application Ser. No. 16/896,941, now U.S. U.S. Pat. No. 11,565,098, having a filing date of Jun. 9, 2020, which is a continuation of U.S. application Ser. No. 16/040,714, now U.S. Pat. No. 10,709,884, having a filing date of Jul. 20, 2018, which is a continuation of U.S. application Ser. No. 15/378,097, now U.S. Pat. No. 10,029,082, having a filing date of Dec. 14, 2016, which is a continuation of U.S. application Ser. No. 13/641,501, now U.S. Pat. No. 9,522, 263, having a filing date of Feb. 22, 2013, which is a national stage entry of International Patent Application No. PCT/IB2011/051861 having a filing date of Apr. 27, 2011, which claims priority to U.S. Provisional Patent Application No. 61/328,723 having a filing date of Apr. 28, 2010, U.S. Provisional Patent Application No. 61/411,101 having a filing date of Nov. 8, 2010, and U.S. Provisional Patent Application No. 61/435,973 having a filing date of Jan. 25, 2011, all of which are incorporated herein in their entirety by reference.

BACKGROUND

Rheumatoid arthritis (RA) is a chronic disease that affects millions of people the world over and has no known cure. Though commonly associated with attack on synovial joints, the disease may affect multiple tissues and organs, including the skin, lungs, kidneys, and circulatory system.

Treatment options have advanced through improvements in nutritional therapy, physical therapy, occupational therapy and the like. Pharmacological treatment options have also advanced to include symptom suppression treatment through pain management by use of analgesics and anti-inflammatories (both steroidal and nonsteroidal anti-inflammatory (NSAI) agents), as well as newer disease-modifying antirheumatic drugs (DMARDs), which may also include biological agents (e.g., protein inhibitors such as TNF-α blockers and IL-1 blockers, etc.).

Both systemic drug delivery and targeted drug delivery may be used in treatment of RA. For instance, corticosteroid anti-inflammatories are often delivered directly to a joint via injection, while many DMARDs are systemically delivered orally in an attempt to slow the progression of the disease. Oral delivery and injection have been the primary means of delivery of RA drugs. These delivery methods are problematic, however, as the drugs are delivered with an initial burst of high concentration followed by a steady decline in concentration. Moreover, as many DMARDs exhibit toxicity issues, the initial high burst concentration of drug is severely limited, and as such the trailing concentration following delivery will be extremely low.

Drug delivery devices that provide a route for RA agents to be delivered in an active state at effective, steady concentrations over a period of time would be of great benefit. Many difficulties must be overcome to reach this goal. For instance, the human body has developed many systems to prevent the influx of foreign substances such as enzymatic degradation in the gastrointestinal tract, structural components that prevent absorption across epithelium, hepatic clearance, and immune and foreign body response.

Transdermal devices have been developed for sustained delivery of certain drugs including those for treatment of vertigo and smoking addiction, as well as for contraception agents. In order to be successful, a transdermal device must deliver an agent across the epidermis, which has evolved with a primary function of keeping foreign substances out. The outermost layer of the epidermis, the stratum corneum, has structural stability provided by overlapping corneocytes and crosslinked keratin fibers held together by coreodesmosomes and embedded within a lipid matrix, all of which provides an excellent barrier function. Beneath the stratum corneum is the stratum granulosum, within which tight junctions are formed between keratinocytes. Tight junctions are barrier structures that include a network of transmembrane proteins embedded in adjacent plasma membranes (e.g., claudins, occludin, and junctional adhesion molecules) as well as multiple plaque proteins (e.g., ZO-1, ZO-2, ZO-3, cingulin, symplekin). Tight junctions are found in internal epithelium (e.g., the intestinal epithelium, the blood-brain barrier) as well as in the stratum granulosum of the skin. Beneath both the stratum corneum and the stratum granulosum lies the stratum spinosum. The stratum spinosum includes Langerhans cells, which are dendritic cells that may become fully functioning antigen-presenting cells and may institute an immune response and/or a foreign body response to an invading agent.

Transdermal delivery has been proposed for certain RA drugs. For instance, transdermal patches have been suggested for use with ayurvedic medicinal plants (Verma, et al., *Ancient Sci. Life*, 2007; 11:66-9) and with the analgesic fentanyl (Berliner, et al., *Clin J Pain*, 2007 July-August; 23(6):530-4).

Unfortunately, transdermal delivery methods are presently limited to delivery of low molecular weight agents that have a moderate lipophilicity and no charge. Even upon successful crossing of the natural boundary, problems still exist with regard to maintaining the activity level of delivered agents and avoidance of foreign body and immune response.

The utilization of supplementary methods to facilitate transdermal delivery of active agents has improved this delivery route. For instance, microneedle devices have been found to be useful in transport of material into or across the skin, though the use of a microneedle device has not been found for use with RA drugs. In general, a microneedle device includes an array of needles that may penetrate the stratum corneum of the skin and reach an underlying layer. Examples of microneedle devices have been described in U.S. Pat. No. 6,334,856 to Allen, et al. and U.S. Pat. No. 7,226,439 to Prausnitz, et al., both of which are incorporated herein by reference.

SUMMARY

According to one embodiment, disclosed is a device for delivery of one or more RA drugs across a dermal barrier. For example, the device may include a microneedle and a plurality of nanostructures fabricated on a surface thereof. More specifically, the nanostructures are arranged in a predetermined pattern. The device may also include a rheumatoid arthritis drug in fluid communication with the microneedle.

Methods for delivering a rheumatoid arthritis drug across a dermal barrier are also disclosed. For example, the method may include penetrating the stratum corneum with a microneedle, the microneedle comprising a plurality of nanostructure formed on a surface of the microneedle and arranged in a pattern. The rheumatoid arthritis drug may be in fluid communication with the microneedle. Accordingly, the rheumatoid arthritis drug may be transported across the stratum corneum following penetration of the stratum corneum by the microneedle.

Also disclosed is a method for forming a device for delivery of a rheumatoid arthritis drug across a dermal barrier. The method may include fabricating an array of microneedles, fabricating a pattern of nanostructures on a surface of at least one of the microneedles, and associating a rheumatoid arthritis drug with the microneedles such that the rheumatoid arthritis drug is in fluid communication with the microneedles.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIG. 6 illustrates a Sierpinski triangle fractal.

FIGS. 7A-7D illustrate complex fractal and fractal-like nanotopographies. FIG. 7A and FIG. 7B illustrate a fibrous-like nanotopography. FIG. 7C and FIG. 7D illustrate a complex nanotopography.

FIG. 10A illustrates formation of the microneedles on the resist layer. FIG. 10B illustrates the flow of viscous polymer into the mold cavities. FIG. 10C illustrates removal of the substrate and polymer.

FIG. 11A illustrates the reservoir (bottom view) and the placement of the reservoir superior to the microneedles (top view). FIG. 11B illustrates microneedles 120 contacting a surface 124.

4

Figure 18:
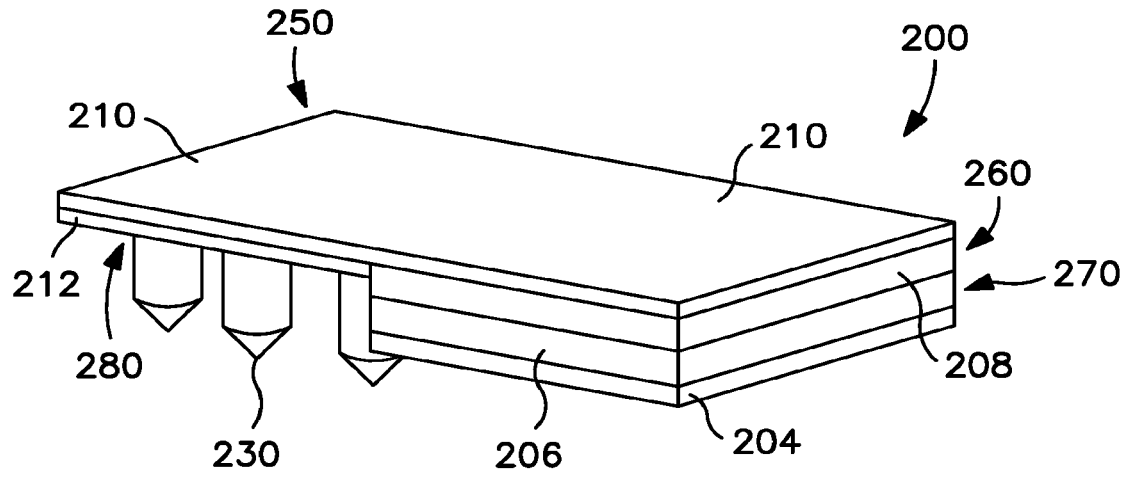
FIG. 18 is a perspective view of another embodiment of a transdermal patch prior to delivery of a drug compound.
Figures 20, 21:
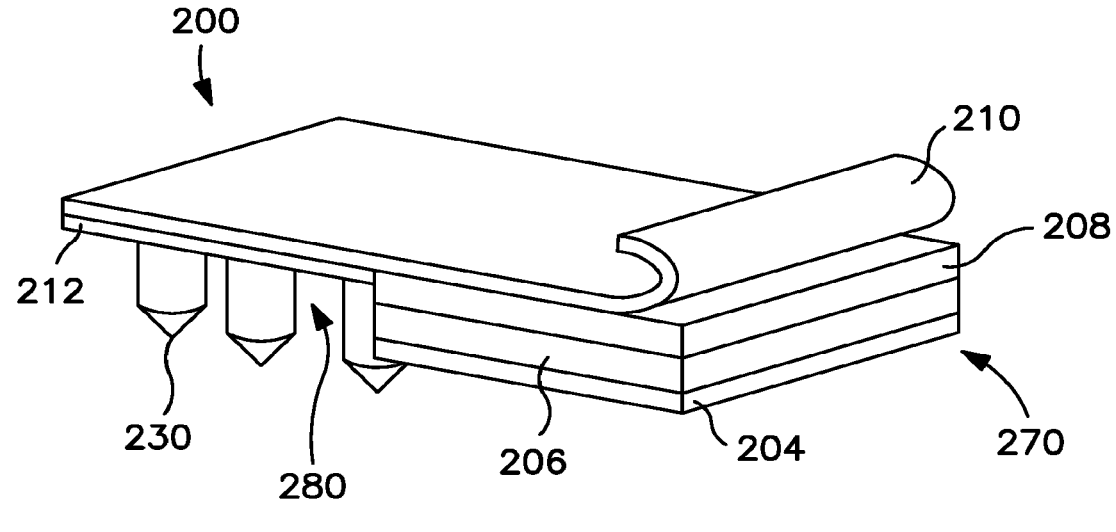

FIG. 20 is a perspective view of the patch of FIG. 18 in which the release member is partially peeled away from the patch.

FIG. 21 is a front view of the patch of FIG. 20.

Figures 22, 23:
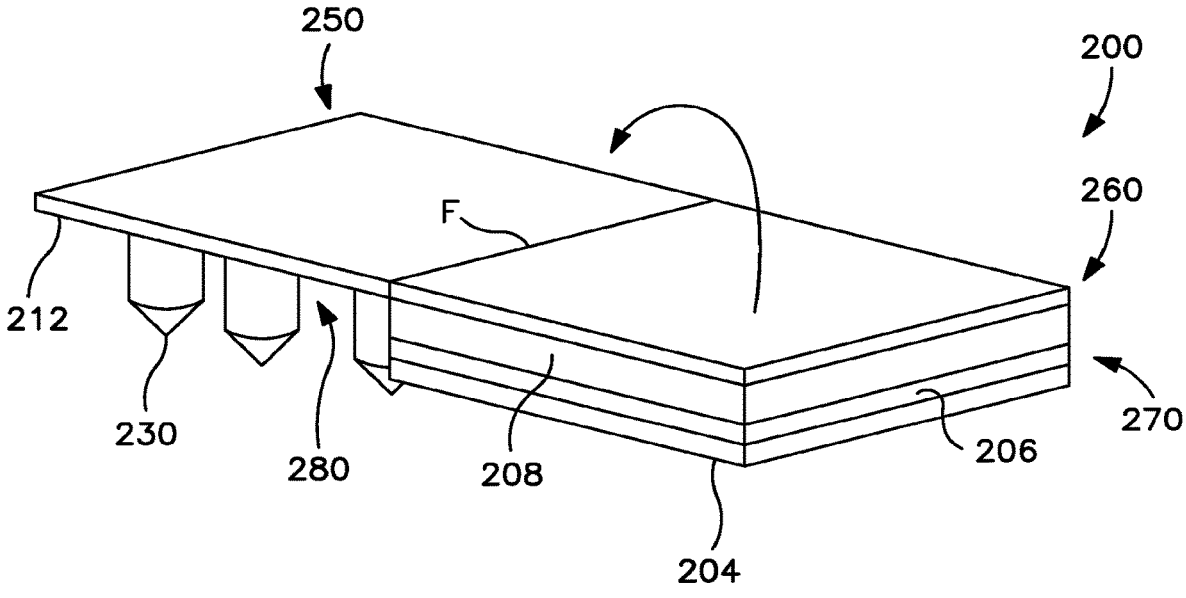

FIG. 22 is a perspective view of the patch of FIG. 18 in which the release member is completely peeled away from the patch.

FIG. 23 is a perspective view of the transdermal patch of FIG. 18 after removal of the release member and during use.

FIGS. 24A-24E illustrate several nanotopography patterns as described herein. FIG. 24A illustrates the nanotopographic pattern from mold DN1. FIG. 24B illustrates the nanotopographic pattern from mold DN2. FIG. 24C illustrates the nanotopographic pattern from mold DN3. FIG. 24D illustrates the nanotopographic pattern from mold DN4. FIG. 24E illustrates the nanotopographic pattern from mold NTTAT2.

FIG. 25 is an SEM of a film including a nanopatterned surface.

Figure 26A:
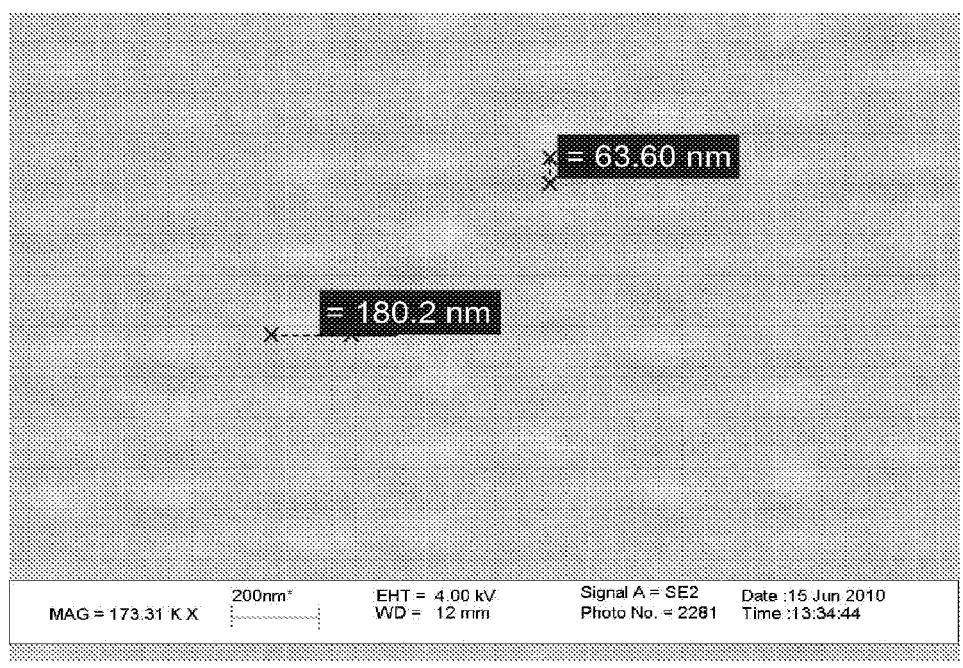
Figure 26B:
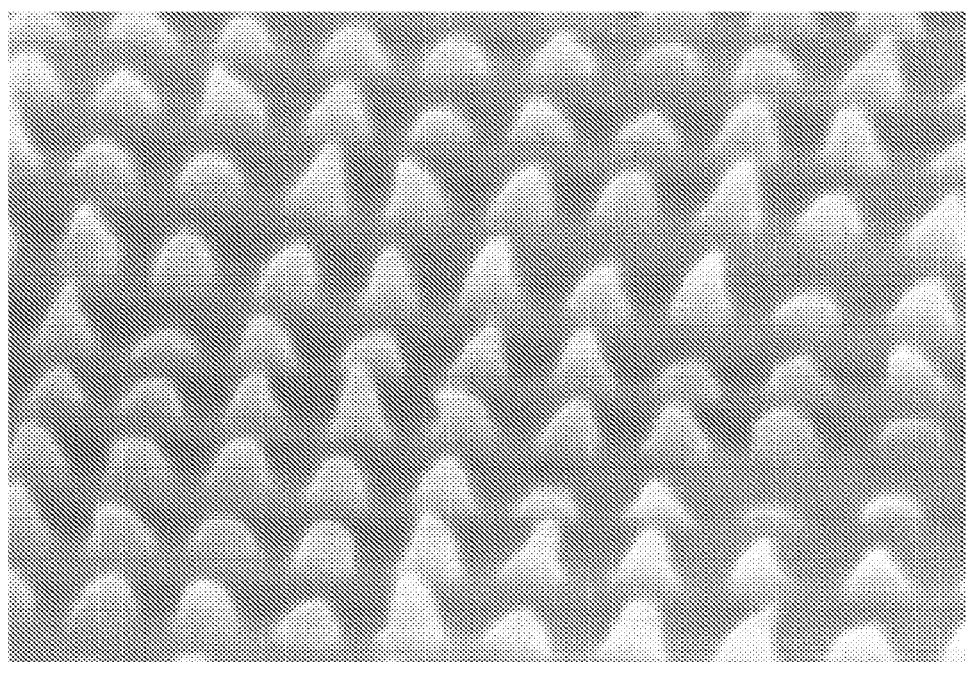

FIGS. 26A and 26B are two SEM of a film including another nanopatterned surface.

Figure 27:
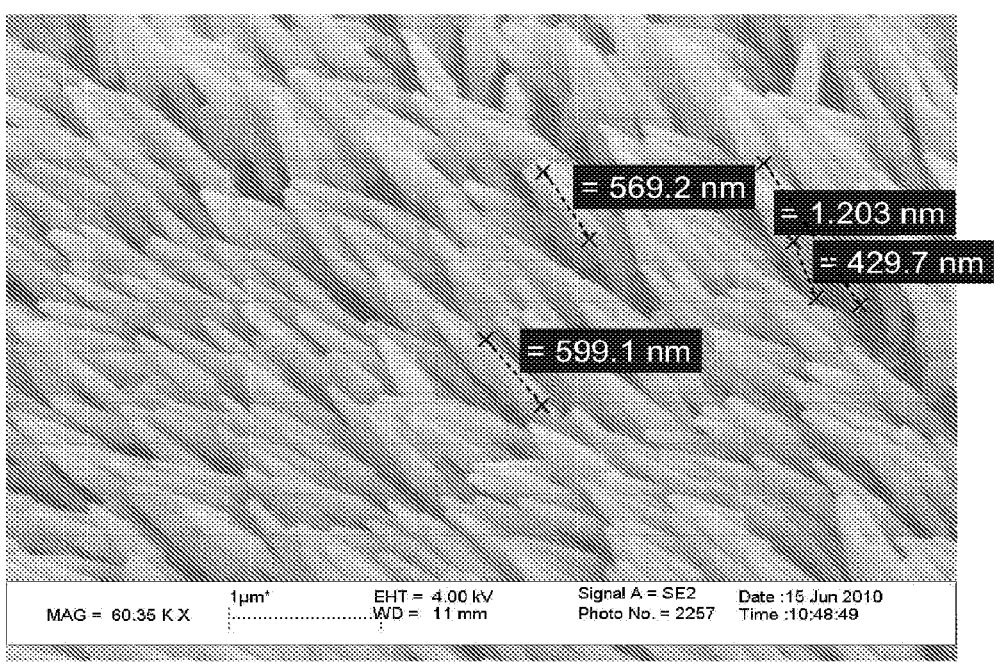

FIG. 27 is an SEM of a film including another nanopatterned surface.

Figure 28:
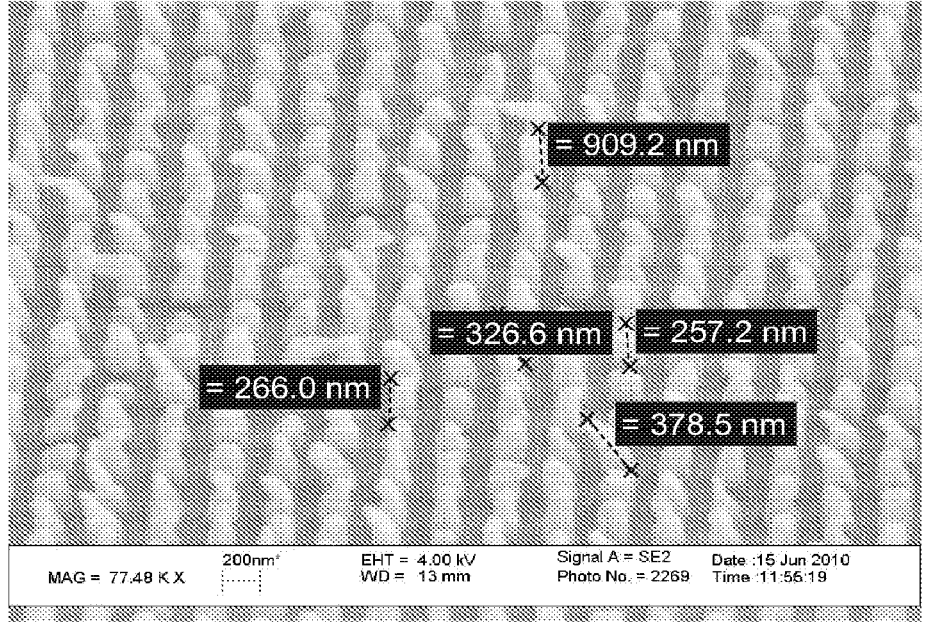

FIG. 28 is an SEM of a film including another nanopatterned surface.

Figure 29:
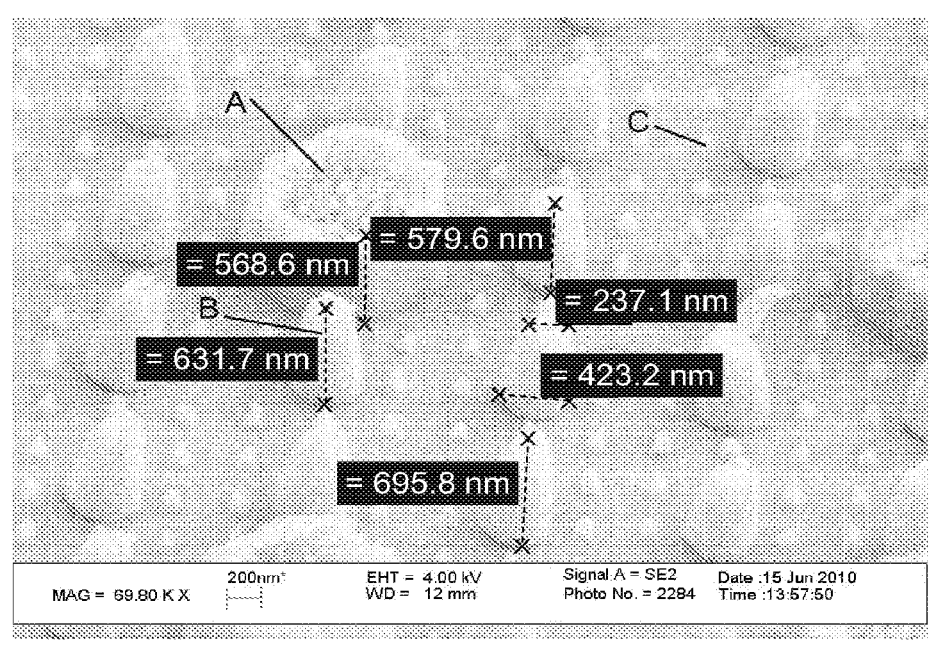

FIG. 29 is an SEM of a film including another nanopatterned surface.

Figure 30:
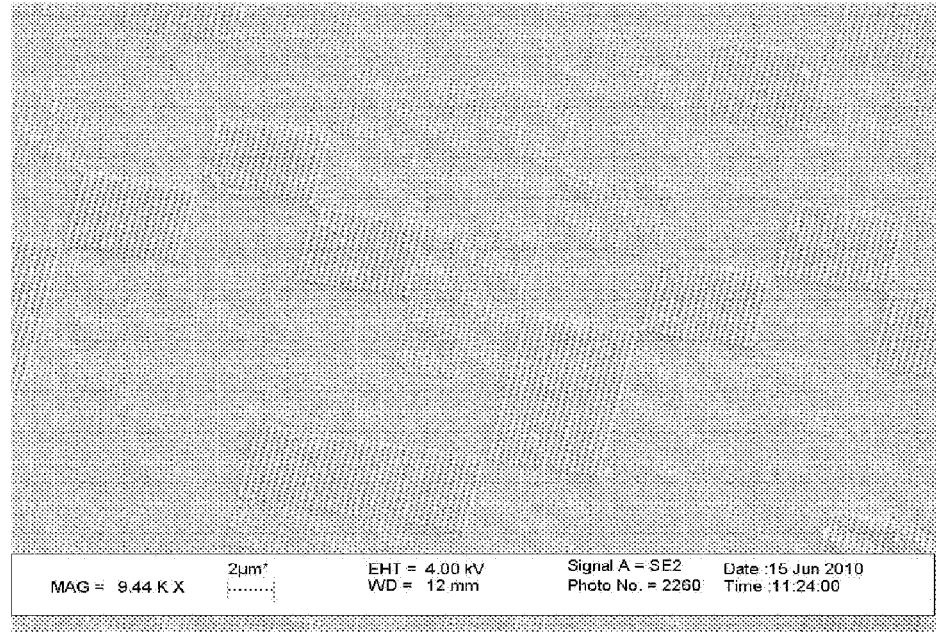

FIG. 30 is an SEM of a film including another nanopatterned surface.

Figure 31:
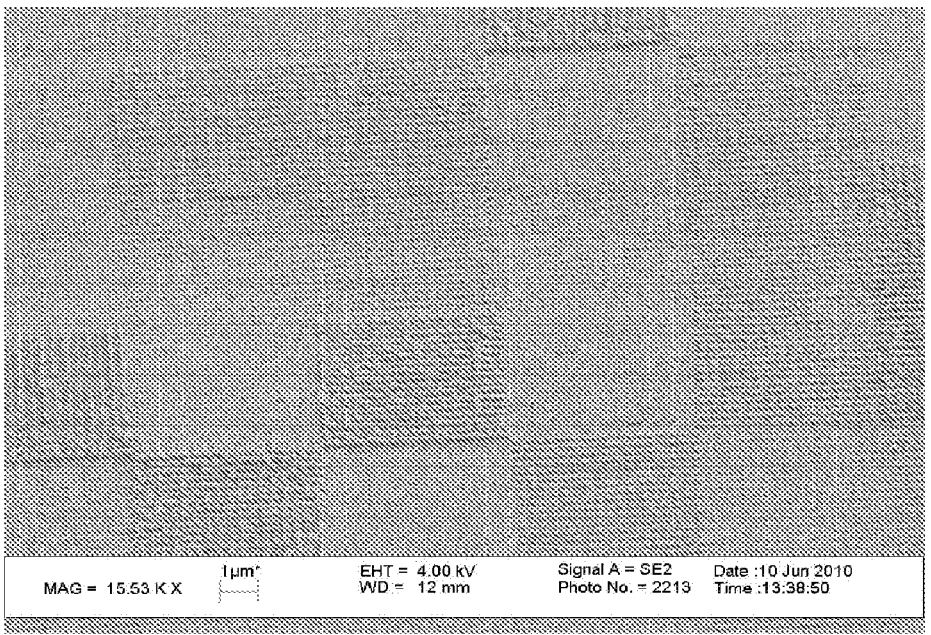

FIG. 31 is an SEM of a film including another nanopatterned surface.

Figure 32:
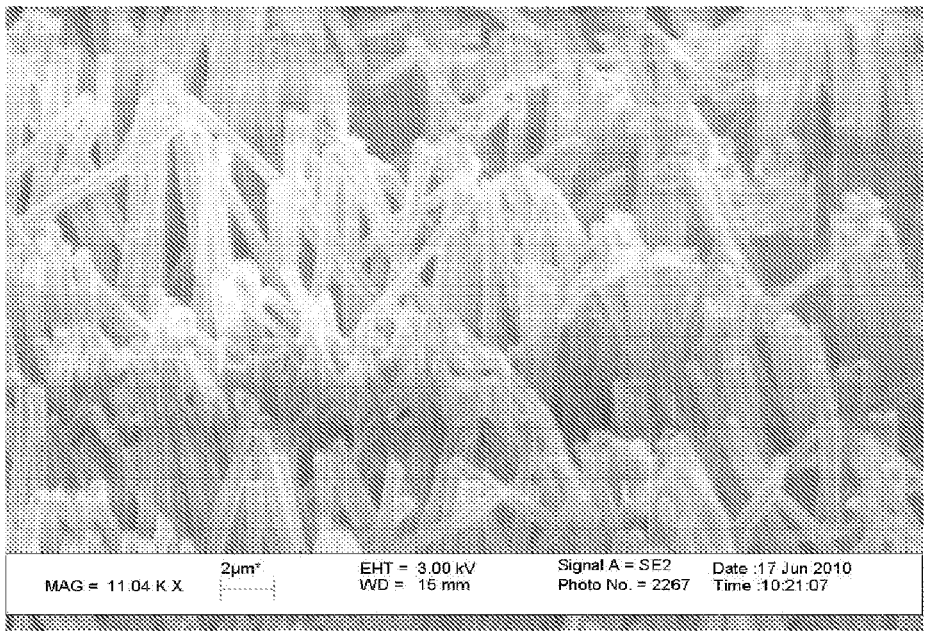

FIG. 32 is an SEM of a film including another nanopatterned surface.

Figure 33:
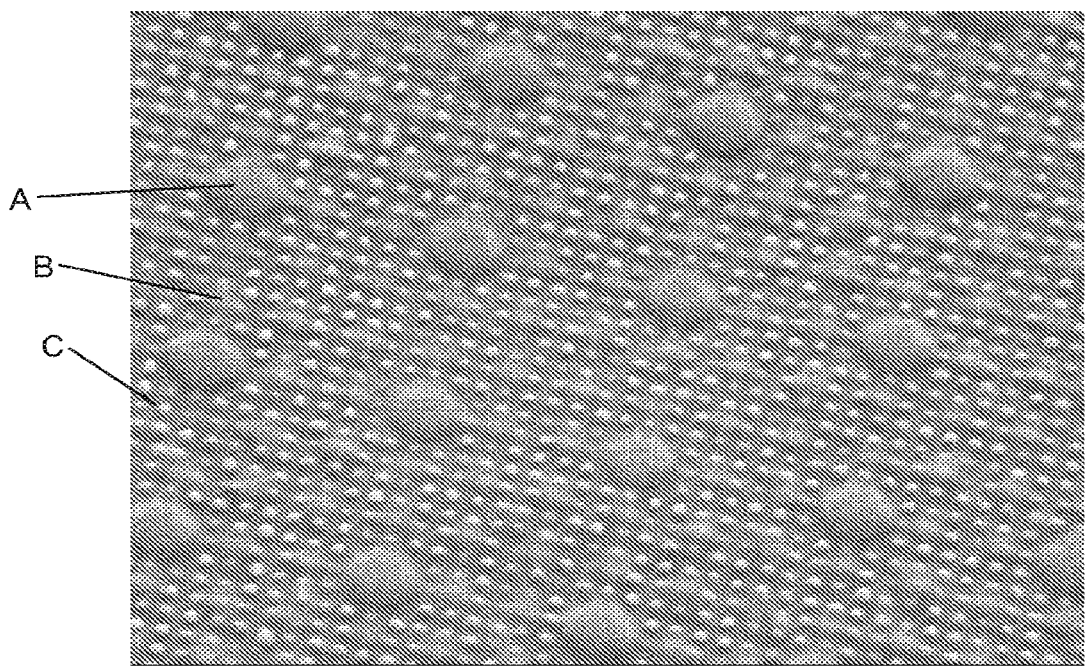

FIG. 33 is an SEM of a film including another nanopatterned surface.

Figure 34:
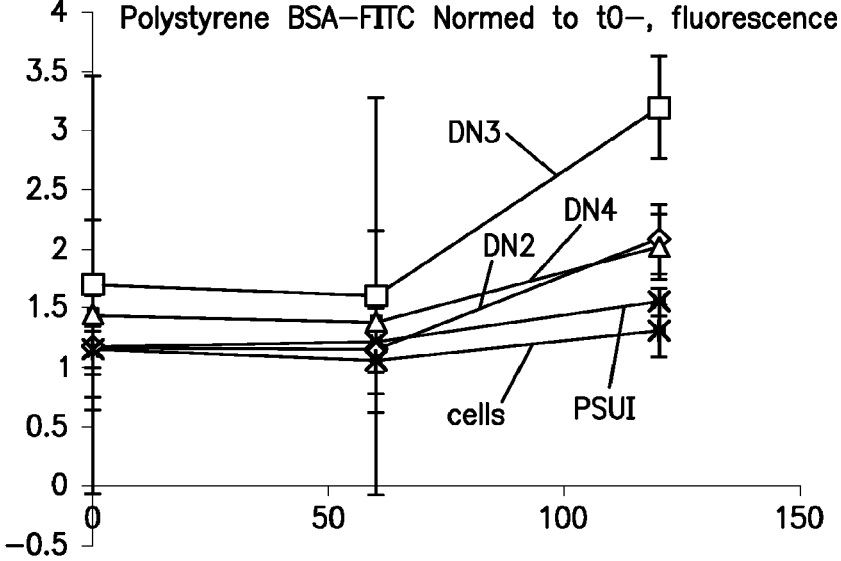

FIG. 34 graphically illustrates the effects on permeability to bovine serum albumin (BSA) in a monolayer of cells on polystyrene films patterned with nanopatterns as described herein.

Figure 35A:
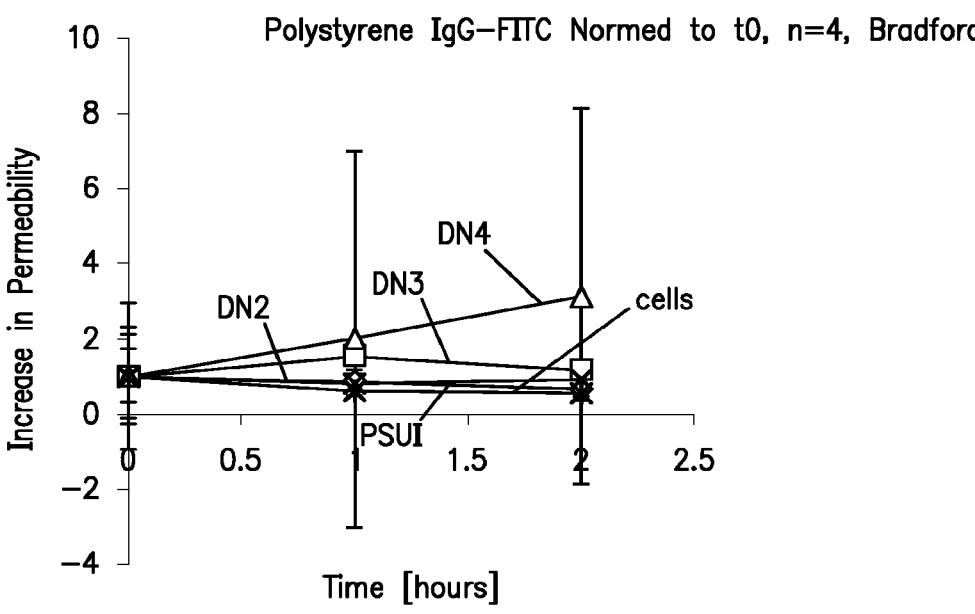
Figure 35B:
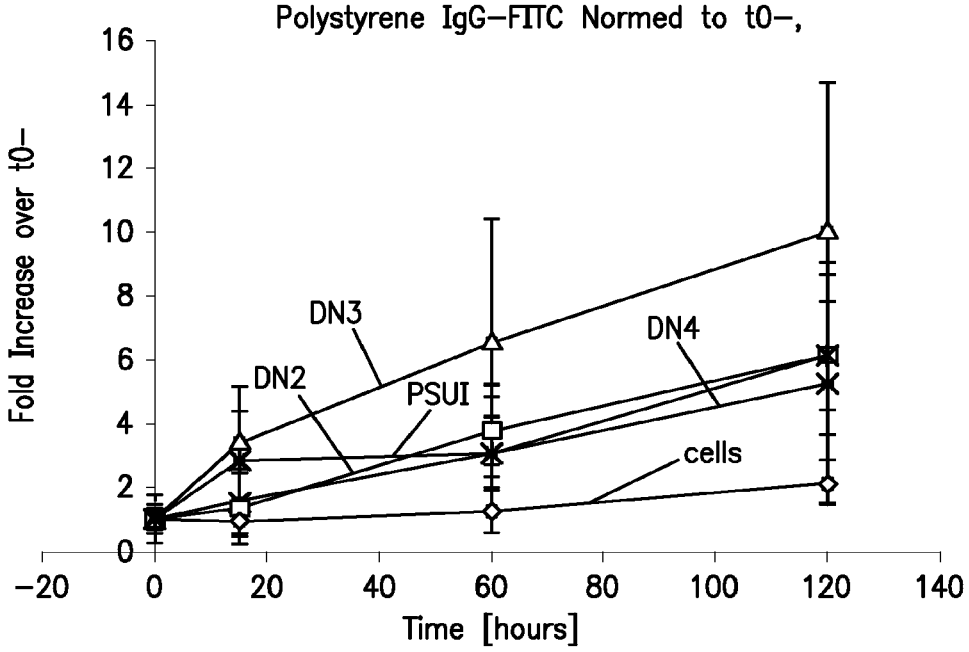

FIGS. 35A and 35B graphically illustrates the effects on permeability to immunoglobulin-G (IgG) in a monolayer of cells on polystyrene films patterned with nanopatterns as described herein.

FIGS. 36A and 36B are 3D live/dead flourescein staining images showing paracellular and transcellular transport of IgG across a monolayer of cells on a polystyrene patterned surface as described herein.

Figure 37:
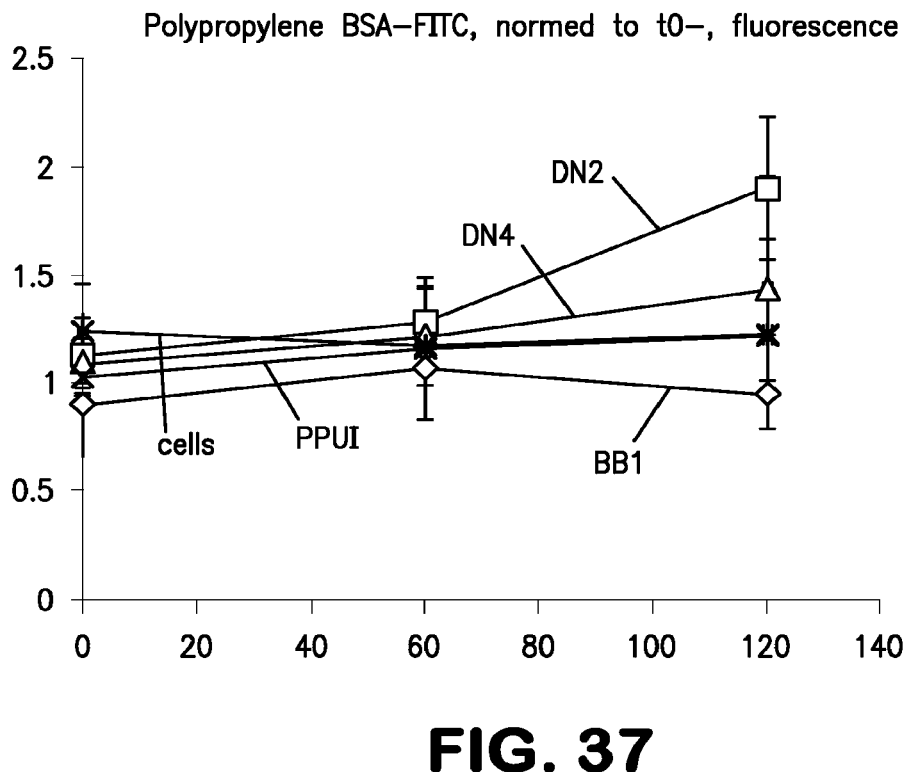

FIG. 37 graphically illustrates the effects on permeability to BSA in a monolayer of cells on polypropylene films patterned with nanopatterns as described herein.

Figure 38:
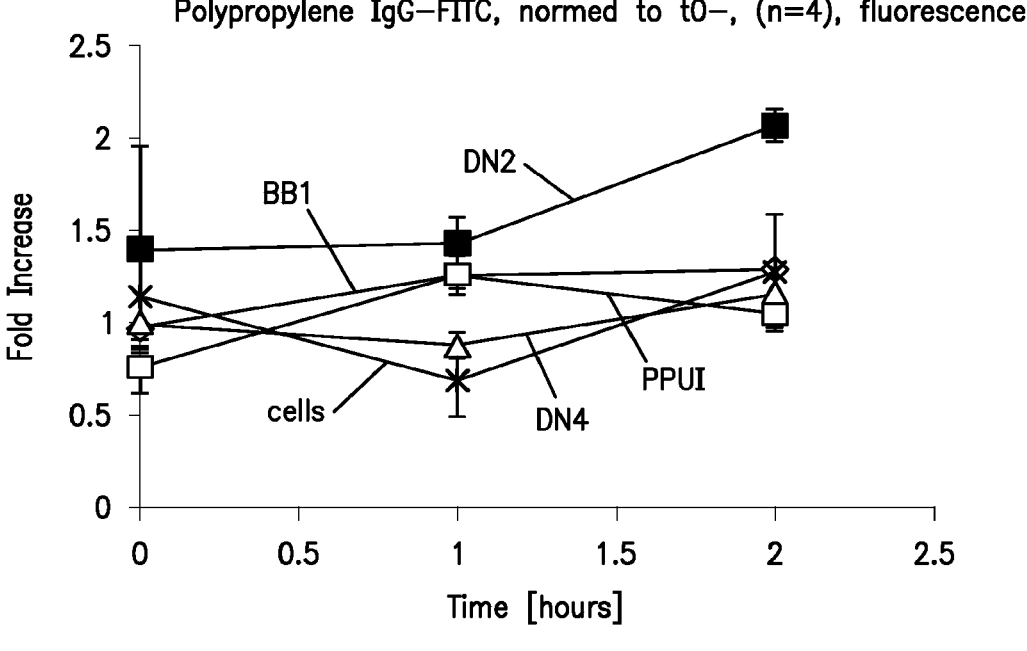

FIG. 38 graphically illustrates the effects on permeability to IgG in a monolayer of cells on polypropylene films patterned with nanopatterns as described herein.

FIGS. 39A and 39B are 3D live/dead flourescein staining images showing paracellular transport of IgG across a monolayer of cells on a polypropylene patterned surface as described herein.

FIGS. 40A-40F are scanning electron microscopy (SEM) images of cells cultured on nanopatterned surfaces as described herein. FIGS. 40A and 40B illustrate Caco-2 cells on a flat polystyrene control film. FIGS. 40C and 40D illustrate Caco-2 cells on a polystyrene film patterned with a DN2 pattern. FIGS. 40E and 40F illustrate Caco-2 cells on a polystyrene film patterned with a DN3 pattern.

FIG. 41 illustrates the effects on permeability to etanercept in a monolayer of cells on polypropylene or polystyrene films patterns with nanopatterns as described herein.

Figure 42:
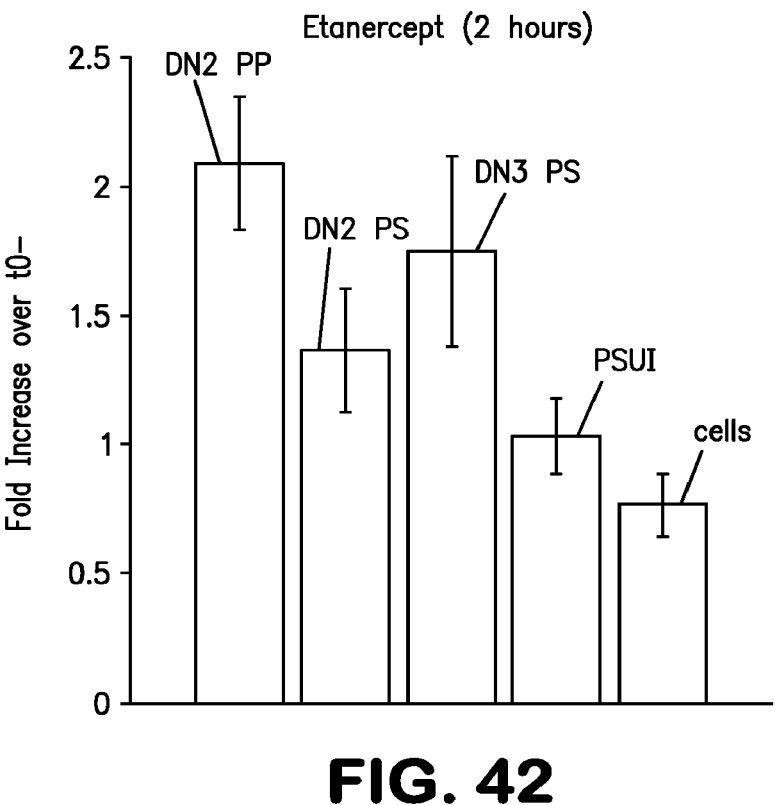

FIG. 42 illustrates the increase in permeability to etanercept of a cellular layer following two hours of contact with a polypropylene or polystyrene films patterns with nanopatterns as described herein.

Figure 43:
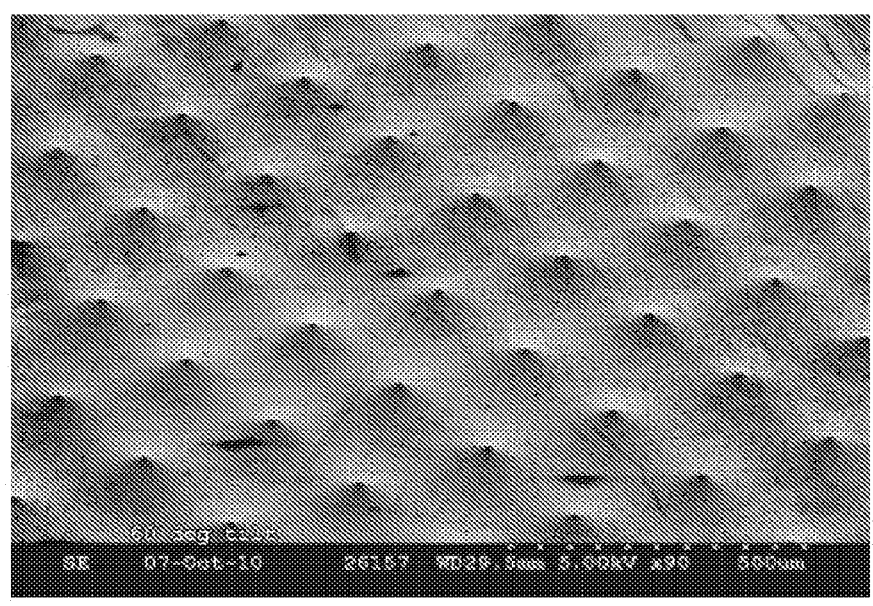

FIG. 43 is an array of microneedles including a surface layer defining a pattern of nanostructures thereon.

Figure 44:
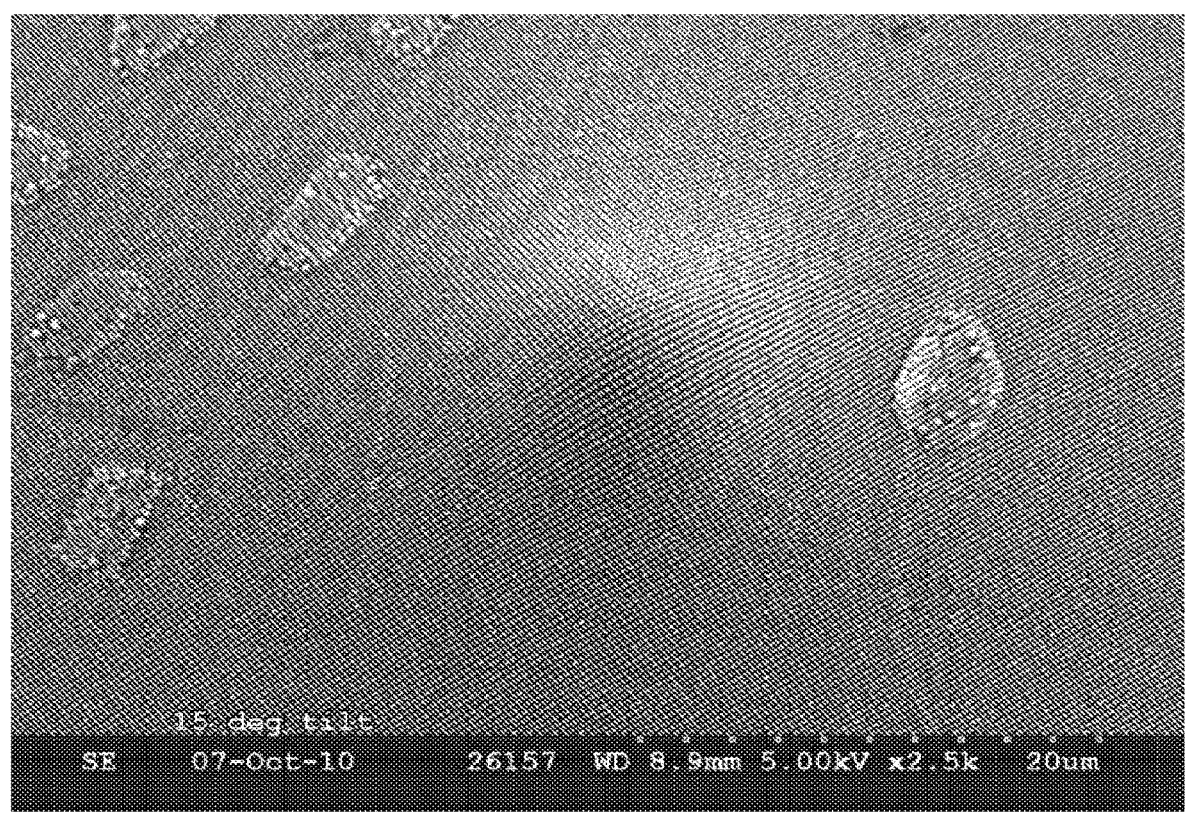

FIG. 44 is a single microneedle of the array of FIG. 43.

Figure 45:
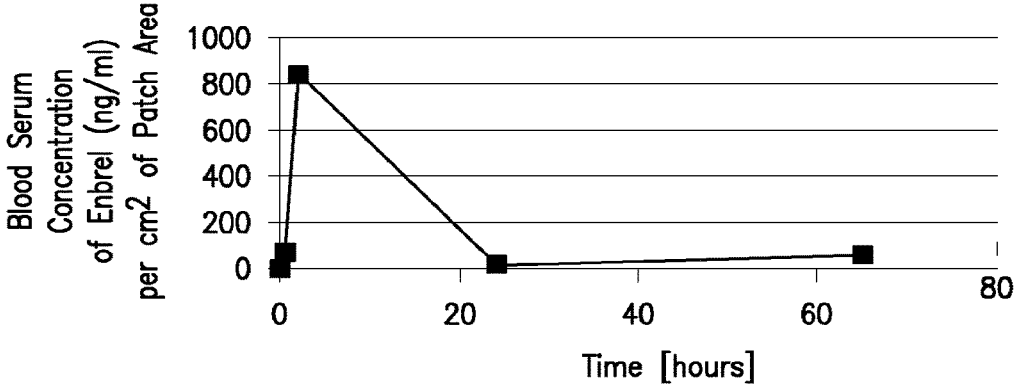

FIG. 45 graphically illustrates the PK profile of a protein therapeutic delivered with a device as described herein.

Figure 46A:
Figure 46B:
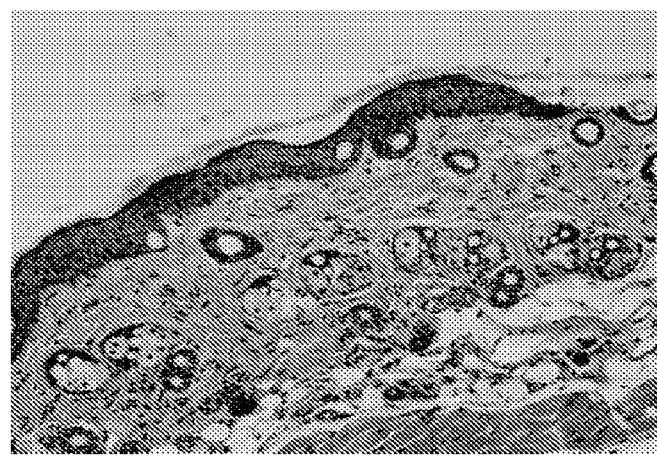

FIGS. 46A and 46B are cross sectional images of skin following transdermal delivery of a protein therapeutic across the skin. FIG. 46A is a cross section of skin that was in contact with a transdermal device defining a nanotopography thereon, and FIG. 46B is a cross section of skin that was in contact with a transdermal device including no pattern of nanotopography formed thereon.

Figure 47:
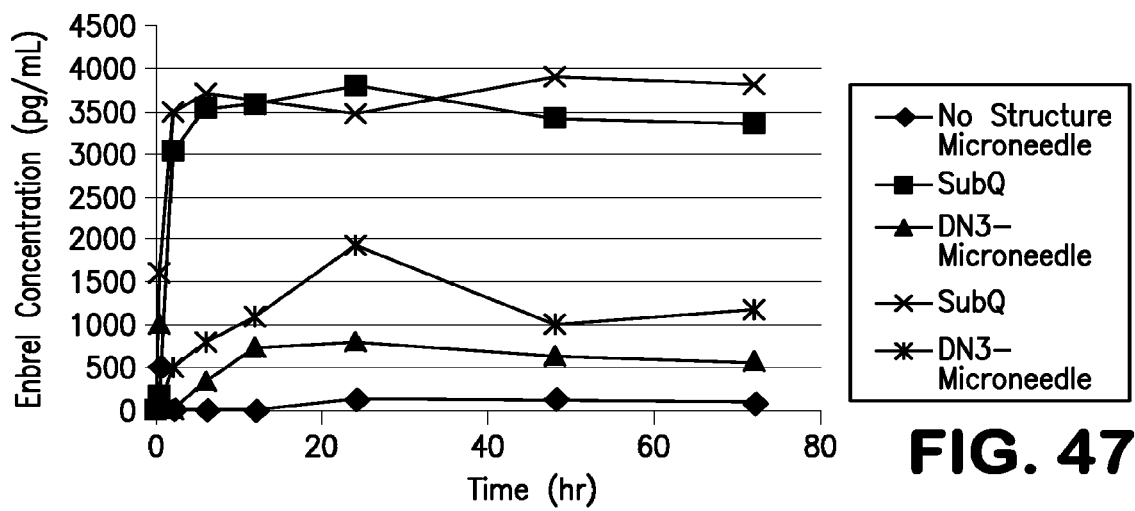

FIG. 47 graphically illustrates the blood serum concentration of a protein therapeutic delivered with a device as described herein.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

In general, a device for delivery of compounds useful in treatment of RA is disclosed. More specifically, the device includes a plurality of microneedles at a surface and a pattern of structures fabricated on the microneedles. At least a portion of the structures are fabricated on a nanometer scale. The device is also associated with one or more RA drugs, for instance in a layer of the device or in a reservoir that is in fluid communication with the surface that includes the microneedles.

The device may include and deliver symptom suppression compounds, such as analgesics and anti-inflammatory drugs, as well as DMARD compounds, including biological DMARDs. While not wishing to be bound to any particular theory, it is understood that the nanometer-scale structures fabricated on the surface of the device improve deliver of the compounds across the dermal barrier. Through utilization of the device, RA drugs may be delivered at a steady concentration over a sustained period. The device may prevent the initial burst of concentration common when utilizing previously known methods for delivery of RA drugs, including oral delivery and injection.

RA drugs as may be incorporated in the device may include, without limitation, one or more analgesics, anti-inflammatories, DMARDs, herbal-based drugs, and combinations thereof. Specific compounds can, of course, fall under one or more of the general categories described herein. For instance, many compounds function as both an analgesic and an anti-inflammatory; herbal-based drugs may likewise function as a DMARD as well as an anti-inflammatory. Moreover, multiple compounds that may fall under a single category may be incorporated in the device. For instance, the device may include multiple analgesics, such as acetaminophen with codeine, acetaminophen with hydrocodone (vicodin), and so forth.

Examples of analgesics and/or NSAIDs as may be incorporated in the devices include analgesics available over the counter (OTC) at relatively low dosages including acetamide (acetaminophen or paracetamol), acetylsalicylic acid (aspirin), ibuprofen, ketoprofen, naproxen and naproxen sodium, and the like. Prescription analgesics and/or anti-inflammatories as may be incorporated in the device may include, without limitation, OTC analgesics at concentrations requiring a prescription, celecoxib, sulindac, oxaprozin, salsalate, piroxicam, indomethacin, etodolac, meloxicam, nabumetone, keteroloc and ketorolac tromethamine, tolmetin, diclofenac, diproqualone, and diflunisal. Narcotic analgesics may include codeine, hydrocodone, oxycodone, fentanyl, and propoxyphene.

The device may include one or more steroidal anti-inflammatory compounds, primarily glucocorticoids, including, without limitation, cortisone, dexamethasone, prednisolone, prednisone, hydrocortisone, tramcinolone, and methylprednisolone, betamethasone, and aldosterone.

DMARDs as may be included in the device may encompass both small molecule drugs and biological agents. DMARDs may be chemically synthesized or may be produced through genetic engineering processes (e.g., recombinant techniques).

Chemically synthesized DMARDs encompassed herein include, without limitation, azathioprine, cyclosporine (ciclosporin, cyclosporine A), D-penicillamine, gold salts (e.g., auranofin, Na-aurothiomalate (Myocrism), chloroquine, hydroxychloroquine, leflunomide, methotrexate, minocycline, sulphasalazine (sulfasalazine), and cyclophosphamide. Biological DMARDs include, without limitation, TNF-α blockers such as etanercept (Enbrel®), infliximab (Remicade®), adalimumab (Humira®), certolizamab pego (Cimzia®) and golumumab (Simponi™); IL-1 blockers such as anakinra (Kineret®); monoclonal antibodies against B cells including rituximab (Rituxan®); T cell costimulation blockers such as abatacept (Orencia®), and IL-6 blockers such as tocilizumab (RoActemra®, Actemra®); a calcineurin inhibitor such as tacrolimus (Prograf®).

The device may incorporate one or more herbal-based or other naturally-derived drugs. For instance, Ayurvedic compounds such as boswellic acid (extract of *Boswellia serrata*) and curcumin (curcuminoids from *Curcuma longa*), as well as other naturally derived compounds such as glucosamine sulfate (produced by hydrolysis of crustacean exoskeletons or fermentation of a grain) may be incorporated in the device.

The device may incorporate multiple RA drugs. For instance, the device may include a combination of DMARDs in addition to an analgesic and/or an anti-inflammatory drug. Common combinations of DMARDs include, for example, methotrexate in combination with hydroxychloroquine, methotrexate in combination with sulfasalazine, sulfasalazine in combination with hydroxychloroquine, and all three of these DMARDs together, i.e., hydroxychloroquine, methotrexate, and sulfasalazine.

The devices may beneficially incorporate large and/or small molecular weight compounds. For instance, in the past, transdermal delivery of protein therapeutics has proven problematic due to the natural barriers of the skin. While not wishing to be bound to any particular theory, the presence of the nanotopography of a microneedle of the device may beneficially interact with cells and ECM of the dermal barrier and improve efficiency of delivery and uptake of protein therapeutics. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. For instance, the presence of the device in or near the stratum granulosum may open tight junctions and allow and/or improve paracellular transport of high molecular weight agents. As utilized herein, the term high molecular weight agents generally refers to agents defining a molecular weight greater than about 400 Da, greater than about 10 kDa, greater than about 20 kDa, or greater than about 100 kDa).

Even when considering delivery of smaller molecular weight RA drugs, the device may provide increased efficiency and improved uptake due to interaction of the device with components of the dermal connective tissue and accompanying decrease in foreign body response and improvement in localized chemical potential of the area. In addition, the device may deliver the RA drugs at a steady concentration over a sustained period, which may be beneficial.

The device includes, in addition to the RA drug(s), microneedles upon which have been fabricated a plurality of nano-sized structures. As utilized herein, the term 'fabricated' generally refers to a structure that has been specifically designed, engineered, and/or constructed so as to exist at a surface of the device and is not to be equated with a surface feature that is merely an incidental product of a device formation process. Thus, there will be a predetermined pattern of nanostructures on the surface of the microneedles.

During use, the device, and specifically, the nano-sized structures on the surface of the microneedles, may interact with the dermal tissue and components thereof. This interaction may regulate or modulate (i.e., changing) intracellular and/or intercellular signal transduction associated with cell/cell interactions, endocytosis, inflammatory response, and so forth. For instance, through interaction between the nano-topography on a surface and surrounding biological materials or structures, the device may regulate and/or modulate membrane potential, membrane proteins, and/or intercellular junctions (e.g., tight junctions, gap junctions, and/or desmasomes). This may encourage the transdermal delivery of the RA drugs. Moreover, the RA drugs may be delivered across the dermal barrier without instigating a foreign body or immune response.

Due to improved interaction with surrounding biological components, the devices may facilitate improved uptake of a delivered agent. For example, the pharmacokinetic (PK) profile (i.e., the profile of absorption through the epithelial membranes) of a protein therapeutic may be enhanced through utilization of a device including a pattern of nano-topography. By way of example, a protein therapeutic having a molecular weight of over 100 kDa, for instance between about 20 kDa and about 200 kDa, or about 150 kDa, may be delivered transdermally via a patch defining a nanotopography thereon. In one embodiment, a patch may be utilized to deliver a single dose of the protein therapeutic, for instance between about 200 and about 500 µL, or about 250 µL. Following attachment of the transdermal patch to the skin, the recipient may exhibit a PK profile that reflects a rapid rise in blood serum concentration up to between about 500 and about 1000 nanograms therapeutic per milliliter per square centimeter of patch area, for instance between about 750 and about 850 nanograms therapeutic per milliliter per square centimeter patch area, within about 1 to about 4 hours of administration. This initial rapid rise in blood serum level, which reflects rapid uptake of the therapeutic across the dermal barrier, may be followed by a less rapid decline of blood serum concentration over between about 20 and about 30 hours, for instance over about 24 hours, down to a negligible blood serum concentration of the therapeutic. Moreover, the rapid uptake of the delivered therapeutic may be accompanied by little or no inflammation. Specifically, in addition to promoting improved delivery of an agent across a transdermal barrier, the devices may also limit foreign body response and other undesirable reactions, such as inflammation. Use of previously known devices, such as transdermal patches with no nanotopography defined at the skin contacting surface, often led to local areas of inflammation and irritation.

Moreover, and without wishing to be bound to any particular theory, it is believed that through interaction with a nanopatterned substrate, individual cells may up- or down-regulate the production of certain cytokines, including certain chemokines. Through that alteration in expression profile, cellular response to a drug delivery device may be minimized. For example, inflammation and/or foreign body response may be minimized through upregulation of one or more anti-inflammatory cytokines and/or down-regulation of one or more pro-inflammatory cytokines. Many cytokines have been characterized according to effect on inflammation. Pro-inflammatory cytokines that may demonstrate altered expression profiles when expressing cells are affected by the presence of a device including a nanotopography fabricated thereon may include, without limitation, IL-1α, IL-1β, IL-2, IL-6, IL-8, IL-10, IL-12, IL16, MIG, MIP-1α, MIP-1β, KC, MCP-1, TNF-α, GM-CSI, VEGF, and the like. Anti-inflammatory cytokines that may demonstrate an altered expression profile may include, without limitation, IL-1ra, IL-4, IL-10, IL-13, and the like. Cytokines associated with foreign body response that may demonstrate an altered expression profile may include, without limitation, IL-4, IL-10, IL-13, and so forth.

The device may be constructed from a variety of materials, including metals, ceramics, semiconductors, organics, polymers, etc., as well as composites thereof. By way of example, pharmaceutical grade stainless steel, titanium, nickel, iron, gold, tin, chromium, copper, alloys of these or other metals, silicon, silicon dioxide, and polymers may be utilized in forming a device. Typically, the microneedles of the device are formed of a biocompatible material that is capable of carrying a pattern of nano-sized structures on a surface. The term "biocompatible" generally refers to a material that does not substantially adversely affect the cells or tissues in the area where the device is to be delivered. It is also intended that the materials do not cause any substantially medically undesirable effect in any other areas of a living subject utilizing a device. Biocompatible materials may be synthetic or natural. Some examples of suitable biocompatible materials, which are also biodegradable, include polymers of hydroxy acids such as lactic acid and glycolic acid polylactide, polyglycolide, polylactide-co-glycolide, copolymers with PEG, polyanhydrides, poly(ortho) esters, polyurethanes, poly(butyric acid), poly(valeric acid), and poly(lactide-co-caprolactone). Other suitable materials may include, without limitation, polycarbonate, polymethacrylic acid, ethylenevinyl acetate, polytetrafluorethylene, and polyesters. The various components of a device (e.g., the microneedles, the base, the top, drug contacting areas, etc.) may be non-porous or porous in nature, may be homogeneous or heterogeneous across the device with regard to materials, geometry, solidity, and so forth, and may have a rigid fixed or a semi-fixed shape.

Figure 1:
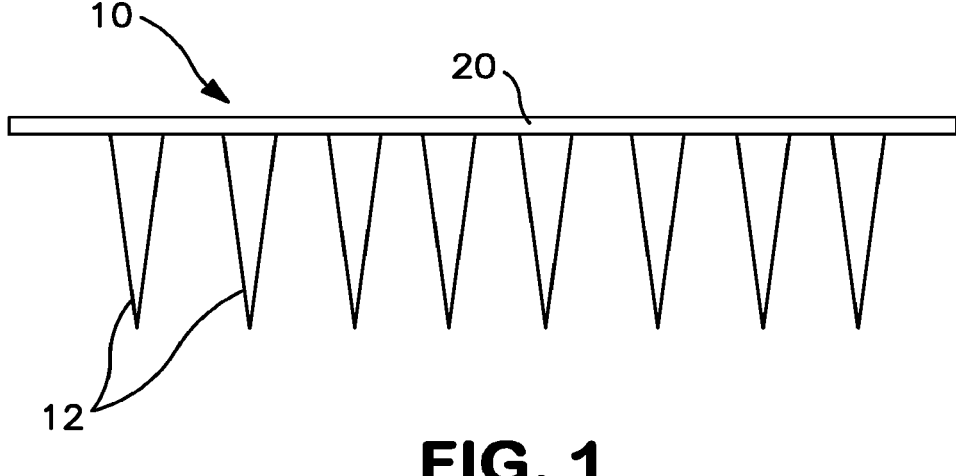
FIG. 1 illustrates one embodiment of a microneedle device.
Figure 2:
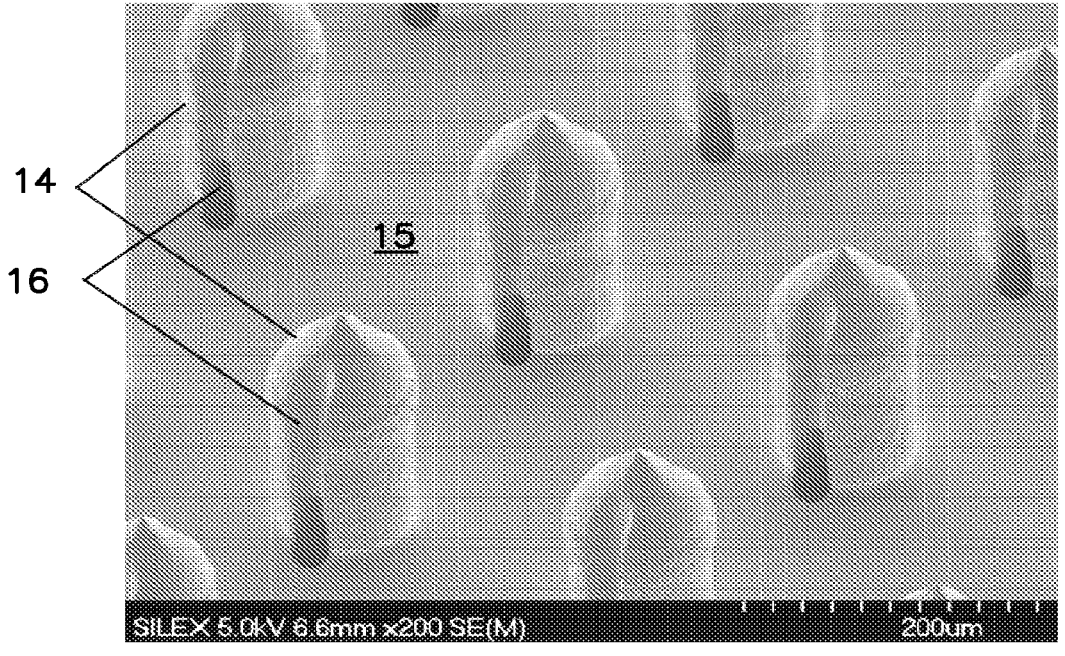
FIG. 2 illustrates another embodiment of a microneedle device.

FIG. 1 illustrates a typical microneedle transdermal device 10. As may be seen, the device includes an array of individual needles 12; each formed to a size and shape so as to penetrate all or a portion of the dermal barrier without breakage of the individual microneedles. Microneedles may be solid, as in FIG. 1, porous, or may include a hollow portion. A microneedle may include a hollow portion, e.g., an annular bore that may extend throughout all or a portion of the needle, extending parallel to the direction of the needle or branching or exiting at a side of the needle, as appropriate. For example, FIG. 2 illustrates an array of microneedles 14 each including a channel 16 in a side of the needle as maybe utilized for delivery of an RA drug to a subdermal location. For instance, a channel 16 may be in at least partial alignment with an aperture in base 15 so as to form a junction between the aperture and channel 16 allowing the passage of a substance through the channel 16.

The dimensions of the channel 16, when present, may be specifically selected to induce capillary flow of a drug compound. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel 16. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio can be determined from the average dimensions.

It should be understood that the number of microneedles shown in the figures is for illustrative purposes only. The actual number of microneedles used in a microneedle assembly may, for example, range from about 500 to about 10,000, in some embodiments from about 2,000 to about 8,000, and in some embodiments, from about 4,000 to about 6,000.

An individual microneedle may have a straight or a tapered shaft. In one embodiment, the diameter of a microneedle may be greatest at the base end of the microneedle and taper to a point at the end distal the base. A microneedle may also be fabricated to have a shaft that includes both a straight (untapered) portion and a tapered portion.

A microneedle may be formed with a shaft that is circular or non-circular in cross-section. For example, the cross-section of a microneedle may be polygonal (e.g. star-shaped, square, triangular), oblong, or any other shape. The shaft may have one or more bores and/or channels.

The size of individual needles may be optimized depending upon the desired targeting depth, the strength requirements of the needle to avoid breakage in a particular tissue type, etc. For instance, the cross-sectional dimension of a transdermal microneedle may be between about 10 nanometers (nm) and 1 millimeter (mm), or between about 1 micrometer (μm) and about 200 micrometers, or between about 10 micrometers and about 100 micrometers. The outer diameter may be between about 10 micrometers and about 100 micrometers and the inner diameter of a hollow needle may be between about 3 micrometers and about 80 micrometers. The tip typically has a radius that is less than or equal to about 1 micrometer.

The length of a microneedle will generally depend upon the desired application. For instance, a microneedle may be between about 1 micrometer and about 1 millimeter in length, for instance about 500 micrometers or less, or between about 10 micrometers and about 500 micrometers, or between about 30 micrometers and about 200 micrometers.

An array of microneedles need not include microneedles that are all identical to one another. An array may include a mixture of microneedles having various lengths, outer diameters, inner diameters, cross-sectional shapes, nanostructured surfaces, and/or spacings between the microneedles. For example, the microneedles may be spaced apart in a uniform manner, such as in a rectangular or square grid or in concentric circles. The spacing may depend on numerous factors, including height and width of the microneedles, as well as the amount and type of any substance that is intended to be moved through the microneedles. While a variety of arrangements of microneedles is useful, a particularly useful arrangement of microneedles is a "tip-to-tip" spacing between microneedles of about 50 micrometers or more, in some embodiments about 100 to about 800 micrometers, and in some embodiments, from about 200 to about 600 micrometers.

Referring again to FIG. 1, microneedles may be held on a substrate 20 (i.e., attached to or unitary with a substrate) such that they are oriented perpendicular or at an angle to the substrate. In one embodiment, the microneedles may be oriented perpendicular to the substrate and a larger density of microneedles per unit area of substrate may be provided. However, an array of microneedles may include a mixture of microneedle orientations, heights, materials, or other parameters. The substrate 20 may be constructed from a rigid or flexible sheet of metal, ceramic, plastic or other material. The substrate 20 may vary in thickness to meet the needs of the device, such as about 1000 micrometers or less, in some embodiments from about 1 to about 500 micrometers, and in some embodiments, from about 10 to about 200 micrometers.

Figure 3:
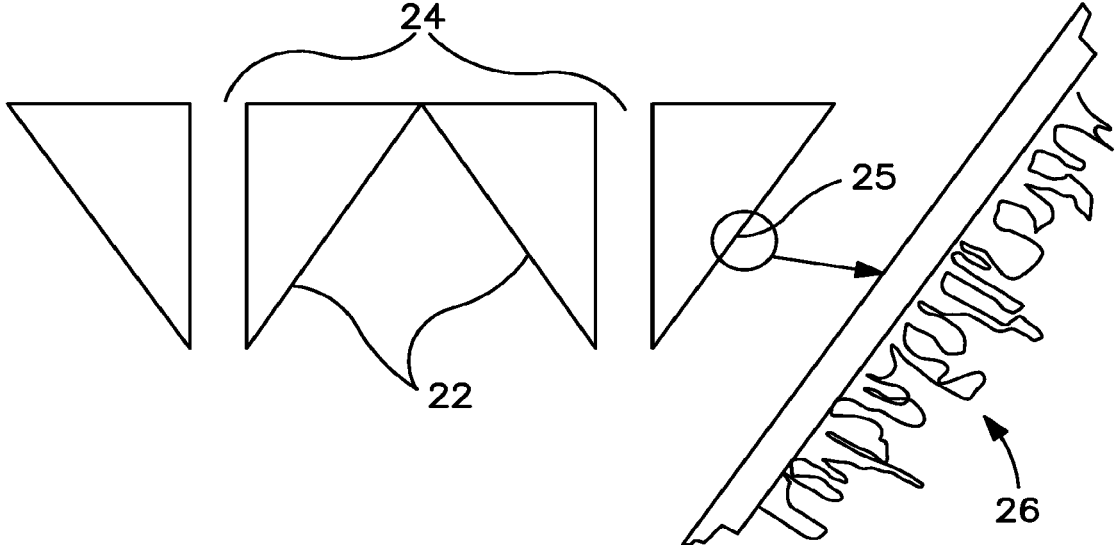
FIG. 3 illustrates one embodiment of a microneedle including a surface that defines a nanotopography that may interact with an extracellular matrix (ECM).

The device may define a nanotopography on the surface of a microneedle in a random or organized pattern. The device may additionally define a nanotopography on the substrate surface from which the microneedle extends, though this is not a requirement. FIG. 3 schematically illustrates the ends of two representative microneedles 22. In this particular embodiment, microneedles 22 define a central bore 24 as may be used for delivery of an RA drug via the microneedles 22. The surface 25 of microneedle 22 may define nanotopography 26. In this particular embodiment, the nanotopography 26 defines a random pattern on the surface 25 of the microneedle 22.

A microneedle may include a plurality of identical structures formed on a surface or may include different structures formed of various sizes, shapes and combinations thereof. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles. In one embodiment, structures may vary with regard to size and/or shape and may form a complex nanotopography. For example, a complex nanotopography may define a fractal or fractal-like geometry.

As utilized herein, the term "fractal" generally refers to a geometric or physical structure having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal. For example, it may be regular and relatively easily described in traditional Euclidean geometric language, whereas a fractal may not.

By way of example, a microneedle surface defining a complex nanotopography may include structures of the same general shape (e.g., pillars) and the pillars may be formed to different scales of measurement (e.g., nano-scale pillars as well as micro-scale pillars). In another embodiment, a microneedle may include at a surface structures that vary in both scale size and shape or that vary only in shape while formed to the same nano-sized scale. Additionally, structures may be formed in an organized array or in a random distribution. In general, at least a portion of the structures may be nanostructures formed on a nano-sized scale, e.g., defining a cross-sectional dimension of less than about 500 nanometers, for instance less than about 400 nanometers, less than about 250 nanometers, or less than about 100 nanometers. The cross sectional dimension of the nanostructures may generally be greater than about 5 nanometers, for instance greater than about 10 nanometers, or greater than about 20 nanometers. For example, the nanostructures may define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

Figure 4:
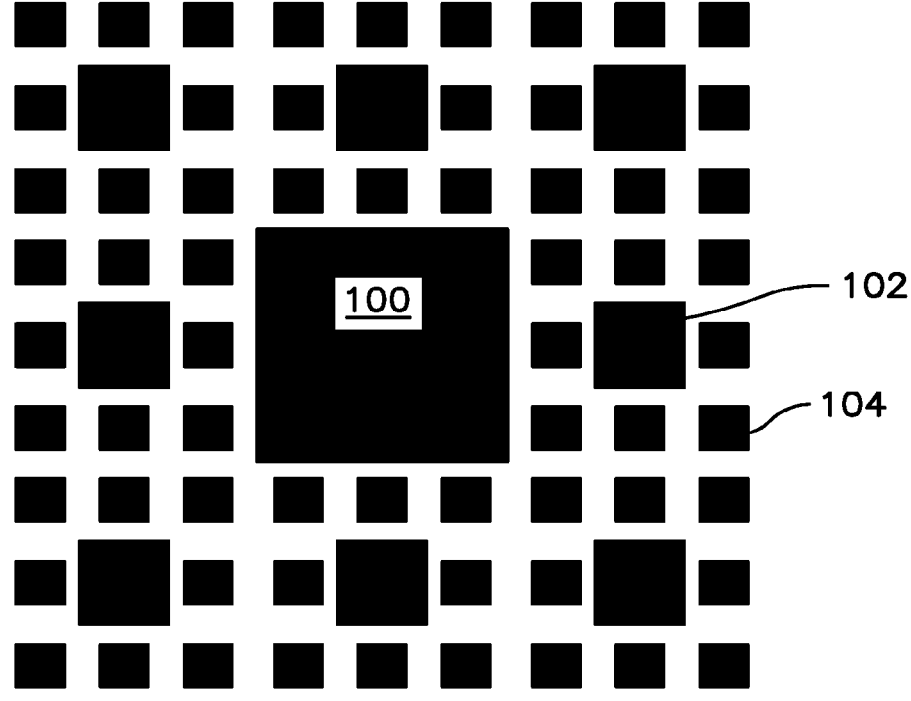
FIG. 4 illustrates one embodiment of a complex pattern that may be formed on a microneedle surface.

FIG. 4 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes may include larger structures having a cross-sectional dimension formed on a larger scale, e.g., microstructures having a cross-sectional dimension greater than about 500 nanometers in combination with smaller nanostructures. In one embodiment, microstructures of a complex nanotopography may have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 4 includes micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 4 have a cross-sectional dimension of about 400 nanometers, and pillars 104 have a cross-sectional dimension of about 200 nanometers.

A nanotopography may be formed of any number of different elements. For instance, a pattern of elements may include two different elements, three different elements, an example of which is illustrated in FIG. 4, four different elements, or more. The relative proportions of the recurrence of each different element may also vary. In one embodiment, the smallest elements of a pattern will be present in larger numbers than the larger elements. For instance in the pattern of FIG. 4, there are eight pillars 104 for each pillar 102, and there are eight pillars 102 for the central large pillar 100. As elements increase in size, there may generally be fewer recurrences of the element in the nanotopography. By way of example, a first element that is about 0.5, for instance between about 0.3 and about 0.7 in cross-sectional dimension as a second, larger element may be present in the topography about five times or more than the second element. A first element that is approximately 0.25, or between about 0.15 and about 0.3 in cross-sectional dimension as a second, larger element may be present in the topography about 10 times or more than the second element.

The spacing of individual elements may also vary. For instance, center-to-center spacing of individual structures may be between about 50 nanometers and about 1 micrometer, for instance between about 100 nanometers and about 500 nanometers. For example, center-to-center spacing between structures may be on a nano-sized scale. For instance, when considering the spacing of nano-sized structures, the center-to-center spacing of the structures may be less than about 500 nanometers. This is not a requirement of a topography, however, and individual structures may be farther apart. The center-to-center spacing of structures may vary depending upon the size of the structures. For example, the ratio of the average of the cross-sectional dimensions of two adjacent structures to the center-to-center spacing between those two structures may be between about 1:1 (e.g., touching) and about 1:4, between about 1:1.5 and about 1:3.5, or between about 1:2 and about 1:3. For instance, the center to center spacing may be approximately double the average of the cross-sectional dimensions of two adjacent structures. In one embodiment, two adjacent structures each having a cross-sectional dimension of about 200 nanometers may have a center-to-center spacing of about 400 nanometers. Thus, the ratio of the average of the diameters to the center-to-center spacing in this case is 1:2.

Structure spacing may be the same, i.e., equidistant, or may vary for structures in a pattern. For instance, the smallest structures of a pattern may be spaced apart by a first distance, and the spacing between these smallest structures and a larger structure of the pattern or between two larger structures of the pattern may be the same or different as this first distance.

For example, in the pattern of FIG. 4, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between to smallest pillars 104, about 100 nanometers. Of course, this is not a requirement, and all structures may be equidistant from one another or any variation in distances. In one embodiment, different structures may be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, nanostructures may have an aspect ratio falling within any of these ranges.

Figure 5:
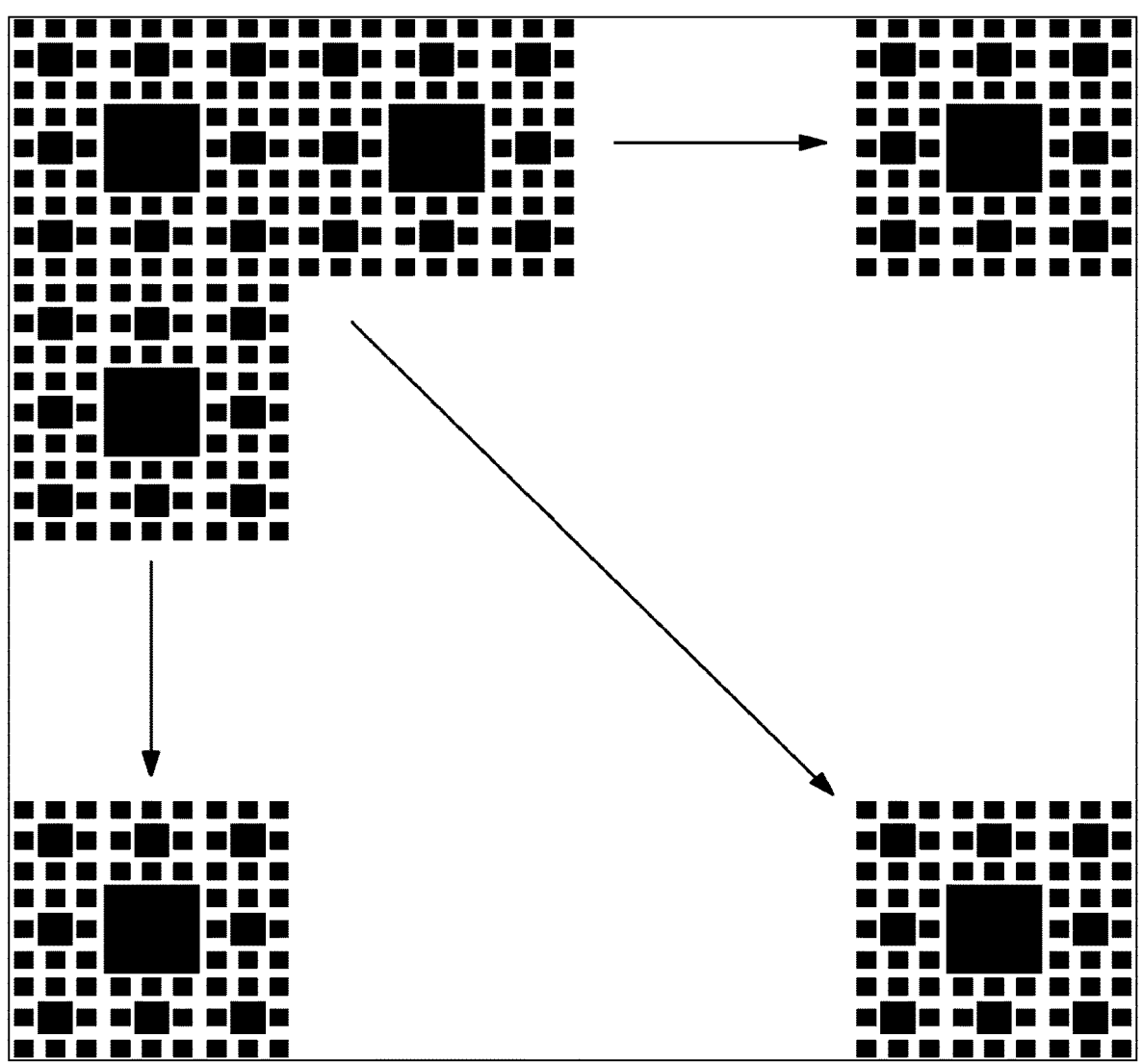
FIG. 5 illustrates a pattern including multiple iterations of the complex pattern of FIG. 4.

The device surface may include a single instance of a pattern, as shown in FIG. 4, or may include multiple iterations of the same or different patterns. For example, FIG. 5 illustrates a surface pattern including the pattern of FIG. 4 in multiple iterations over a surface.

The formation of nanotopography on a microneedle surface may increase the surface area of the microneedle without a corresponding increase in volume. Increase in the surface area to volume ratio is believed to improve the interaction of the microneedle surface with surrounding biological materials. For instance, increase in the surface area to volume ratio is believed to encourage mechanical interaction between the nanotopography and surrounding proteins, e.g., extracellular matrix (ECM) proteins and/or plasma membrane proteins. As utilized herein, the term "protein" generally refers to a molecular chain of amino acids that is capable of interacting structurally, enzymatically or otherwise with other proteins, polypeptides or any other organic or inorganic molecule.

In general, the surface area to volume ratio of a nanopatterned surface may be greater than about 10,000 cm$^{-1}$, greater than about 150,000 cm$^{-1}$, or greater than about 750,000 cm$^{-1}$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by Brunauer, Emmet, and Teller (J. Amer. Chem. Soc., vol. 60, February, 1938, pp. 309-319), incorporated herein by reference. The BET surface area may be less than about 5 m$^2$/g, in one embodiment, for instance between about 0.1 m$^2$/g and about 4.5 m$^2$/g, or between about 0.5 m$^2$/g and about 3.5 m$^2$/g. Values for surface area and volume may also be estimated from the geometry of molds used to form a surface, according to standard geometric calculations. For example, the volume may be estimated according to the calculated volume for each pattern element and the total number of pattern elements in a given area, e.g., over the surface of a single microneedle.

For a device that defines a fractal or fractal-like patterned nanotopography at a surface, the nanotopography may be characterized through determination of the fractal dimension of the pattern. The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)}$$

where N(e) is the number of self-similar structures needed to cover the whole object when the object is reduced by 1/e in each spatial direction.

For example, when considering the 2 dimensional fractal known as the Sierpenski triangle illustrated in FIG. 6, in which the mid-points of the three sides of an equilateral triangle are connected and the resulting inner triangle is removed, the fractal dimension is calculated as follows:

$$D = \frac{\log N(e)}{\log(e)}$$

$$D = \frac{\log 3}{\log 2}$$

$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 4 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

FIGS. 7A and 7B illustrate increasing magnification images of another example of a complex nanotopography. The nanotopography of FIGS. 7A and 7B includes an array of fibrous-like pillars 70 located on a substrate. At the distal end of each individual pillar, the pillar splits into multiple smaller fibers 60. At the distal end of each of these smaller fibers 60, each fiber splits again into multiple filaments (not visible in FIGS. 7A and 7B). Structures formed on a surface that have an aspect ratio greater than about 1 may be flexible, as are the structures illustrated in FIGS. 7A and 7B, or may be stiff.

FIGS. 7C and 7D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 7C and 7D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 8:
FIG. 8 illustrates another complex pattern that may be formed on a microneedle surface.

FIG. 8 illustrates another pattern including nano-sized structures as may be formed on a microneedle surface. As may be seen, in this embodiment, individual pattern structures may be formed at the same general size, but with different orientations and shapes from one another.

In addition to or alternative to the examination of surface area to volume ratio and/or fractal dimension, the microneedles of the RA drug delivery devices may be characterized by other methods including, without limitation, surface roughness, elastic modulus, surface energy, and so forth.

Methods for determining the surface roughness are generally known in the art. For instance, an atomic force microscope process in contact or non-contact mode may be utilized according to standard practice to determine the surface roughness of a material. Surface roughness that may be utilized to characterize a microneedle may include the average roughness ($R_A$), the root mean square roughness, the skewness, and/or the kurtosis. In general, the average surface roughness (i.e., the arithmetical mean height of the surface are roughness parameter as defined in the ISO 25178 series) of a surface defining nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers.

The microneedle surface may be characterized by the elastic modulus of the surface, for instance by the change in elastic modulus upon the addition of a nanotopography to the surface. In general, the addition of a plurality of structures forming nanotopography on the microneedle surface may decrease the elastic modulus of a material, as the addition of nano-sized structures on the surface will lead to a reduction in continuity of the surface and a related change in surface area. As compared to a similar microneedle formed according to the same process and of the same materials, but for the pattern of nanotopography on the surface, a microneedle including nanotopography thereon may exhibit a decrease in elastic modulus of between about 35% and about gg %, for instance between about 50% and about gg %, or between about 75% and about 80%. By way of example, the effective compression modulus of a nanopatterned surface may be less than about 50 MPa, or less than about 20 MPa. In one embodiment the effective compression modulus may be between about 0.2 MPa and about 50 MPa, between about 5 MPa and about 35 MPa, or between about 10 MPa and about 20 MPa. The effective shear modulus may be less than about 320 MPa, or less than about 220 MPa. For instance, the effective shear modulus may be between about 4 MPa and about 320 MPa, or between about 50 MPa and about 250 MPa, in one embodiment.

A microneedle including nanotopography thereon may also exhibit an increase in surface energy as compared to a similar microneedle that does not have the pattern of nanotopography thereon. For instance, the microneedle including a nanotopography formed thereon may exhibit an increase in surface energy as compared to a similar microneedle of the same materials and formed according to the same methods, but for the inclusion of the pattern of nanotopography on the surface. For instance, the water contact angle of a surface including a nanotopography thereon may be greater than about 80°, greater than about 90°, greater than about 100°, or greater than about 110°. For example, the water contact angle of a surface may be between about 80° and about 150°, between about 90° and about 130°, or between about 100° and about 120°, in one embodiment.

Figure 9A:
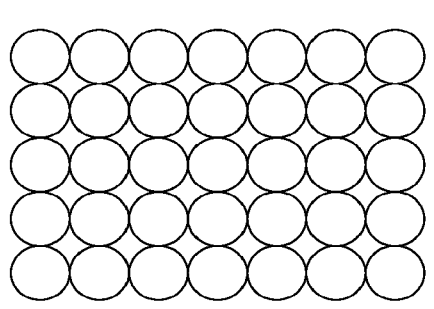
FIGS. 9A-9C illustrate exemplary packing densities as may be utilized for nano-sized structures as described herein including a square packing design (FIG. 9A), a hexagonal packing design (FIG. 9B), and a circle packing design (FIG. 9C).
Figure 9B:
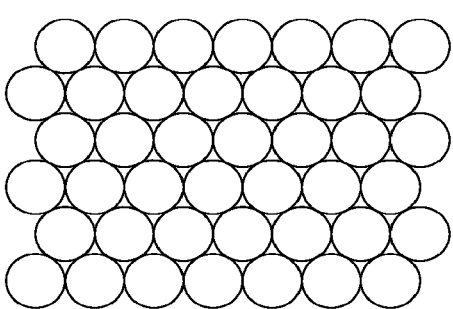
Figure 9C:
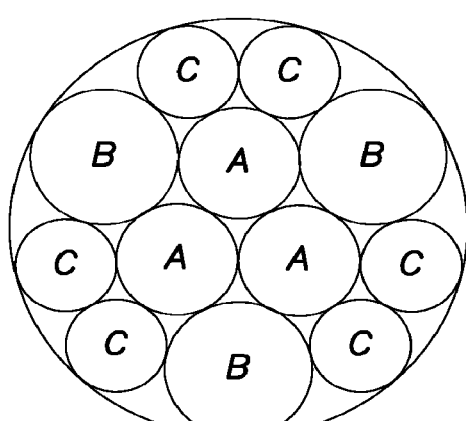

When forming nanostructures on the surface of the device, the packing density of the structures may be maximized. For instance, square packing (FIG. 9A), hexagonal packing (FIG. 9B), or some variation thereof may be utilized to pattern the elements on the microneedle. When designing a pattern in which various sized elements of cross sectional areas A, B, and C are adjacent to one another on the microneedle, circle packing as indicated in FIG. 9C may be utilized. Of course, variations in packing density and determination of associated alterations in characteristics of the surface are well within the abilities of one of skill in the art.

The microneedles including a fabricated nanotopography on the surface of the microneedles may be formed according to a single-step process, i.e., the microneedles are formed with the nanostructures on the surface at the time of formation. Alternatively, a multi-step process may be used, in which a pattern of nanostructures are fabricated on a preformed microneedle. For example, an array of microneedles may be first formed and then a random or non-random pattern of nanostructures may be fabricated on the surface of the formed microneedles. In either the single-step or two-step process, the nano-sized structures may be fabricated on the microneedle surface or on a mold surface according to any suitable nanotopography fabrication method including, without limitation, nanoimprinting, injection molding, lithography, embossing molding, and so forth.

An array of microneedles may be formed according to any standard microfabrication technique including, without limitation, lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, and lamination; stereolithography; laser machining; and laser ablation (including projection ablation).

An electrochemical etching process may be utilized in which electrochemical etching of solid silicon to porous silicon is used to create extremely fine (on the order of 0.01 μm) silicon networks that may be used as piercing structures. This method may use electrolytic anodization of silicon in aqueous hydrofluoric acid, potentially in combination with light, to etch channels into the silicon. By varying the doping concentration of the silicon wafer to be etched, the electrolytic potential during etching, the incident light intensity, and the electrolyte concentration, control over the ultimate pore structure may be achieved. The material not etched (i.e. the silicon remaining) forms the microneedles.

Plasma etching may also be utilized, in which deep plasma etching of silicon is carried out to create microneedles with diameters on the order of 0.1 μm or larger. Needles may be fabricated indirectly by controlling the voltage (as in electrochemical etching).

Lithography techniques, including photolithography, e-beam lithography, X-ray lithography, and so forth may be utilized for primary pattern definition and formation of a master die. Replication may then be carried out to form a device including an array of microneedles. Common replication methods include, without limitation, solvent-assisted micromolding and casting, embossing molding, injection molding, and so forth. Self-assembly technologies including phase-separated block copolymer, polymer demixing and colloidal lithography techniques may also be utilized in forming a nanotopography on a surface.

Combinations of methods may be used, as is known. For instance, substrates patterned with colloids may be exposed to reactive ion etching (RIE, also known as dry etching) so as to refine the characteristics of a fabricated nanostructure such as nanopillar diameter, profile, height, pitch, and so forth. Wet etching may also be employed to produce alternative profiles for fabricated nanostructures initially formed according to a different process, e.g., polymer de-mixing techniques.

Structure diameter, shape, and pitch may be controlled via selection of appropriate materials and methods. For example, etching of metals initially evaporated onto colloidal-patterned substrates followed by colloidal lift-off generally results in prism-shaped pillars. An etching process may then be utilized to complete the structures as desired. Ordered non-spherical polymeric nanostructures may also be fabricated via temperature-controlled sintering techniques, which form a variety of ordered trigonal nanometric features in colloidal interstices following selective dissolution of polymeric nanoparticles. These and other suitable formation processes are generally known in the art (see, e.g., Wood, JR Soc Interface, 2007 February 22; 4(12): 1-17, incorporated herein by reference).

Figures 10A, 10B, 10C:
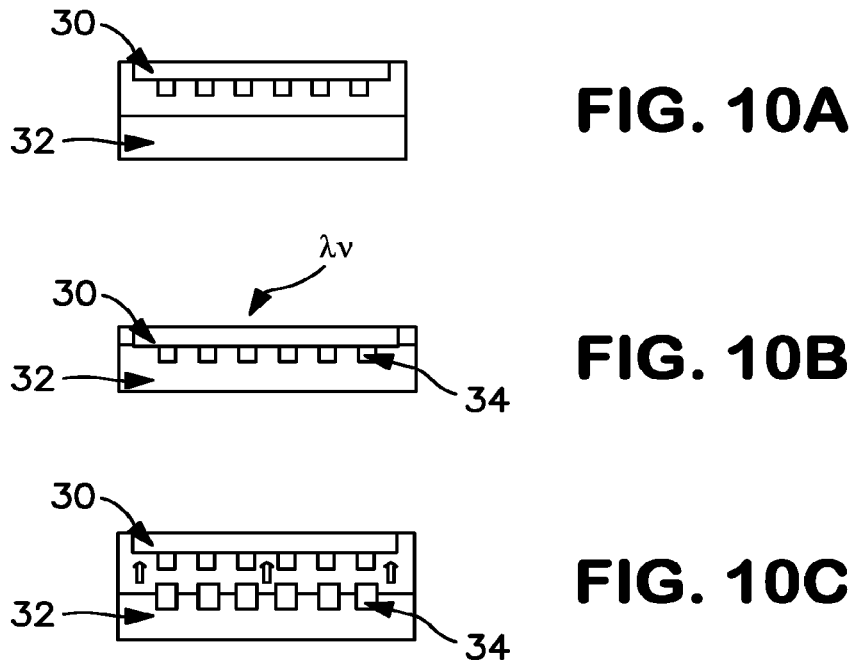
FIGS. 10A-10C schematically illustrate a nanoimprinting method as may be utilized in one embodiment in forming a device.

Other methods as may be utilized in forming a microneedle including a fabricated nanotopography on a surface include nanoimprint lithography methods utilizing ultra-high precision laser machining techniques, examples of which have been described by Hunt, et al. (U.S. Pat. No. 6,995,336) and Guo, et al. (U.S. Pat. No. 7,374,864), both of which are incorporated herein by reference. Nanoimprint lithography is a nano-scale lithography technique in which a hybrid mold is utilized which acts as both a nanoimprint lithography mold and a photolithography mask. A schematic of a nanoimprint lithography technique is illustrated in FIGS. 10A-10C. During fabrication, a hybrid mold 30 imprints into a substrate 32 via applied pressure to form features (e.g., microneedles defining nanotopography) on a resist layer (FIG. 10A). In general, the surface of the substrate 32 may be heated prior to engagement with the mold 30 to a temperature above its glass transition temperature ($T_g$). While the hybrid mold 30 is engaged with the substrate 32, a flow of viscous polymer may be forced into the mold cavities to form features 34 (FIG. 10B). The mold and substrate may then be exposed to ultraviolet light. The hybrid mold is generally transmissive to UV radiation save for certain obstructed areas. Thus, the UV radiation passes through transmissive portions and into the resist layer. Pressure is maintained during cooling of the mold and substrate. The hybrid mold 30 is then removed from the cooled substrate 32 at a temperature below Tg of the substrate and polymer (FIG. 10C).

To facilitate the release of the nanoimprinted substrate 32 including fabricated features 34 from the mold 30, as depicted in FIG. 10C, it is advantageous to treat the mold 30 with a low energy coating to reduce the adhesion with the substrate 32, as a lower surface energy of the mold 30 and the resulting greater surface energy difference between the mold 30, substrate 32, and polymer may ease the release between the materials. By way of example, a silicon mold coating may be used such as trideca-(1,1,2,2-tetrahydro)-octytrichloro silane (F13-TCS).

A nanoimprinting process is a dynamic one which includes filling a mold followed by detachment of a formed polymer from the mold. To fill the mold features, the polymer temperature must be raised to a level high enough to initiate flow under the applied pressure. The higher the temperature, the lower the polymer viscosity, and the faster and easier the mold will fill. A higher pressure will also improve the fill rate and overall fill for better mold replication. To release the nanoimprinted substrate from the mold, the substrate temperature may be lowered to a point where the yield strength exceeds the adhesional forces exerted by the mold. By varying the temperature it is also possible to draw the polymer features during detachment to obtain different structures, for instance structures as illustrated in FIG. 8.

The nanostructures may also be formed on the microneedle according to chemical addition processes. For instance, film deposition, sputtering, chemical vapor deposition (CVD), epitaxy (vapor phase, liquid phase, and molecular beam), electroplating, and so forth may be utilized for building structures on a surface.

Self-assembled monolayer processes as are known in the art may be utilized to form the structures on the microneedle surface. For instance, the ability of block copolymers to self-organize may be used to form a monolayer pattern on the surface. The pattern may then be used as a template for the growth of the desired structures, e.g., colloids, according to the pattern of the monolayer.

By way of example, a two-dimensional, cross-linked polymer network may be produced from monomers with two or more reactive sites. Such cross-linked monolayers have been made using self-assembling monolayer (SAM) (e.g., a gold/alkyl thiol system) or Langmuir-Blodgett (LB) monolayer techniques (Ahmed et al., Thin Solid Films 187: 141-153 (1990)) as are known in the art. The monolayer may be crosslinked, which may lead to formation of a more structurally robust monolayer.

The monomers used to form the patterned monolayer may incorporate all the structural moieties necessary to affect the desired polymerization technique and/or monolayer formation technique, as well as to influence such properties as overall solubility, dissociation methods, and lithographic methods. A monomer may contain at least one, and more often at least two, reactive functional groups.

A molecule used to form an organic monolayer may include any of various organic functional groups interspersed with chains of methylene groups. For instance a molecule may be a long chain carbon structure containing methylene chains to facilitate packing. The packing between methylene groups may allow weak Van der Waals bonding to occur, enhancing the stability of the monolayer produced and counteracting the entropic penalties associated with forming an ordered phase. In addition, different terminal moieties, such as hydrogen-bonding moieties, may be present at one terminus of the molecules, in order to allow growth of structures on the formed monolayer, in which case the polymerizable chemical moieties may be placed in the middle of the chain or at the opposite terminus. Any suitable molecular recognition chemistry may be used in forming the assembly. For instance, structures may be assembled on a monolayer based on electrostatic interaction, Van der Waals interaction, metal chelation, coordination bonding (i.e., Lewis acid/base interactions), ionic bonding, covalent bonding, or hydrogen bonding.

When utilizing a SAM-based system, an additional molecule may be utilized to form the template. This additional molecule may have appropriate functionality at one of its termini in order to form a SAM. For example, on a gold surface, a terminal thiol may be included. There are a wide variety of organic molecules that may be employed to effect replication. Topochemically polymerizable moieties, such as dienes and diacetylenes, are particularly desirable as the polymerizing components. These may be interspersed with variable lengths of methylene linkers.

For an LB monolayer, only one monomer molecule is needed because the molecular recognition moiety may also serve as the polar functional group for LB formation purposes. Lithography may be carried out on a LB monolayer transferred to a substrate, or directly in the trough. For example, an LB monolayer of diacetylene monomers may be patterned by UV exposure through a mask or by electron beam patterning.

Monolayer formation may be facilitated by utilizing molecules that undergo a topochemical polymerization in the monolayer phase. By exposing the assembling film to a polymerization catalyst, the film may be grown in situ, and changed from a dynamic molecular assembly to a more robust polymerized assembly.

Any of the techniques known in the art for monolayer patterning may be used. Techniques useful in patterning the monolayer include, but are not limited to, photolithography, e-beam techniques, focused ion-beam techniques, and soft lithography. Various protection schemes such as photoresist may be used for a SAM-based system. Likewise, block copolymer patterns may be formed on gold and selectively etched to form patterns. For a two-component system, patterning may also be achieved with readily available techniques.

Soft lithography techniques may be utilized to pattern the monolayer in which ultraviolet light and a mask may be used for patterning. For instance, an unpatterned base monolayer may be used as a platform for assembly of a UV/particle beam reactive monomer monolayer. The monomer monolayer may then be patterned by UV photolithography, e-beam lithography, or ion beam lithography, even though the base SAM is not patterned.

Growth of structures on a patterned monolayer may be achieved by various growth mechanisms, such as through appropriate reduction chemistry of a metal salt and the use of seed or template-mediated nucleation. Using the recognition elements on the monolayer, inorganic growth may be catalyzed at this interface by a variety of methods. For instance inorganic compounds in the form of colloids bearing the shape of the patterned organic monolayer may be formed. For instance calcium carbonate or silica structures may be templated by various carbonyl functionalities such as carboxylic acids and amides. By controlling the crystal growth conditions, it is possible to control the thickness and crystal morphology of the mineral growth. Titanium dioxide may also be templated.

Templated electroless plating techniques may be used to synthesize metals using existing organic functional groups. In particular, by chelating metal atoms to the carbonyl moieties of the organic pattern, electroless metal deposition may be catalyzed on the pattern, forming patterned metallic colloids. For instance, Cu, Au, Ni, Ag, Pd, Pt and many other metals plateable by electroless plating conditions may be used to form metal structures in the shape of the organic monolayer. By controlling the electroless plating conditions, it is possible to control the thickness of the plated metal structures.

Other 'bottom-up' type growth methods as are known in the art may be utilized, for example a method as described in U.S. Pat. No. 7,189,435 to Tuominen, et al., which is incorporated herein by reference, may be utilized. According to this method, a conducting or semiconducting substrate (for example, a metal, such as gold) may be coated with a block copolymer film (for example, a block copolymer of methylmethacrylate and styrene), where one component of the copolymer forms nanoscopic cylinders in a matrix of another component of the copolymer. A conducting layer may then be placed on top of the copolymer to form a composite structure. Upon vertical orientation of the composite structure, some of the first component may be removed, for instance by exposure to UV radiation, an electron beam, or ozone, degradation, or the like to form nanoscopic pores in that region of the second component.

In another embodiment, described in U.S. Pat. No. 6,926, 953 to Nealey, et al., incorporated herein by reference, copolymer structures may be formed by exposing a substrate with an imaging layer thereon, for instance an alkylsiloxane or an octadecyltrichlorosilane self assembled monolayer, to two or more beams of selected wavelengths to form interference patterns at the imaging layer to change the wettability of the imaging layer in accordance with the interference patterns. A layer of a selected block copolymer, for instance a copolymer of polystyrene and poly(methyl methacrylate) may then be deposited onto the exposed imaging layer and annealed to separate the components of the copolymer in accordance with the pattern of wettability and to replicate the pattern of the imaging layer in the copolymer layer. Stripes or isolated regions of the separated components may thus be formed with periodic dimensions in the range of 100 nanometers or less.

The microneedle surface may include a random distribution of fabricated nanostructures. Optionally, the microneedle surface may include additional materials, in conjunction with the fabricated nanostructures. For example, the microneedle may have fabricated thereon an electrospun fibrous layer, and a random or non-random pattern of nanostructures may be fabricated on this electrospun layer.

Electrospinning includes of the use of a high voltage supplier to apply an electrical field to a polymer melt or solution held in a capillary tube, inducing a charge on the individual polymer molecules. Upon application of the electric field, a charge and/or dipolar orientation will be induced at the air-surface interface. The induction causes a force that opposes the surface tension. At critical field strength, the electrostatic forces will overcome surface tension forces, and a jet of polymer material will be ejected from the capillary tube toward a conductive, grounded surface. The jet is elongated and accelerated by the external electric field as it leaves the capillary tube. As the jet travels in air, some of the solvent may evaporate, leaving behind charged polymer fibers which may be collected on the surface. As the fibers are collected, the individual and still wet fibers may adhere to one another, forming a nonwoven web on the surface. A pattern of nanostructures may then be fabricated on the electrospun surface, for instance through an embossing technique utilizing a mold defining the desired nanostructures. Applying the mold to the microneedle surface at suitable temperature and pressure may transfer the pattern to the microneedle surface. A surface of random electrospun nano-sized fibers may further improve the desirable characteristics of a microneedle surface, e.g., one or more of surface area to volume ratio, surface roughness, surface energy, and so forth, and may provide associated benefits.

In addition to the nanostructures, the microneedle surface may be chemically functionalized for improved interaction with tissues or individual cells. For instance, one or more biomolecules such as polynucleotides, polypeptides, entire proteins, polysaccharides, and the like may be bound to the microneedle surface prior to use.

In some embodiments, the microneedle surface may include suitable reactivity such that additional desired functionality may spontaneously attach to the surface with no pretreatment of the surface necessary. However, in other embodiments, pretreatment of the structured surface prior to attachment of the desired compound may be carried out. For instance, reactivity of a structure surface may be increased through addition or creation of amine, carboxylic acid, hydroxy, aldehyde, thiol, or ester groups on the surface. In one representative embodiment, a microneedle surface including a pattern of nanotstructures formed thereon may be aminated through contact with an amine-containing compound such as 3-aminopropyltriethoxy silane in order to increase the amine functionality of the surface and bind one or more biomolecules to the surface via the added amine functionality.

Materials as may be desirably bound to the surface of a patterned device may include ECM proteins such as laminins, tropoelastin or elastin, Tropocollagen or collagen, fibronectin, and the like. Short polypeptide fragments may be bound to the surface of a patterned device such as an RGD sequence, which is part of the recognition sequence of integrin binding to many ECM proteins. Thus, functionalization of a microneedle surface with RGD may encourage interaction of the device with ECM proteins and further limit foreign body response to the device during use.

The RA drug for delivery via the device may be associated therewith according to any suitable methodology. For instance, a transdermal microneedle patch may be utilized for delivery of materials beneath the stratum corneum to the stratum spinosum or the stratum germinativum, or even deeper into the dermis. The RA drug may be contained on the patch or fed to the patch so as to be transported across the stratum corneum in association with the microneedle, e.g., within the microneedle or at the surface of the microneedle.

The microneedle transdermal patch may include a reservoir, e.g., a vessel, a porous matrix, etc., that may store the RA drug and provide the RA drug for delivery. The device may include a reservoir within the device itself. For instance, the device may include a hollow, or multiple pores that may carry one or more RA agents for delivery. The RA agent may be released from the device via degradation of a portion or the entire device or via diffusion of the agent from the device.

Figure 11A:
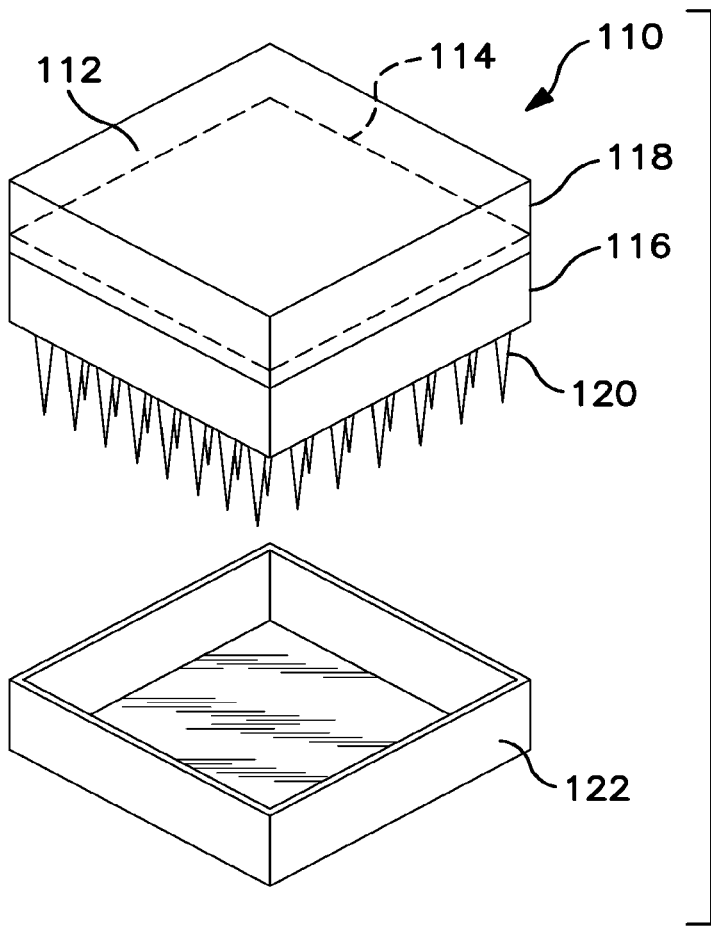
FIGS. 11A-11B schematically illustrate one embodiment of a device.
Figure 11B:
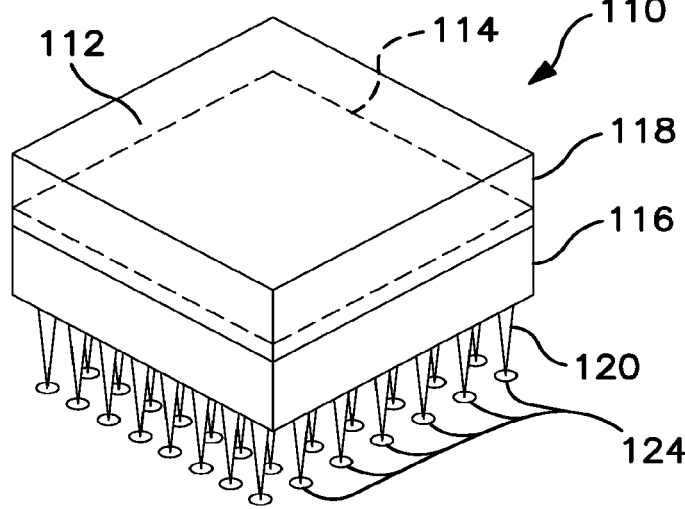

FIGS. 11A and 11B are perspective views of a device including a reservoir. The device 110 includes a reservoir 112 defined by an impermeable backing layer 114 and a microneedle array 116. The backing layer and the microneedle array 116 are joined together about the outer periphery of the device, as indicated at 118. The impermeable backing layer 114 may be joined by an adhesive, a heat seal or the like. The device 110 also includes a plurality of microneedles 120. A release liner 122 may be removed prior to use of the device to expose microneedles 120.

A formulation including one or more RA drugs may be retained within the reservoir 112. Materials suitable for use as impermeable backing layer 114 may include materials such as polyesters, polyethylene, polypropylene and other synthetic polymers. The material is generally heat or otherwise sealable to the backing layer to provide a barrier to transverse flow of reservoir contents.

Reservoir 112, defined by the space or gap between the impermeable backing layer 14 and the microneedle array 16, provides a storage structure in which to retain the suspension of RA agents to be administered. The reservoir may be formed from a variety of materials that are compatible with an agent to be contained therein. By way of example, natural and synthetic polymers, metals, ceramics, semiconductor materials, and composites thereof may form the reservoir.

In one embodiment, the reservoir may be attached to the substrate upon which the microneedles are located. According to another embodiment, the reservoir may be separate and removably connectable to the microneedle array or in fluid communication with the microneedle array, for instance via appropriate tubing, leur locks, etc.

The device may include one or a plurality of reservoirs for storing agents to be delivered. For instance, the device may include a single reservoir that stores a single or multiple RA agent-containing formulation, or the device may include multiple reservoirs, each of which stores one or more agents for delivery to all or a portion of the array of microneedles. Multiple reservoirs may each store a different material that may be combined for delivery. For instance, a first reservoir may contain an RA drug, e.g., an NSAID, and a second reservoir may contain a vehicle, e.g., saline, or a second RA drug, e.g., a DMARD. The different agents may be mixed prior to delivery. Mixing may be triggered by any means, including, for example, mechanical disruption (i.e. puncturing, degradation, or breaking), changing the porosity, or electrochemical degradation of the walls or membranes separating the chambers. Multiple reservoirs may contain different active agents for delivery that may be delivered in conjunction with one another or sequentially.

In one embodiment, the reservoir may be in fluid communication with one or more microneedles of the transdermal device, and the microneedles may define a structure (e.g., a central or lateral bore) to allow transport of delivered agents beneath the barrier layer.

The device may include one or a plurality of reservoirs for storing agents to be delivered. For instance, the device may include a single reservoir that stores a single agent or multiple agent formulation, or the device may include multiple reservoirs, each of which stores one or more agents for delivery to all or a portion of the array of microneedles. Multiple reservoirs may each store a different material that may be combined for delivery. For instance, a first reservoir may contain an agent, e.g., a drug, and a second reservoir may contain a vehicle, e.g., saline. The different agents may be mixed prior to delivery. Mixing may be triggered by any means, including, for example, mechanical disruption (i.e. puncturing, degradation, or breaking), changing the porosity, or electrochemical degradation of the walls or membranes separating the chambers. Multiple reservoirs may contain different active agents for delivery that may be delivered in conjunction with one another or sequentially.

The reservoir may be in fluid communication with one or more microneedles of the transdermal device, and the microneedles may define a structure (e.g., a central or lateral bore) to allow transport of delivered agents beneath the barrier layer.

Figure 12:
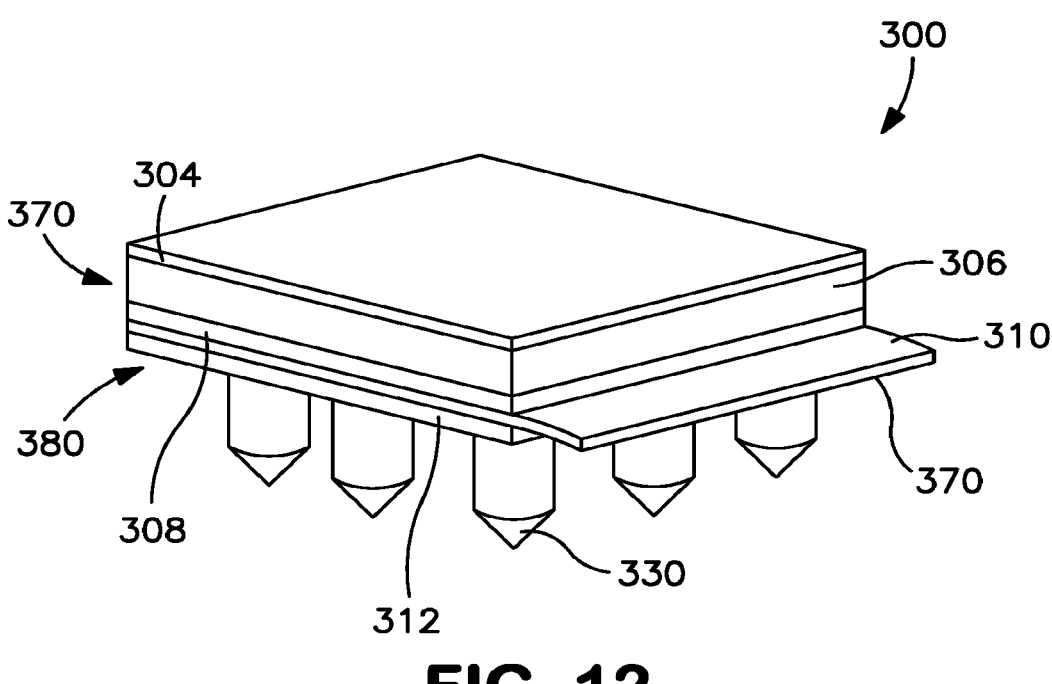
FIG. 12 is a perspective view of one embodiment of a transdermal patch prior to delivery of a drug compound.
Figure 13:
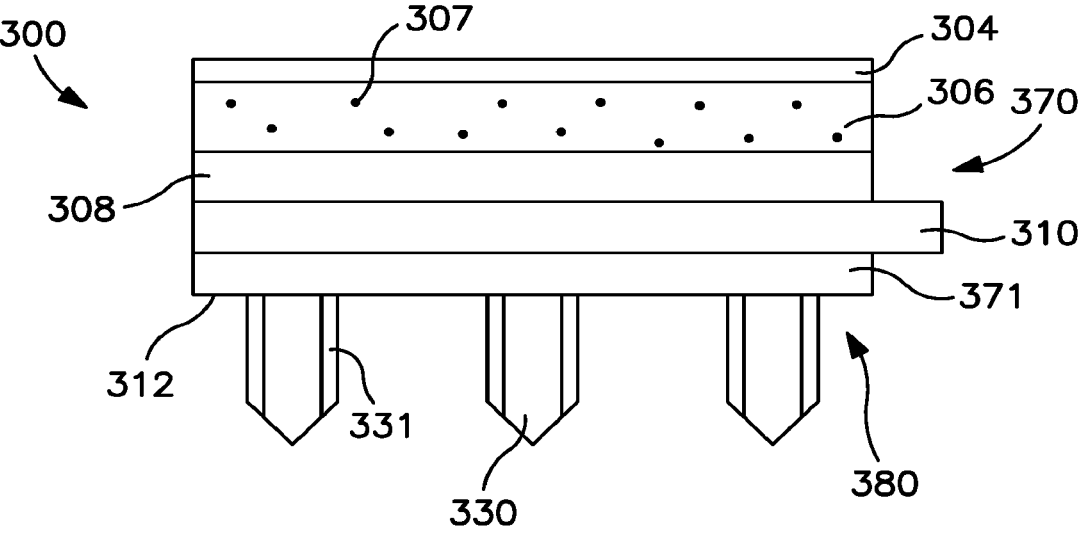
FIG. 13 is a front view of the patch of FIG. 12.

In alternative embodiments, a device may include a microneedle assembly and a reservoir assembly with flow prevention between the two prior to use. For instance, a device may include a release member positioned adjacent to both a reservoir and a microneedle array. The release member may be separated from the device prior to use such that during use the reservoir and the microneedle array are in fluid communication with one another. Separation may be accomplished through the partial or complete detachment of the release member. For example, referring to FIGS. 12-17, one embodiment of a release member is shown that is configured to be detached from a transdermal patch to initiate the flow of a drug compound. More particularly, FIGS. 12-13 show a transdermal patch 300 that contains a drug delivery assembly 370 and a microneedle assembly 380. The drug delivery assembly 370 includes a reservoir 306 positioned adjacent to a rate control membrane 308.

The rate control membrane may help slow down the flow rate of the drug compound upon its release. Specifically, fluidic drug compounds passing from the drug reservoir to the microneedle assembly via microfluidic channels may experience a drop in pressure that results in a reduction in flow rate. If this difference is too great, some backpressure may be created that may impede the flow of the compound and potentially overcome the capillary pressure of the fluid through the microfluidic channels. Thus, the use of the rate control membrane may ameliorate this difference in pressure and allow the drug compound to be introduced into the microneedle at a more controlled flow rate. The particular materials, thickness, etc. of the rate control membrane may vary based on multiple factors, such as the viscosity of the drug compound, the desired delivery time, etc.

The rate control membrane may be fabricated from permeable, semi-permeable or microporous materials that are known in the art to control the rate of drug compounds and having permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

Referring to FIGS. 12-13, although optional, the assembly 370 also contains an adhesive layer 304 that is positioned adjacent to the reservoir 306. The microneedle assembly 380 likewise includes a support 312 from which extends a plurality of microneedles 330 having channels 331, such as described above. The layers of the drug delivery assembly 370 and/or the microneedle assembly 380 may be attached together if desired using any known bonding technique, such as through adhesive bonding, thermal bonding, ultrasonic bonding, etc.

Regardless of the particular configuration employed, the patch 300 also contains a release member 310 that is positioned between the drug delivery assembly 370 and the microneedle assembly 380. While the release member 310 may optionally be bonded to the adjacent support 312 and/or rate control membrane 308, it is typically desired that it is only lightly bonded, if at all, so that the release member 310 may be easily withdrawn from the patch 300. If desired, the release member 310 may also contain a tab portion 371 (FIGS. 12-13) that extends at least partly beyond the perimeter of the patch 300 to facilitate the ability of a user to grab onto the member and pull it in the desired direction. In its "inactive" configuration as shown in FIGS. 12-13, the drug delivery assembly 370 of the patch 300 securely retains a drug compound 307 so that it does not flow to any significant extent into the microneedles 330. The patch may be "activated" by simply applying a force to the release member so that it is detached from the patch.

Figure 14:
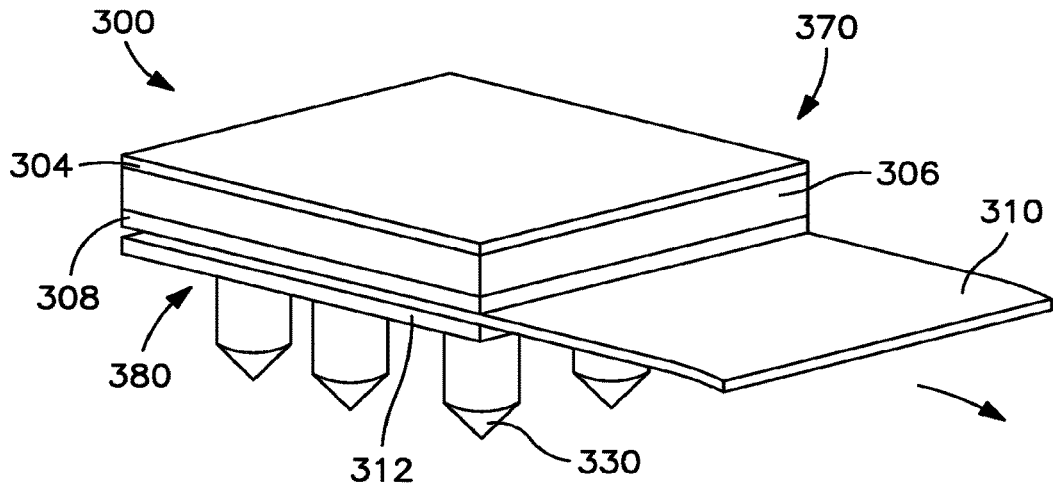
FIG. 14 is a perspective view of the patch of FIG. 12 in which the release member is partially withdrawn from the patch.
Figure 15:
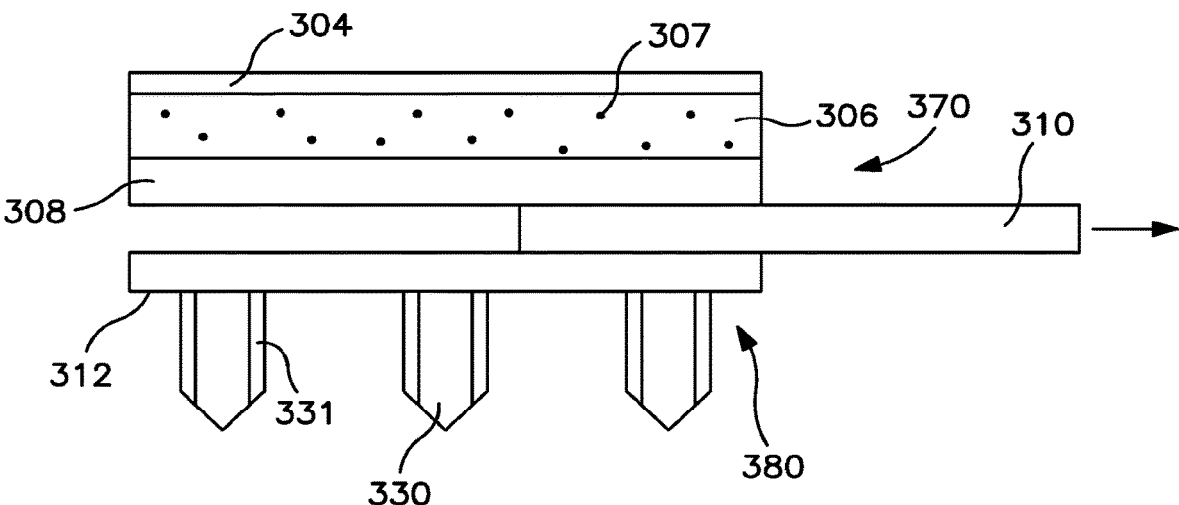
FIG. 15 is a front view of the patch of FIG. 12.
Figure 16:
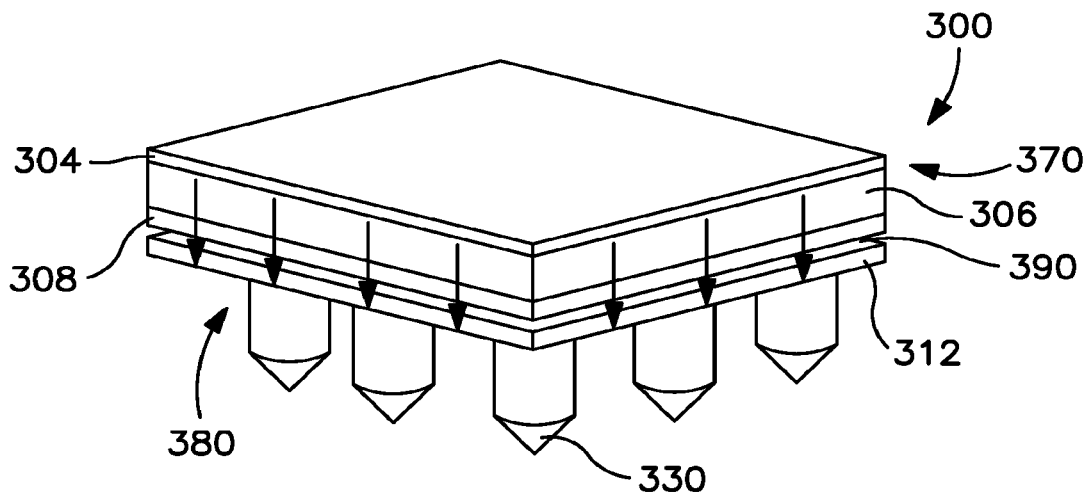
FIG. 16 is a perspective view of the transdermal patch of FIG. 12 after removal of the release member and during use.
Figure 17:
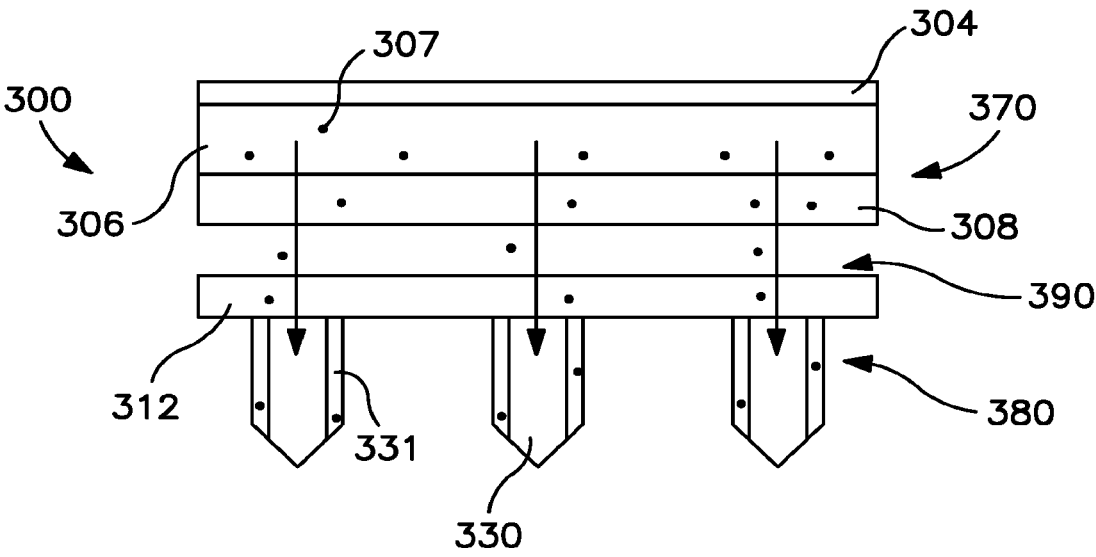
FIG. 17 is a front view of the patch of FIG. 16.

Referring to FIGS. 14-15, one embodiment for activating the patch 300 is shown in which the release member 310 is pulled in a longitudinal direction. The entire release member 310 may be removed as shown in FIGS. 16-17, or it may simply be partially detached as shown in FIGS. 14-15. In either case, however, the seal previously formed between the release member 310 and the aperture (not shown) of the support 312 is broken. In this manner, a drug compound 107 may begin to flow from the drug delivery assembly 170 and into the channels 131 of the microneedles 130 via the support 112. An exemplary illustration of how the drug compound 307 flows from the reservoir 306 and into the channels 331 is shown in FIGS. 16-17. Notably, the flow of the drug compound 307 is passively initiated and does not require any active displacement mechanisms (e.g., pumps).

In the embodiments shown in FIGS. 12-17, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Figure 19:
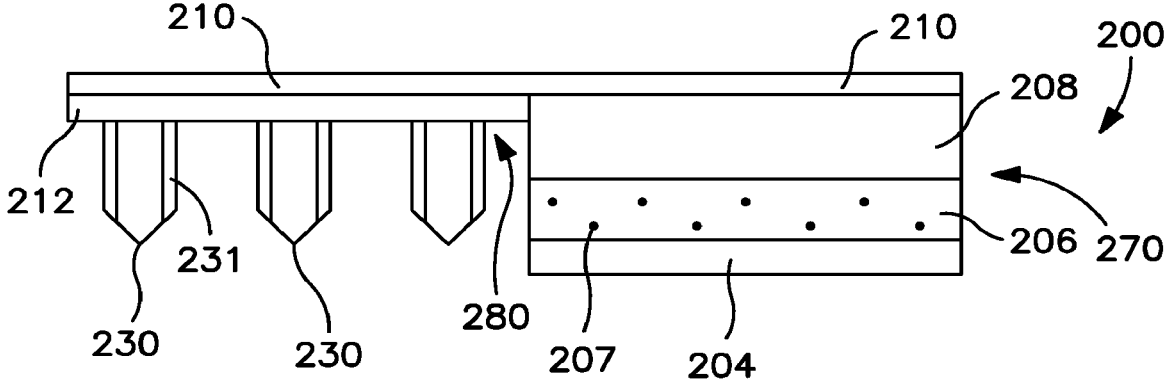
FIG. 19 is a front view of the patch of FIG. 18.

Referring to FIGS. 18-23, for example, one particular embodiment of a patch 200 is shown. FIGS. 18-19 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

In this embodiment, the support 212 and the rate control membrane 208 are initially positioned horizontally adjacent to each other, and a release member 210 extends over the support 212 and the rate control member 208. In this particular embodiment, it is generally desired that the release member 210 is releasably attached to the support 212 and the rate control membrane 208 with an adhesive (e.g., pressure-sensitive adhesive). In its "inactive" configuration as shown in FIGS. 18-19, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 20-21, to break the seal previously formed between the release member 210 and the aperture (not shown) of the support 212. Thereafter, the second section 260 may be folded about a fold line "F" as shown by the directional arrow in FIG. 22 so that the rate control member 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 23).

The device may deliver an agent at a rate so as to be therapeutically useful. In accord with this goal, the transdermal device may include a housing with microelectronics and other micro-machined structures to control the rate of delivery either according to a preprogrammed schedule or through active interface with the patient, a healthcare professional, or a biosensor. The device may include a material having a predetermined degradation rate, so as to control release of an RA agent contained within the device. The delivery rate may be controlled by manipulating a variety of factors, including the characteristics of the formulation to be delivered (e.g., viscosity, electric charge, and/or chemical composition); the dimensions of the device (e.g., outer diameter and the volume of any openings); the number of microneedles on a transdermal patch; the number of individual devices in a carrier matrix; the application of a driving force (e.g., a concentration gradient, a voltage gradient, a pressure gradient); the use of a valve; and so forth.

Transportation of agents through the device may be controlled or monitored using, for example, various combinations of valves, pumps, sensors, actuators, and microprocessors. These components may be produced using standard manufacturing or microfabrication techniques. Actuators that may be useful with a device may include micropumps, microvalves, and positioners. For instance, a microprocessor may be programmed to control a pump or valve, thereby controlling the rate of delivery.

Flow of an agent through the device may occur based on diffusion or capillary action, or may be induced using conventional mechanical pumps or nonmechanical driving forces, such as electroosmosis or electrophoresis, or convection. For example, in electroosmosis, electrodes are positioned on a biological surface (e.g., the skin surface), a microneedle, and/or a substrate adjacent a microneedle, to create a convective flow which carries oppositely charged ionic species and/or neutral molecules toward or into the delivery site.

Flow of an agent may be manipulated by selection of the material forming the microneedle surface. For example, one or more large grooves adjacent the microneedle surface of the device may be used to direct the passage of the RA drug. Alternatively, the materials forming the nanostructured surface may be manipulated to either promote or inhibit transport of material along the surface, such as by controlling hydrophilicity or hydrophobicity.

The flow of an agent may be regulated using valves or gates as is known in the art. Valves may be repeatedly opened and closed, or they may be single-use valves. For example, a breakable barrier or one-way gate may be installed in the device between a reservoir and the patterned surface. When ready to use, the barrier may be broken or gate opened to permit flow through to the microneedle surface. Other valves or gates used in the device may be activated thermally, electrochemically, mechanically, or magnetically to selectively initiate, modulate, or stop the flow of molecules through the device. In one embodiment, flow is controlled by using a rate-limiting membrane as a "valve."

In general, any agent delivery control system, including reservoirs, flow control systems, sensing systems, and so forth as are known in the art may be incorporated with devices. By way of example, U.S. Pat. Nos. 7,250,037, 7,315,758, 7,429,258, 7,582,069, and 7,611,481 describe reservoir and control systems as may be incorporated in devices.

During use, the presence of the nanostructured surface of the microneedles within the skin may affect formation and maintenance of cell/cell junctions including tight junctions and desmosomes. As previously mentioned, tight junctions have been found in the stratum granulosum and opening of the tight junctions may provide a paracellular route for improved delivery of RA drugs, particularly large molecular weight active agents and/or agents that exhibit low lipophilicity that have previously been blocked from transdermal delivery.

During use, the device may interact with one or more components of the contacting epithelial tissue to increase porosity of the tissue via paracellular and/or transcellular transport mechanisms. Epithelial tissue is one of the primary tissue types of the body. Epithelial tissue as may be rendered more porous according to the present disclosure may include both simple and stratified epithelium, including both keratinized epithelium and transitional epithelium. In addition, epithelial tissue encompassed herein may include any cell types of an epithelial layer including, without limitation, keratinocytes, squamous cells, columnar cells, cuboidal cells and pseudostratified cells.

Interaction between individual cells and structures of the nanotopography may induce the passage of an agent through a barrier cell and encourage transcellular transport. For instance, interaction with keratinocytes of the stratum corneum may encourage the partitioning of an agent into the keratinocytes, followed by diffusion through the cells and across the lipid bilayer again. While an agent may cross a barrier according to both paracellular and transcellular routes, the transcellular route may be predominate for highly hydrophilic molecules, though, of course, the predominant transport path may vary depending upon the nature of the agent, hydrophilicity being only one defining characteristic.

The present disclosure may be further understood with reference to the Examples provided below.

Example 1

Several different molds were prepared using photolithography techniques similar to those employed in the design and manufacture of electrical circuits. Individual process steps are generally known in the art and have been described.

Initially, silicon substrates were prepared by cleaning with acetone, methanol, and isopropyl alcohol, and then coated with a 258 nanometer (nm) layer of silicon dioxide according to a chemical vapor deposition process.

A pattern was then formed on each substrate via an electron beam lithography patterning process as is known in the art using a JEOL JBX-9300FS EBL system. The processing conditions were as follows:

Beam current=11 nA
Acceleration voltage=100 kV
Shot pitch=14 nm
Dose=260 $\mu C/cm^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (seem) He, 22 seem CF4, 20 seem C4Fs at 4 mTorr, 400 W coil, 200 W RIE and a DC Bias of 404-411 V.

Following, a silicon etch was carried out with an STS silicon oxide etch (SOE). Etch time was 2 minutes utilizing 20 seem $Cl_2$ and 5 seem Ar at 5 mTorr, 600 W coil, 50 W RIE and a DC Bias of 96-102 V. The silicon etch depth was 500 nanometers.

A buffered oxide etchant (BOE) was used for remaining oxide removal that included a three minute BOE immersion followed by a deionized water rinse.

An Obducat NIL-Eitre®6 nanoimprinter was used to form nanopatterns on a variety of polymer substrates. External water was used as coolant. The UV module utilized a single pulsed lamp at a wave length of between 200 and 1000 nanometers at 1.8 $W/cm^2$. A UV filter of 250-400 nanometers was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane (F13-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the F13-TCS was added to the Petri dish. A silicon mold was placed in the Petri dish and covered for 10-15 minutes to allow the F13-TCS vapor to wet out the silicon mold prior to removal of the mold.

Five different polymers as given in Table 1, below, were utilized to form various nanotopography designs.

TABLE 1

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Several different nanotopography patterns were formed, schematic representations of which are illustrated in FIGS. 24A-24D. The nanotopography pattern illustrated in FIG. 12E was a surface of a flat substrate purchased from NTT Advanced Technology of Tokyo, Japan. The patterns were designated DN1 (FIG. 24A), DN2 (FIG. 24B), DN3 (FIG. 24C), DN4 (FIG. 24D) and NTTAT2 (FIG. 24E). SEM images of the molds are shown in FIGS. 24A, 24B, and 24C, and images of the films are shown in FIGS. 24D and 24E. FIG. 8 illustrates a nanopatterned film formed by use of the mold of FIG. 24A (DN1). In this particular film, the polymer features were drawn by temperature variation as previously discussed. The surface roughness of the pattern of FIG. 24E was found to be 34 nanometers.

The pattern illustrated in FIGS. 7C and 7D was also formed according to this nanoimprinting process. This pattern included the pillars 72 and pillars 62, as illustrated. Larger pillars 72 were formed with a 3.5 micrometer (μm) diameter and 30 μm heights with center-to-center spacing of 6.8 μm. Pillars 62 were 500 nanometers in height and 200 nanometers in diameter and a center-to-center spacing of 250 nanometers.

The nanoimprinting process conditions used with polypropylene films are provided below in Table 2.

TABLE 2

| Time (s) | Temperature (C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

Example 2

Films were formed as described above in Example 1 including various different patterns and formed of either polystyrene (PS) or polypropylene (PP). The underlying substrate varied in thickness. Patterns utilized were either DN2, DN3, or DN4 utilizing formation processes as described in Example 1. The pattern molds were varied with regard to hole depth and feature spacing to form a variety of differently-sized features having the designated patterns. Sample no. 8 (designated B81) was formed by use of a 0.6 μm millipore polycarbonate filter as a mold. A 25 μm polypropylene film was laid over the top of the filter and was then heated to melt such that the polypropylene could flow into the pores of the filter. The mold was then cooled and the polycarbonate mold dissolved by use of a methylene chloride solvent.

SEMs of the formed films are illustrated in FIGS. 25-33 and characteristics of the formed films are summarized in Table 3, below.

The fractal dimension may also be evaluated from 2D Fourier spectra by application of the Log Log function. If the surface is fractal the Log Log graph should be highly linear, with at negative slope (see, e.g., Fractal Surfaces, John C. Russ, Springer-Verlag New York, LLC, July, 2008).

Example 3

HaCaT human skin epithelial cells were grown in DMEM, 10% FBS, 1% penicillin/streptomycin at 37° C., 5% CO2 for 24 hours at a concentration of 25,000 cell/cm$^2$ in 6 well plates. Plates either had polypropylene nanopatterned films formed as described above in Example 1 and designate DN1, DN2 (Sample 4 of Table 3), DN3 or untreated surface at the bottom of the well. Nanopatterned films were adhered in place with cyanoacrylate.

TABLE 3

| Sample No. | FIG. | Pattern | Material | Film thickness (μm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 1 | 25 | DN3 | PS | 75 | A | 1100 nm | 520 nm | 0.47 | 150 | 2.0 | 100° |
|  |  |  |  |  | B | 400 nm | 560 nm | 1.4 |  |  |  |
|  |  |  |  |  | C | 200 nm | 680 nm | 3.4 |  |  |  |
| 2 | 26A, 26B | DN2 | PP | 5.0 | n/a | 200 nm | 100 nm | 0.5 | 16 | 2.15 | 91° |
| 3 | 27 | DN2 | PS | 75 | n/a | 200 nm | 1.0 μm | 5 | 64 | 2.2 | 110° |
| 4 | 28 | DN2 | PP | 25.4 | n/a | 200 nm | 300 nm | 1.5 | 38 | 1.94 | 118° |
| 5 | 29 | DN3 | PS | 75 | A | 1100 nm | 570 nm | 0.52 | 21.1 | 1.98 | 100° |
|  |  |  |  |  | B | 400 nm | 635 nm | 1.6 |  |  |  |
|  |  |  |  |  | C | 200 nm | — | — |  |  |  |
| 6 | 30 | DN4 | PS | 75 | n/a | 200 nm | — | — | 30.6 | 2.04 | 80° |
| 7 | 31 | DN4 | PP | 25.4 | n/a | 200 nm | — | — | 21.4 | 2.07 | 112° |
| 8 | 32 | BB1 | PP | 25.4 | n/a | 600 nm | 18 μm | 30 | 820 | 2.17 | 110° |
| 9 | 33 | DN3 | PP | 5 | A | 1100 nm | 165 nm | 0.15 | 50 | 2.13 |  |
|  |  |  |  |  | B | 400 nm | 80 nm | 0.2 |  |  |  |
|  |  |  |  |  | C | 200 nm | 34 nm | 0.17 |  |  |  |

[1]Pattern Features as shown on the figures.
[2]Cross sectional dimension values are derived from the mold and equated as an approximation of the maximum dimension of the structure, although it should be understood that the actual dimension of an individual structure may vary slightly as may be seen in the figures.
[3]Feature heights are provided as the average of several individually determined feature heights.

For each sample AFM was utilized to characterize the film. Characterizations included formation of scanning electron micrograph (SEM), determination of surface roughness, determination of maximum measured feature height, and determination of fractal dimension.

The atomic force microscopy (AFM) probe utilized was a series 16 silicon probe and cantilever available from μMasch. The cantilever had a resonant frequency of 170 kHz, a spring constant of 40 N/m, a length of 230±5 μm, a width of 40±3 μm, and a thickness of 7.0±0.5 μm. The probe tip was an n-type phosphorous-doped silicon probe, with a typical probe tip radius of 10 nanometers, a full tip cone angle of 40°, a total tip height of 20-25 μm, and a bulk resistivity 0.01-0.05 ohm-cm.

The surface roughness value given in Table 3 is the arithmetical mean height of the surface areal roughness parameter as defined in the ISO 25178 series.

The Fractal Dimension was calculated for the different angles by analyzing the Fourier amplitude spectrum; for different angles the amplitude Fourier profile was extracted and the logarithm of the frequency and amplitude coordinates calculated. The fractal dimension, D, for each direction is then calculated as $$D=(6+s)/2,$$

where s is the (negative) slope of the log-log curves. The reported fractal dimension is the average for all directions.

Cells were detached from the surfaces with 1 ml of trypsin per well for 10 minutes, quenched with 1 ml growth medium (same as above), then transferred to a microfuge tube and pelleted at 1200 rpm for 7 minutes.

RNA was isolated from pelleted cells using the RNeasy miniprep kit from Qiagen using the manufacturer's protocol. Briefly, cells were lysed, mixed with ethanol and spun down in a column. Lysates were then washed 3 times, treated with DNase and eluted in 40 μl volumes.

cDNA was created from the RNA isolated using the RT first strand kit from SA Biosciences. Briefly, RNA was treated with DNase again at 42° C. for 5 minutes. Random primers and reverse transcriptase enzyme was then added and incubated at 42° C. for 15 minutes, then incubated at 95° C. for 5 minutes to stop reaction.

qPCR was then performed on the cDNA samples using RT profiler custom PCR array from SA Biosciences with primers for IL1-β, IL6, IL8, IL10, ID1R1, TNFα, TGFβ-1, PDGFA, GAPDH, HDGC, RTC and PPC. Briefly, cDNA was mixed with SYBR green and water, and then added to a PCR plate pre-fixed with the correct sense and antisense primer pair for the gene of interest. The plate was then run on an ABI StepOnePlus PCR machine heated to 95° C. for 10 minutes, then for 45 cycles of: 15 seconds at 95° C. and 1 minute at 60° C.

Delta delta CT analysis was performed using GAPDH as the internal control. HDGC, RTC and PPC levels were used as additional internal controls for activity and genomic DNA contamination.

One-way ANOVA and Tukey's 2-point tests were then used to determine statistical significance in the differences between surfaces.

Table 4, below, presents the protein expressions obtained as the fold change in expression on nanoimprinted structures produced on polypropylene films versus expression on an unstructured film.

TABLE 4

| Mold | IL1-β | IL6 | IL8 | IL10 | IL1R1 | TNFα | TGFβ1 | PDGFA |
|---|---|---|---|---|---|---|---|---|
| DN1 | 2.24 | 3.33 | 0.36 | 1.17 | 0.6 | 0.57 | 0.37 | 1.37 |
| DN2 | 3.18 | 3.2 | 0.46 | 0.43 | 0.36 | 0.57 | 0.42 | 1.23 |
| DN3 | 3.36 | 2.7 | 0.47 | 5.83 | 1.6 | 0.37 | 0.35 | 0.64 |

Example 4

Methods as described in Example 3 were utilized to examine the expression level for several different cytokines from HaCaT human skin epithelial cells when the cells were allowed to develop on a variety of different polypropylene (PP) or polystyrene (PS) films, formed and patterned as described above. The expression level for each cytokine was compared to that from the same cell type cultured on standard tissue culture polystyrene (TCPS) and induced with lipopolysaccharide (LPS). Results are shown in Table 5, below.

Cells developed on a polypropylene film nanopatterned with a DN2 pattern, as described above (Sample 4 of Table 3), were found to upregulate expression of IL-1β, IL-1ra, IL-10, and MIP-1β downregulate expression of IL-4, IL-13, MIG, KC, IL-2, MIP-1, TNF-α, IL-12, IL-16, and IL-1α as compared to TCPS.

Several other films were examined for effect on cellular expression of different cytokines. Films were designated as follows:

1—DN2 pattern on a 75 μm polystyrene film (Sample 3 of Table 3)
2—DN3 pattern on a 75 μm polystyrene film (Sample 1 of Table 3)
3—DN4 pattern on a 75 μm polystyrene film (Sample 6 of Table 3)
4—unimprinted 75 μm polystyrene film
5—DN2 pattern on a 25.4 μm polypropylene film (Sample 4 of Table 3)
6—DN4 pattern on a 25.4 μm polypropylene film (Sample 7 of Table 3)
7—DN2 pattern on a 5 μm polypropylene film (Sample 2 of Table 3)
8—BB1 polypropylene film (Sample 8 of Table 3)
9—unimprinted 25.4 μm polypropylene film
10—unimprinted 6 μm polypropylene film Results are illustrated in Table 5, below. Results are provided as follows:

-- expression level was below the testing threshold
– expression level was lower than that for TCPS
= expression level was similar to that for TCPS
+ expression level was above that for TCPS, but below that when induced with LPS
++ expression level was similar to that for induction with LPS
+++ expression level was above that for induction with LPS

TABLE 5

| Film | 1 | 2 | 3 | 4 | 5 | 6 | 7 | 8 | 9 | 10 |
|---|---|---|---|---|---|---|---|---|---|---|
| IL-1α | -- | -- | -- | -- | -- | -- | -- | -- | -- | -- |
| IL-1β | ++ | -- | -- | ++ | -- | -- | -- | -- | -- | -- |
| IL-12 | = | = | = | = | = | = | = | = | = | = |
| TNF-α | =+ | = | = | = | = | = | = | =+ | = | = |
| MCP-1 | =+ | = | = | = | = | = | = | =+ | = | = |
| IL-2 | = | =— | =+ | = | = | = | = | = | -- | = |
| KC | -- | -- | = | = | = | = | = | = | — | — |
| MIP-1α | -- | -- | -- | +++ | -- | -- | + | -- | +++ | +++ |
| MIP-1β | ++ | + | = | = | = | + | = | — | — | = |
| MIG | = | -- | = | + | — | — | -- | — | — | = |
| GM-CSI | -- | -- | -- | -- | -- | -- | -- | -- | -- | -- |
| IL-4 | -- | -- | -- | -- | -- | -- | -- | -- | -- | -- |
| IL-13 | -- | -- | -- | ++ | -- | -- | -- | -- | -- | -- |
| IL-10 | — | — | = | = | = | = | = | = | = | = |

Example 5

HaCaT human skin epithelial cells were grown in DMEM, 10% FBS, 1% penicillin/streptomycin at 37° C., 5% CO2 for 24 hours at a concentration of 25,000 cell/cm$^2$ in 6 well plates. Plates either had a polypropylene film formed as described above in Example 1 with designation DN1, DN2 (Sample 4 of Table 3), DN3 or an untreated surface at the bottom of the well. Films were adhered in place with cyanoacrylate.

Media was collected from each well and analyzed for cytokine production with a Milliplex Map Kit from Millipore. Beads to detect IL1-p, IL1RA, IL6, ILS, IL10, PDGF-AA, PGGF-AB/BB and TNF-α were used. Readings were done on a BioRad BioPlex machine. Briefly, media was placed into microplate wells with filters. Primary beads were added and incubated at room temperature for 1 hour with shaking. The plates were then washed and incubated with detection antibodies for 30 minutes at room temperature with shaking. Strepavidin-phycoertythrin was then added and incubated at room temperature for an additional 30 minutes. Plates were then washed, beads were resuspended in assay buffer and median fluorescent intensity was analyzed on the BioPlex.

Example 6

The permeability effects of films patterned as described herein were determined on a monolayer of Caco-2 cells (human epithelial colorectal adenocarcinoma cells).

Films formed as described above in Example 1 were utilized including films formed with patterns designated as DN2, DN3, and DN4. A fourth film, designated as BB1 (described in Example 2, above) was also used. The protocol was run with multiple examples of each film type.

The general protocol followed for each film was as follows:

Materials

Cell culture inserts 0.4 um pore size HDPET membrane (BO Falcon) 24 well plate (BD Falcon)
Caco-2 media
Nanostructured membranes as described above
IgG-FITC (Sigma Aldrich)
BSA-FITC (Sigma Aldrich)
Minimum Essential Medium no phenol red (Invitrogen)
TEER voltmeter
Warmed PBS
Black 96-well plate
Aluminum foil

Protocol

1. Seed Caco-2 cells on collagen coated well inserts 2 weeks before permeability assay is to be performed. Collagen coated plates are made by making a 1:1 volume of 100% ethanol to collagen. Dry surfaces in sterile hood overnight until dry.

2. Make 0.1 mg/ml solution of FITC-conjugated molecule (BSA, IgG, etc) of interest in phenol red free Alpha MEM media. Wrap in aluminum foil to protect from light.

3. Check for confluency of Caco-2 cells by measuring the resistance. Resistance should be above ~600 Ohms for confluency.

4. Aspirate old media from cell culture inserts on apical and basolateral sides. Rinse with PBS to remove any residual phenol-red dye.

5. Add 0.5 ml of FITC-conjugated solution on apical side of each insert.

6. In another 24 well plate with cell culture inserts, add 0.5 ml of warmed PBS.

7. Transfer inserts to the plate with PBS. Blot the bottom of the insert on a Kim wipe to remove residual phenol red.

8. t=0-time point: sample 75 μL from the basolateral side of insert and transfer to a black-bottom 96-well plate. Replace the volume with 75 μL of warmed PBS. Record the resistance of each well using the "chopstick" electrodes.

9. Carefully add the membrane to the appropriately labeled well. Controls are the unimprinted membranes and the cells alone. Check under a microscope that the membranes make direct contact to the cells. You should be able to see a sharp circle, indicating contact with the cells.

10. t=0 time point: repeat step 7 and then place in the incubator for 1 hour 11. t=1 time point: repeat step 7 and then place in the incubator for 1 hour 12. t=2 time point: repeat step 7

13. Measure fluorescence signal using a spectrofluorometer plate reader. FITC (excitation=490 nm, emission=520 nm)

Results

Films utilized and results obtained are summarized in Table 6, below.

TABLE 6

| | Sample no. (see Table 3) | | | | | | |
|---|---|---|---|---|---|---|---|
| | 2 | 3 | 4 | 5 | 6 | 7 | 8 |
| Pattern | DN2 | DN2 | DN2 | DN3 | DN4 | DN4 | BB1 |
| Material | PP | PS | PP | PS | PS | PP | PP |
| Effective Compression Modulus (MPa) | 5.3 | 16.3 | 0.29 | 10.4 | 32.3 | 4.8 | 7.8 |
| Effective Shear Modulus (MPa) | 5.32 | 58.9 | 218 | 319 | 77.8 | 4.4 | 26.7 |
| BET Surface Area (m²/g) | — | 0.11 | — | 0.44 | — | 4.15 | — |

TABLE 6-continued

| | Sample no. (see Table 3) | | | | | | |
|---|---|---|---|---|---|---|---|
| | 2 | 3 | 4 | 5 | 6 | 7 | 8 |
| BSA permeability increase at 120 min. (MW 66 kDa) | — | 2 | 1.9 | 3.3 | 2 | 1.4 | 1 |
| IgG permeability increase at 120 min. (MW 150 kDa) | — | 1 | — | 1 | 3.5 | — | — |

Moduli were determined according to standard methods as are known in the art as described by Schubert, et al. (Sliding induced adhesion of stiff polymer microfiber arrays: 2. Microscale behaviour, Journal Royal Society, Interface, Jan. 22, 2008. 10.1098/rsif.2007.1309)

The contact angles were measured by placing a drop of water on the surface according to standard practice. (See, e.g., Woodward, First Ten Angstroms, Portsmouth, VA)

FIG. 34 graphically illustrates the effects on permeability to bovine serum albumin (BSA) in a monolayer of cells on polystyrene films patterned with nanopatterns as described herein. The film patterns included a DN2 pattern (sample no. 3), a DN3 pattern (sample no. 5), and a DN4 pattern (sample no. 6), as indicated. Also shown are results for a non-patterned film (marked PSUI on FIG. 34) and a layer of cells with no adjacent film (marked 'cells' on FIG. 21).

FIGS. 35A and 35B graphically illustrates the effects on permeability to immunoglobulin-G (IgG) in a monolayer of cells on polystyrene films patterned with nanopatterns as described herein. The film patterns included a DN2 pattern (sample no. 3), a DN3 pattern (sample no. 5), and a DN4 pattern (sample no. 6), as indicated. Also shown are results for a non-patterned film (marked PSUI on FIGS. 35A and 35B) and a layer of cells with no adjacent film (marked 'cells' on FIGS. 35A and 35B). The results are illustrated as fold increase in permeability as a function of time measured in hours. The BSA signal was read on a fluorometer and the IgG signal was read on a spectrophotometer.

FIGS. 36A and 36B are 3D live/dead flourescein staining images showing paracellular and transcellular transport of IgG across a monolayer of cells on a polystyrene DN4 patterned surface (sample no. 6).

FIG. 37 graphically illustrates the effects on permeability to BSA in a monolayer of cells on polypropylene films patterned with nanopatterns as described herein. Patterns included BB1 (sample no. 8), DN2 (sample no. 4), and DN4 (sample no. 7), as indicated. Also shown are results for a non-patterned film (marked PSUI on FIG. 37) and a layer of cells with no adjacent film (marked 'cells' on FIG. 37).

FIG. 38 graphically illustrates the effects on permeability to IgG in a monolayer of cells on polypropylene films patterned with nanopatterns as described herein. Patterns included BB1 (sample no. 8), DN2 (sample no. 4), and DN4 (sample no. 7), as indicated. Also shown are results for a non-patterned film (marked PSUI on FIG. 38) and a layer of cells with no adjacent film (marked 'cells' on FIG. 38).

FIGS. 39A and 39B are 3D live/dead flourescein staining images showing paracellular transport of IgG across a monolayer of cells on a polypropylene DN2 patterned surface (sample no. 4).

FIGS. 40A-40F are scanning electron microscopy (SEM) images of Caco-2 cells cultured on nanopatterned surfaces. Specifically, FIGS. 40A and 40B illustrate Caco-2 cells on a flat polystyrene control film. FIGS. 40C and 40D illustrate Caco-2 cells on a polystyrene film patterned with a DN2 pattern (sample no. 3) as described above, and FIGS. 40E and 40F illustrate Caco-2 cells on a polystyrene film patterned with a DN3 (sample no. 5) pattern as described above.

Example 7

A method as described in Example 6 was utilized to examine the permeability of a monolayer of Caco-2 cells to the fusion protein therapeutic etanercept (marketed under the trade name as Enbrel®). FIG. 41 graphically illustrates the results for cell layers grown on several different patterned substrates including both polypropylene (DN2 PP—Sample 4 of Table 3) and polystyrene (DN2 PS—Sample 3 of Table 3 and DN3 PS—Sample 1 of Table 3) as well as an unimprinted polystyrene membrane (PSUI) and a layer of cells with no membrane (cells). Results are shown as a fold change from initial permeability with time. FIG. 42 illustrates the fold increase in permeability from initial t=0 at two hours (t=2) following addition of the membrane to the well for the substrates and cellular layer of FIG. 41.

Example 8

An array of microneedles including a nanopatterned surface was formed. Initially, an array of microneedles as illustrated in FIG. 2 was formed on a silicon wafer via a photolithography process. Each needle included two oppositely placed side channels, aligned with one through-die hole in the base of the needle (not visible on FIG. 2).

Microneedles were formed according to a typical micromachining process on a silicon based wafer. The wafers were layered with resist and/or oxide layers followed by selective etching (oxide etching, ORIE etching, iso etching), resist stripping, oxide stripping, and lithography techniques (e.g., iso lithography, hole lithography, slit lithography) according to standard methods to form the array of microneedles.

Following formation of the microneedle array, a 5 μm polypropylene film including a DN2 pattern formed thereon as described above in Example 1, the characteristics of which are described at sample 2 in Table 3, was laid over the

Example 9

Transdermal patches including microneedle arrays formed as described in Example 8 were formed. Patches were formed with either a DN2 pattern or a DN3 pattern on the microneedle array. The films defining the patterns that were applied to the microneedles are described in Table 7, below. Film 1 is equivalent to sample no. 2 of Table 3 and Film 2 is equivalent to sample no. 9 of Table 3.

TABLE 7

| Property | Film 1 | Film 2 |
|---|---|---|
| Pattern | DN2 | DN3 |
| Material | polypropylene | polypropylene |
| Film Thickness | 5 micrometers | 5 micrometers |
| Height of structures | 100 nm | 165 nm, 80 nm, 34 nm |
| Aspect ratio of structures | 0.5 | 0.18 |
| Average Surface Roughness $R_A$ | 16 nm | 50 nm |
| Fractal Dimension | 2.15 | 2.13 |

Control patches were also formed that had no pattern formed on the film subsequently applied to the array of microneedles. Transdermal and subcutaneous formulations of etanercept (Enbrel®) were prepared according to instructions from the drug supplier. The subcutaneous dose formulation (for the positive control) was prepared to facilitate a 4 mg/kg subcutaneous drug dose. The concentration of Enbrel® for transdermal delivery was adjusted such that an intended dosing of 200 mg/kg was achieved in a 24 hr period.

A total of 10 BALB/C mice (assigned designations #1-#10) were used in the study, 8 were transdermally dosed with Enbrel® (group 1) and 2 were subcutaneously dosed with Enbrel® (group 2) as described in Table 8, below. The transdermal patches were applied to shaved skin areas and holes formed near the microneedle tips upon application of the patch to the skin.

TABLE 8

| Group No. | Test Article | Drug | Dose Route | Dose Level | Dose volume | Blood Collection Time Points | Animal Number |
|---|---|---|---|---|---|---|---|
| 1 | Transdermal patch | Enbrel ® | Transdermal | 5 mg/subject | 0.2 ml | Pre-patch | #1, #5 |
| | | | | | | 0.5 h | #2, #6 |
| | | | | | | 2 h | #3, #7 |
| | | | | | | 6 h | #4, #8 |
| | | | | | | 24 h | #2, #6 |
| | | | | | | 72 h | #3, #7 |
| 2 | subcutaneous delivery | Enbrel ® | Subcutaneous | 4 mg/kg | 0.1 ml | 24 h | #9, #10 | microneedle array. The wafer/film structure was held on a heated vacuum box (3 in. $H_2O$ vacuum) at elevated temperature (130° C.) for a period of one hour to gently pull the film over the surface of the microneedles while maintaining the nanopatterned surface of the film.

FIG. 43 illustrates the film over the top of the array of microneedles, and FIG. 44 is a closer view of a single needle of the array including the nanopatterned film overlaying the top of the needle.

Transdermal patches used included both those defining a nanotopography on the surface (DN2 and DN3 patterns, as described above), as well as patches with no pattern of nanotopography.

Samples of whole blood were collected at the time points indicated in Table 8. Approximately 100 to 200 μl blood was taken via mandibular bleeding and then centrifuged at approximately 1300 rpm for 10 minutes in a refrigerated centrifuge (set at 4° C.). The resulting serum was aspirated and transferred within 30 minutes of blood collection/centrifugation to appropriately labeled tubes. The tubes were frozen and stored in the dark at ≤−70° C. until they were analyzed for levels of Enbrel® using Human sTNF-receptor ELISA kit (R&D Systems cat #DRT200). The space time between two blood samplings on the same subject was 24 hours, to prevent unnecessary stress placed on the subject.

FIG. 45 graphically illustrates the average PK profile of the transdermal patches that defined a nanotopography thereon. An average of the results for all nanotopography-including patches were used to represent the overall effect of incorporating a nanotopography in conjunction with a microneedle transdermal patch. As may be seen, the blood serum level rose rapidly to over 800 ng/ml/cm$^2$ of patch area within the first two hours of attachment. Following, the blood serum level gradually declined to negligible within 24 hours of attachment. The data used to develop FIG. 45 is provided below in Table 9.

TABLE 9

| Time (hr) | Blood serum concentration (ng/ml) |
| --- | --- |
| 0 | 0 |
| 0.5 | 192.1 |
| 2 | 249.25 |
| 6 | 24.4 |
| 24 | 7.2 |
| 65 | 4.0875 |

FIGS. 46A and 46B illustrate electron microscopy cross sectional views of the skin that was held in contact with the patches. The images were taken after the patches were removed (72 hours post-attachment). The sample of FIG. 46A was in contact with a patch including a nanotopography on the surface. Specifically, a DN2 pattern, as described above, was formed on the surface of the patch. The sample of FIG. 46B was held in contact with a transdermal patch that did not define a pattern of nanotopography on the surface. As may be seen, the sample of FIG. 46B shows signs of inflammation and a high density of macrophage presence.

Example 10

Transdermal patches including microneedle arrays formed as described in Example 8 were formed. Patches were formed with either a DN2 pattern or a DN3 pattern on the microneedle array as described in Table 7 of Example 9. Control patches were also formed that had no pattern formed on the film subsequently applied to the array of microneedles. Transdermal and subcutaneous formulations of etanercept (Enbrel®) were prepared according to instructions from the drug supplier.

Test subjects (rabbits) were transdermally dosed with Enbrel® or were subcutaneously (SubQ) dosed with Enbrel®. Results are illustrated graphically in FIG. 35, which provides the blood serum concentration in pg/ml as a function of time. The data used to develop FIG. 47 is provided below in Table 10, below.

TABLE 10

| Time | No structure microneedle | Subcutaneous | DN2 | Subcutaneous | DN3 |
| --- | --- | --- | --- | --- | --- |
| 0 | 0.00 | 0.00 | 0.00 | 0.00 | 0.00 |
| 0.5 | 0.00 | 157.49 | 0.00 | 1611.21 | 0.00 |

TABLE 10-continued

| Time | No structure microneedle | Subcutaneous | DN2 | Subcutaneous | DN3 |
| --- | --- | --- | --- | --- | --- |
| 2 | 0.00 | 3029.07 | 0.00 | 3504.92 | 497.17 |
| 6 | 0.00 | 3545.14 | 338.23 | 3699.24 | 796.64 |
| 12 | 0.00 | 3577.13 | 731.22 | 3571.80 | 1080.60 |
| 24 | 116.78 | 3778.71 | 785.49 | 3464.70 | 1924.24 |
| 48 | 134.23 | 3416.73 | 638.18 | 3885.31 | 1006.95 |
| 72 | 88.68 | 3356.64 | 572.77 | 3803.42 | 1172.67 |

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A method for forming a device for delivery of a rheumatoid arthritis drug across a dermal barrier, the method comprising:
    fabricating an array of microneedles;
    fabricating a pattern of first nanostructures on and projecting outward from a surface of at least one of the microneedles, wherein the pattern of first nanostructures comprises a fractal and/or fractal-like geometry,
    associating the rheumatoid arthritis drug with the microneedles such that the rheumatoid arthritis drug is in fluid communication with the microneedles.

2. The method according to claim 1, the method further comprising retaining the rheumatoid arthritis drug within a reservoir that is in fluid communication with the array of microneedles.

3. The method according to claim 2, wherein the reservoir is attached to a substrate upon which the array of microneedles are located.

4. The method according to claim 2, wherein the reservoir is removably connectable to the array of microneedles.

5. The method according to claim 1, wherein each nanostructure of the pattern of first nanostructures comprises a cross-sectional dimension less than about 500 nanometers and greater than about 5 nanometers.

6. The method according to claim 1, wherein each nanostructure of the pattern of first nanostructures comprises an aspect ratio from about 0.2 to about 5.

7. The method according to claim 1, further comprising fabricating a pattern of microstructures on the surface of the at least one of the microneedles, wherein the first nanostructures have a cross-sectional dimension smaller than a cross-sectional dimension of the microstructures.

8. The method according to claim 7, wherein the cross-sectional dimension of each microstructure of the pattern of microstructures is greater than about 500 nanometers and less than about 10 micrometers.

9. The method according to claim 7, wherein each microstructure of the pattern of microstructures comprises an aspect ratio from about 0.15 to about 5.

10. The method according to claim 7, further comprising fabricating a pattern of second nanostructures on the surface of the at least one of the microneedles, each having a cross-sectional dimension less than the cross-sectional dimension of the microstructures and greater than the cross-sectional dimension of the first nanostructures.

11. The method according to claim 1, wherein an exterior surface of the microneedles has an average surface roughness between about 10 nanometers and about 200 nanometers.

\* \* \* \* \*